(12) United States Patent
Yang

(10) Patent No.: US 11,584,719 B2
(45) Date of Patent: *Feb. 21, 2023

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventor: Jeong-Eun Yang, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 338 days.

This patent is subject to a terminal disclaimer.

(21) Appl. No.: 16/641,284

(22) PCT Filed: Aug. 22, 2018

(86) PCT No.: PCT/KR2018/009629
§ 371 (c)(1),
(2) Date: Feb. 24, 2020

(87) PCT Pub. No.: WO2019/066258
PCT Pub. Date: Apr. 4, 2019

(65) Prior Publication Data
US 2020/0207712 A1    Jul. 2, 2020

(30) Foreign Application Priority Data

Sep. 26, 2017 (KR) .................. 10-2017-0124258
Jun. 28, 2018 (KR) .................. 10-2018-0074578

(51) Int. Cl.
| | | |
|---|---|---|
| C07D 209/80 | (2006.01) | |
| H01L 51/00 | (2006.01) | |
| C07D 403/04 | (2006.01) | |
| C07D 403/10 | (2006.01) | |
| C07D 401/14 | (2006.01) | |
| C07D 471/04 | (2006.01) | |
| C07D 333/80 | (2006.01) | |
| C07D 409/04 | (2006.01) | |
| C07D 409/10 | (2006.01) | |
| C07D 307/93 | (2006.01) | |
| C07D 405/04 | (2006.01) | |
| C07D 405/10 | (2006.01) | |
| C07D 491/048 | (2006.01) | |
| C07D 495/04 | (2006.01) | |
| C07D 487/04 | (2006.01) | |
| C07D 401/04 | (2006.01) | |

(52) U.S. Cl.
CPC ......... *C07D 209/80* (2013.01); *C07D 307/93* (2013.01); *C07D 333/80* (2013.01); *C07D 401/04* (2013.01); *C07D 401/14* (2013.01); *C07D 403/04* (2013.01); *C07D 403/10* (2013.01); *C07D 405/04* (2013.01); *C07D 405/10* (2013.01); *C07D 409/04* (2013.01); *C07D 409/10* (2013.01); *C07D 471/04* (2013.01); *C07D 487/04* (2013.01); *C07D 491/048* (2013.01); *C07D 495/04* (2013.01); *H01L 51/006* (2013.01); *H01L 51/0052* (2013.01); *H01L 51/0065* (2013.01); *H01L 51/0067* (2013.01); *H01L 51/0068* (2013.01)

(58) Field of Classification Search
CPC .................... C07D 209/80; H01L 51/0052
See application file for complete search history.

(56) References Cited

U.S. PATENT DOCUMENTS

| | | | |
|---|---|---|---|
| 9,502,667 B2 | 11/2016 | Cheng et al. | |
| 11,302,874 B2 * | 4/2022 | Yang | H01L 51/0059 |
| 11,387,417 B2 * | 7/2022 | Lee | H01L 51/0074 |
| 2017/0213978 A1 | 7/2017 | Liao et al. | |
| 2018/0337340 A1 | 11/2018 | Moon | |

FOREIGN PATENT DOCUMENTS

| | | |
|---|---|---|
| KR | 20150121337 A | 10/2015 |
| KR | 20170019924 A | 2/2017 |
| KR | 20180099525 A | 9/2018 |
| KR | 20180099547 A | 9/2018 |

OTHER PUBLICATIONS

Manzano, C. A. et al., "Heterocyclic Aromatics in Petroleum Coke, Snow, Lake Sediments, and Air Samples from the Athabasca Oil Sands Region", Environmental Science and Technology, Apr. 28, 2017, vol. 51, No. 10, pp. 5445-5453, See figure 2.

Dopper, J. H. et al., "Dehydrogenation of Heterohelicenes by a Scholl Type Reaction. The Dehydrohelicenes", The Journal of Organic Chemistry, 1975, vol. 40, No. 23, pp. 3398-3401, See Scheme 2, compounds 2, 21.

Pawel Szlachcic et al., "Organic light emitting diodes (OLED) based on helical structures containing 7-membered fused rings" Dyes and Pigments, p. 16 and 53, Oct. 28, 2014.

P. Gasiorski et al., "Synthesis and Spectroscopic Study of Several Novel Annulated Azulene and Azafluoranthene Based Derivatives", J Fluoresc, 21, 2011, Abstract and p. 445, Oct. 1, 2010.

Gourav M. Upadhyay et al., "Synthesis and Photophysical Properties of Aza[n]helicenes", J. Org. Chem., vol. 81, Issue 17, pp. 7751-7759, 2016.

Chemical Abstract Compound, STN express. RN: 142042-24-8 (Jun. 26, 1992).

* cited by examiner

*Primary Examiner* — Golam M Shameem
(74) *Attorney, Agent, or Firm* — G. Creston Campbell

(57) ABSTRACT

The present disclosure relates to an organic electroluminescent compound and an organic electroluminescent device comprising the same. The organic electroluminescent device having a low driving voltage and/or a high luminous efficiency and/or a long lifespan can be provided, by comprising an organic electroluminescent compound according to the present disclosure.

6 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound that can be used in an organic electroluminescent device (OLED) field and an organic electroluminescent device comprising the same.

BACKGROUND

An electroluminescent device (EL device) is a self-light-emitting device with the advantages of providing a wider viewing angle, a greater contrast ratio, and a faster response time. The first organic EL device was developed by Eastman Kodak, by using small aromatic diamine molecules and aluminum complexes as materials for forming a light-emitting layer (see Appl. Phys. Lett. 51, 913, 1987).

An organic electroluminescent device (OLED) changes electric energy into light by the injection of a charge into an organic light-emitting material, and commonly comprises an anode, a cathode, and an organic layer formed between the two electrodes. The organic layer of the organic EL device may be composed of a hole injection layer, a hole transport layer, a hole auxiliary layer, a light-emitting auxiliary layer, an electron blocking layer, a light-emitting layer (containing host and dopant materials), an electron buffer layer, a hole blocking layer, an electron transport layer, an electron injection layer, etc., as necessary. The materials used in the organic layer can be classified into a hole injection material, a hole transport material, a hole auxiliary material, a light-emitting auxiliary material, an electron blocking material, a light-emitting material, an electron buffer material, a hole blocking material, an electron transport material, an electron injection material, etc., depending on functions. In the organic EL device, holes from an anode and electrons from a cathode are injected into a light-emitting layer by electric voltage, and an exciton having high energy is produced by the recombination of the holes and electrons. The organic light-emitting compound moves into an excited state by the energy and emits light from energy when the organic light-emitting compound returns to the ground state from the excited state.

The most important factor determining luminous efficiency in an organic EL device is light-emitting materials. The light-emitting materials are required to have the following features: high quantum efficiency, high movement degree of an electron and a hole, and uniformality and stability of the formed light-emitting material layer. The light-emitting material is classified into blue, green, and red light-emitting materials according to the light-emitting color, and further includes yellow or orange light-emitting materials. Furthermore, the light-emitting material is classified into a host material and a dopant material in a functional aspect. Recently, an urgent task is the development of an organic EL device having high efficiency and long lifespan. In particular, the development of highly excellent light-emitting material over conventional materials is urgently required, considering the EL properties necessary for medium- and large-sized OLED panels. For this, preferably, as a solvent in a solid state and an energy transmitter, a host material should have high purity and a suitable molecular weight in order to be deposited under vacuum. Furthermore, a host material is required to have high glass transition temperature and pyrolysis temperature to achieve thermal stability, high electrochemical stability to achieve a long lifespan, easy formability of an amorphous thin film, good adhesion with adjacent layers, and no movement between layers.

In addition, development of materials having a good thermal stability in a hole transport layer, a buffer layer, an electron transport layer, etc., and capable of improving the performance of an organic electroluminescent device, such as a driving voltage, a luminescent efficiency, and a lifespan, is required.

Japanese Patent Application Laid-Open No. 2014-160813 discloses a compound represented by the following structure as an organic electroluminescent compound.

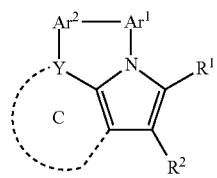

DISCLOSURE OF THE INVENTION

Problems to be Solved

The object of the present disclosure is to provide an organic electroluminescent compound capable of firstly producing an organic electroluminescent device having a low driving voltage and/or a high luminous efficiency and/or a long lifespan, and secondly, to provide the organic electroluminescent device comprising the organic electroluminescent compound.

Solution to Problems

As a result of intensive studies to solve the technical problem above, the present inventors found that a heterocyclic compound in which a 5-membered ring and aromatic rings are fused with a 7-membered ring can provide an organic electroluminescent device having a low driving voltage and/or a high luminous efficiency and/or a long lifespan characteristics, so that the present invention is completed. A compound having a low glass transition temperature (Tg) may reduce a charge mobility within the thin film and degrade the performance of an OLED device. As a result, despite its relatively low molecular weight, the present inventors have developed a novel organic electroluminescent compound which has a high Tg, so that it can provide excellent morphological stability.

More specifically, the aforementioned objective can be achieved by the organic electroluminescent compound represented by the following formula 1.

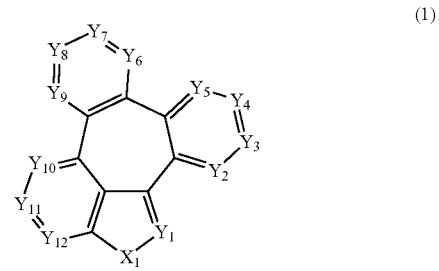

(1)

wherein,

X₁ represents N-L-(Ar)$_a$, S, or O;

L represents a single bond, a substituted or unsubstituted (C6-C30)arylene, or a substituted or unsubstituted (3- to 30-membered)heteroarylene;

Ar represents hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylami no;

$Y_1$ to $Y_{12}$ each independently represent N or $CR_1$;

$R_1$ each independently represents hydrogen, deuterium, halogen, cyano, a substituted or unsubstituted (C1-C30) alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent to form a substituted or unsubstituted ring; and a represents an integer of 1 to 4, wherein when a is 2 to 4, each of Ar may be the same or different.

Effects of the Invention

The organic electroluminescent device having a low driving voltage and/or a high luminous efficiency and/or a long lifespan can be prepared, by comprising an organic electroluminescent compound according to the present disclosure.

EMBODIMENTS OF THE INVENTION

Hereinafter, the present disclosure will be described in detail. However, the following description is intended to explain the invention, and is not meant in any way to restrict the scope of the invention.

The term "an organic electroluminescent compound" in the present disclosure means a compound that may be used in an organic electroluminescent device, and may be comprised in any layers constituting an organic electroluminescent device, if necessary.

The term "an organic electroluminescent material" in the present disclosure means a material that may be used in an organic electroluminescent device, and may comprise at least one compound. If necessary, the organic electroluminescent material may be comprised in any layers constituting an organic electroluminescent device. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, an electron injection material, etc.

An organic electroluminescent compound of the present disclosure comprises at least one compound represented by formula 1. For example, the compound represented by formula 1 may be comprised in the light-emitting layer, and when being comprised in the light-emitting layer, the compound of formula 1 may be comprised as a host.

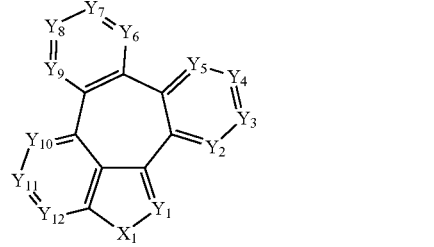

(1)

The compound represented by formula 1 above will be described in more detail as follows.

In formula 1, X₁ represents N-L-(Ar)$_a$, S, or O.

In formula 1, L represents a single bond, a substituted or unsubstituted (C6-C30)arylene, or a substituted or unsubstituted (3- to 30-membered)heteroarylene; preferably, may be a single bond, a substituted or unsubstituted (C6-C25) arylene, or a substituted or unsubstituted (5- to 25-membered)heteroarylene; more preferably, may be a single bond, an unsubstituted (C6-C18)arylene, or an unsubstituted (5- to 18-membered)heteroarylene, and the heteroarylene may include at least one nitrogen.

In one embodiment, in formula 1, L may be a single bond, a substituted or unsubstituted phenylene, a substituted or unsubstituted m-biphenylene, a substituted or unsubstituted p-biphenylene, a substituted or unsubstituted pyridinylene, a substituted or unsubstituted pyrimidylene, a substituted or unsubstituted triazinylene, a substituted or unsubstituted naphthylene, a substituted or unsubstituted quinazolinylene, or a substituted or unsubstituted quinoxalinylene.

In formula 1, Ar represents hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; preferably, may be hydrogen, a substituted or unsubstituted (C6-C25)aryl, a substituted or unsubstituted (5- to 25-membered)heteroaryl, or a substituted or unsubstituted di(C6-C25)arylamino; more preferably, may be hydrogen, a substituted or unsubstituted (C6-C18)aryl, a substituted or unsubstituted (5- to 18-membered)heteroaryl, or a substituted or unsubstituted di(C6-C18)arylamino.

In one embodiment, in formula 1, Ar may be hydrogen, a substituted or unsubstituted phenyl, a substituted or unsubstituted m-biphenyl, a substituted or unsubstituted p-biphenyl, a substituted or unsubstituted naphthyl, a substituted or unsubstituted pyridiyl, a substituted or unsubstituted pyrimidinyl, a substituted or unsubstituted triazinyl, a substituted or unsubstituted quinazolinyl, a substituted or unsubstituted quinoxalinyl, a substituted or unsubstituted carbazolyl, a substituted or unsubstituted diphenylamino, or a substituted or unsubstituted fluorenylphenylamino.

In formula 1, a represents an integer of 1 to 4, and when a is 2 to 4, each of Ar may be the same or different, e.g., when a is 2, Ar may be all phenyl or each may be phenyl and naphthyl, or phenyl and fluorenyl.

In formula 1, $Y_1$ to $Y_{12}$ each independently represent N or $CR_1$. According to one embodiment of the present disclosure, $Y_1$ to $Y_{12}$ may be all $CR_1$, and according to another embodiment of the present disclosure, at least one of $Y_1$ to $Y_{12}$ may be N.

In formula 1, $R_1$ each independently represents hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent to form a substituted or unsubstituted ring, e.g., may be linked to an adjacent substituent to form a substituted or unsubstituted, (C3-C30) mono- or polycyclic, alicyclic or aromatic ring, or the combination thereof, whose carbon atom may be replaced with at least one heteroatom selected from nitrogen, oxygen, and sulfur; preferably, may be hydrogen, a substituted or unsubstituted (C1-C20)alkyl, a substituted or unsubstituted (C6-C25)aryl, a substituted or unsubstituted (5- to 25-membered)heteroaryl, or a substituted or unsubstituted di(C6-C25)arylamino; or may be linked to an adjacent substituent to form a substituted or unsubstituted, (C3-C25) mono- or polycyclic, aromatic ring, whose at least one carbon atom may be replaced with nitrogen; more preferably, may be hydrogen, a substituted or unsubstituted (C1-C10)alkyl, a substituted or unsubstituted (C6-C18)aryl, a substituted or unsubstituted (5- to 18-membered)heteroaryl, or a substituted or unsubstituted di(C6-C18)arylamino; or may be linked to an adjacent substituent to form a substituted or unsubstituted, (C6-C18) mono- or polycyclic, aromatic ring, whose at least one carbon atom may be replaced with nitrogen.

In one embodiment, in formula 1, $R_1$ each independently may be hydrogen, a substituted or unsubstituted methyl, a substituted or unsubstituted phenyl, a substituted or unsubstituted m-biphenyl, a substituted or unsubstituted p-biphenyl, a substituted or unsubstituted naphthyl, a substituted or unsubstituted pyridyl, a substituted or unsubstituted pyrimidinyl, a substituted or unsubstituted triazinyl, a substituted or unsubstituted quinazolinyl, a substituted or unsubstituted quinoxalinyl, or a substituted or unsubstituted phenylbiphenylamino.

According to one embodiment of the present disclosure, in formula 1, two adjacents among $Y_1$ to $Y_{12}$ represent $CR_1$, and two adjacent $R_1$ may be fused with each other to form a ring represented by any one of the following formulae 2 to 5. For example, the compound of formula 1 may containe at least one ring of the following formulae 2 to 5.

In one embodiment, the ring may be a dibenzothiophene ring, a dibenzofuran ring, a naphthalene ring, a phenanthrene ring, or a substituted or unsubstituted carbazole ring.

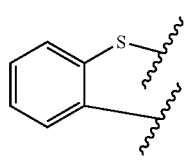

(2)

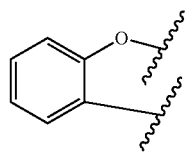

(3)

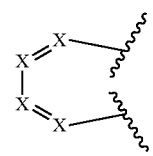

(4)

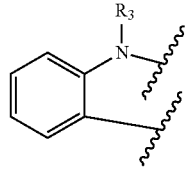

(5)

In formulae 2 to 5, ⌇ represents a linking site with C in adjacent $CR_1$ of formula 1.

In formula 4, X represents N or $CR_2$. According to one embodiment of the present disclosure, X may be all $CR_2$, and according to another embodiment of the present disclosure, at least one of X may be N.

$R_2$ each independently represents hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, preferably, may be a substituted or unsubstituted (C6-C25)aryl or a substituted or unsubstituted (5- to 25-membered)heteroaryl, more preferably, may be an unsubstituted (C6-C18)aryl or an unsubstituted (5- to 18-membered)heteroaryl.

In formula 5, $R_3$ represents hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, preferably, may be a substituted or unsubstituted (C6-C25)aryl or a substituted or unsubstituted (5- to 25-membered)heteroaryl, more preferably, may be an unsubstituted (C6-C18)aryl or an unsubstituted (5- to 18-membered)heteroaryl. For example, in formula 5, $R_3$ may be phenyl.

In formula 1, the heteroaryl(ene) each independently contains at least one heteroatom selected from B, N, O, S, Si, and P, preferably, may contain at least one heteroatom selected from N, O, and S, more preferably, may contain at least one nitgren atom.

Herein, "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, and tert-butyl, etc. "(C2-C30)alkenyl" is meant to be a linear or branched alkenyl having 2 to 30 carbon atoms constituting the chain, in which the number of carbon atoms is preferably 2 to 20, and more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is meant to be a linear or branched alkynyl having 2 to 30 carbon atoms constituting the chain, in which the number of carbon atoms is preferably 2 to 20, and more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7, and includes cyclopropyl, cyclobutyl, cyclopentyl, cyclohexyl, etc. "(3-to 7-membered)heterocycloalkyl" is meant to be a cycloalkyl having 3 to 7 ring backbone atoms, preferably 5 to 7 ring backbone atoms, including at least one heteroatom selected from the group consisting of B, N, O, S, Si, and P, and preferably O, S, and N, and includes tetrahydrofuran, pyrrolidine, thiolane, tetrahydropyran, etc. "(C6-C30)aryl(ene)" is meant to be a monocyclic or fused ring radical derived from an aromatic hydrocarbon having 6 to 30 ring backbone carbon atoms, in which the number of the ring backbone carbon atoms is preferably 6 to 25, more preferably 6 to 18, may be partially saturated, and may comprise a spiro structure. The aryl includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirofluorenyl, etc. "(3- to 30-membered)heteroaryl(ene)" is meant to be an aryl group having at least one heteroatom selected from the group consisting of B, N, O, S, Si, and P, and having 3 to 30, preferably 5 to 25, and more preferably 5 to 18 ring backbone atoms; having preferably 1 to 4 heteroatoms, and may be a monocyclic ring, or a fused ring condensed with at least one benzene ring; may be partially saturated. In addition, the heteroaryl(ene) may be one formed by linking at least one heteroaryl or aryl group to a heteroaryl group via a single bond(s); and may include a spiro structure. The heteroaryl includes a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl such as benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, benzocarbazolyl, phenoxazinyl, phenothiazinyl, phenanthridinyl, benzodioxolyl, dihydroacrylidinyl, etc. "Halogen" includes F, Cl, Br, and I.

Herein, "substituted or unsubstituted ring" means a substituted or unsubstituted, (C3-C30) mono- or polycyclic, alicyclic or aromatic ring, or the combination thereof, preferably, may be a substituted or unsubstituted, (C5-C25) mono- or polycyclic, alicyclic or aromatic ring, or the combination thereof, more preferably, may be a substituted or unsubstituted, (C5-C18) mono- or polycyclic, alicyclic or aromatic ring, or the combination thereof.

In addition, "substituted" in the expression "substituted or unsubstituted" means that a hydrogen atom in a certain functional group is replaced with another atom or another functional group, i.e., a substituent. The substituents of the substituted (C1-C30)alkyl, the substituted (C6-C30)aryl(ene), the substituted (3- to 30-membered)heteroaryl(ene), the substituted (C3-C30)cycloalkyl, the substituted (C1-C30)alkoxy, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di-(C1-C30)alkylamino, the substituted mono- or di-(C6-C30)arylamino, the substituted (C1-C30)alkyl(C6-C30)arylamino, and the substituted ring, in L, Ar, and $R_1$ of formula 1 are each independently at least one selected from the group consisting of deuterium, halogen, cyano, carboxyl, nitro, hydroxyl, (C1-C30)alkyl, halo(C1-C30)alkyl, (C2-C30)alkenyl, (C2-C30)alkynyl, (C1-C30)alkoxy, (C1-C30)alkylthio, (C3-C30)cycloalkyl, (C3-C30)cycloalkenyl, (3- to 7-membered)heterocycloalkyl, (C6-C30)aryloxy, (C6-C30)arylthio, (5- to 30-membered)heteroaryl-substituted or unsubstituted (C6-C30)aryl, di(C6-C30)arylamino-substituted (C6-C30)aryl, (C6-C30)aryl-substituted or unsubstituted (5- to 30-membered)heteroaryl, tri(C1-C30)alkylsilyl, tri(C6-C30)arylsilyl, di(C1-C30)alkyl(C6-C30)arylsilyl, (C1-C30)alkyldi(C6-C30)arylsilyl, amino, a mono- or di-(C1-C30)alkylamino, (C1-C30)alkyl-substituted or unsubstituted mono- or di-(C6-C30)arylamino, (C1-C30)alkyl(C6-C30)arylamino, (C1-C30)alkylcarbonyl, (C1-C30)alkoxycarbonyl, (C6-C30)arylcarbonyl, di(C6-C30)arylboronyl, di(C1-C30)alkylboronyl, (C1-C30)alkyl(C6-C30)arylboronyl, (C6-C30)ar(C1-C30)alkyl, and (C1-C30)alkyl(C6-C30)aryl; preferably, may be di(C6-C25)arylamino-substituted or unsubstituted (C6-C25)aryl, (C6-C25)aryl-substituted or unsubstituted (5- to 25-membered)heteroaryl, or di(C6-C30)arylamino; more preferably, may be di(C6-C18)arylamino-substituted or unsubstituted (C6-C18)aryl, (C6-C18)aryl-substituted (5- to 18-membered)heteroaryl, or di(C6-C18)arylamino, for example, phenyl; naphthyl; carbazole; pyridine, pyrimidine, or triazine substituted with one or more phenyl; amine substituted with one or more phenyl, amine substituted with phenyl and fluorenyl, amine substituted with phenyl and biphenyl, or triazine substituted with phenyl and naphthyl.

The compound represented by formula 1 may be more specifically illustrated by the following compounds, but is not limited thereto:

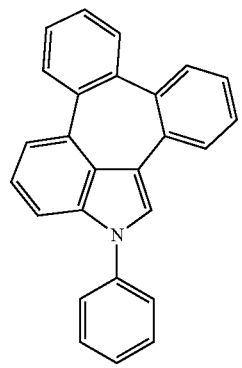

C-1

C-2 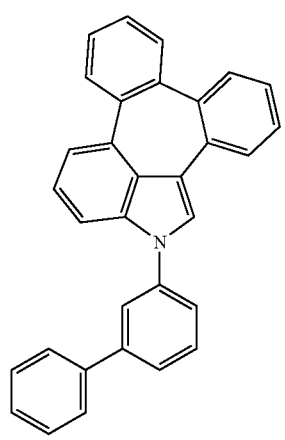
C-3 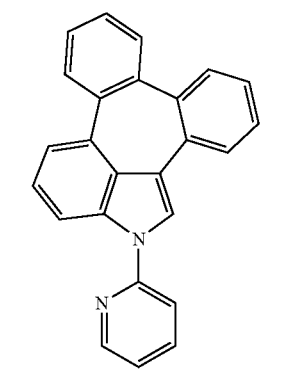
C-4 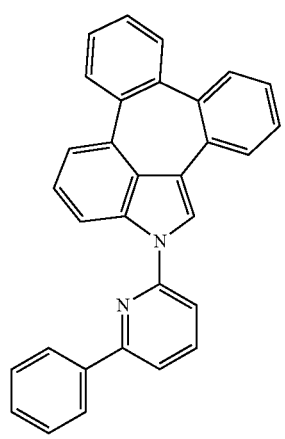
C-5 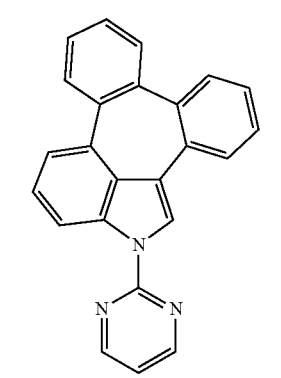
C-6 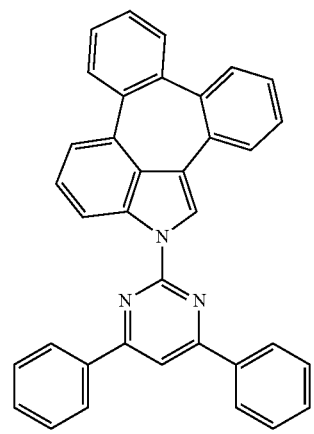
C-7 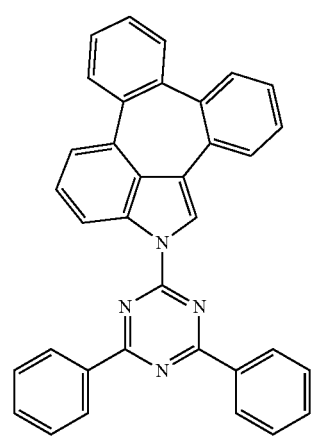
C-8 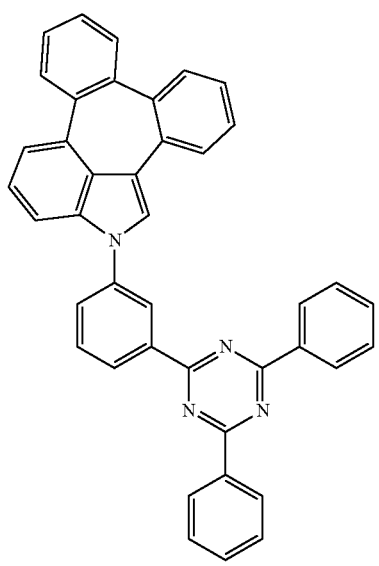

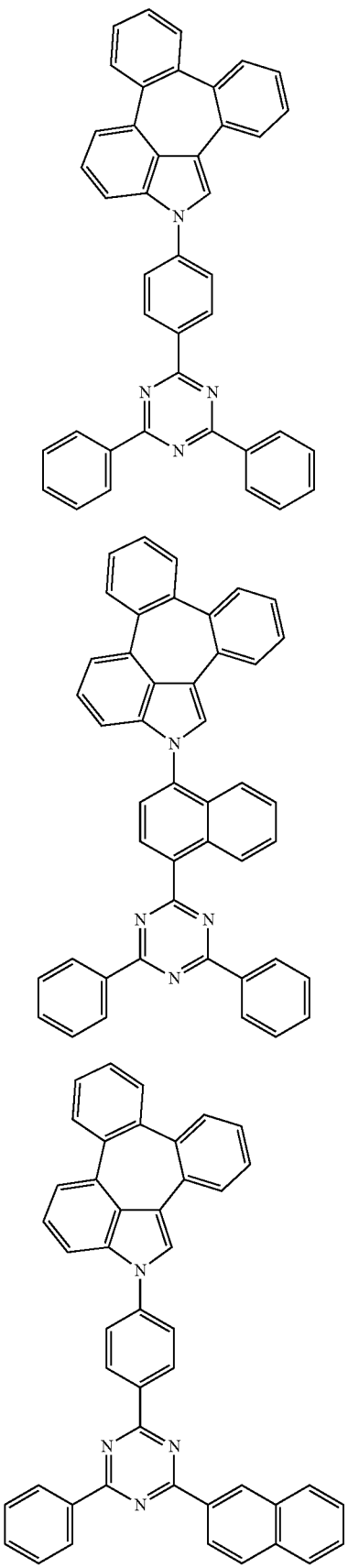
C-9
C-10
C-11
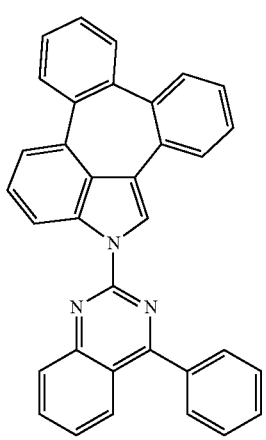
C-12
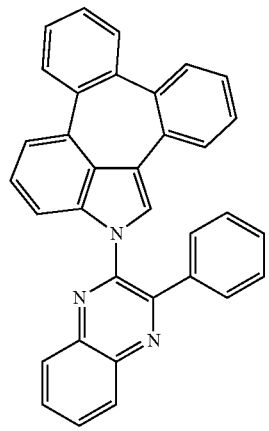
C-13
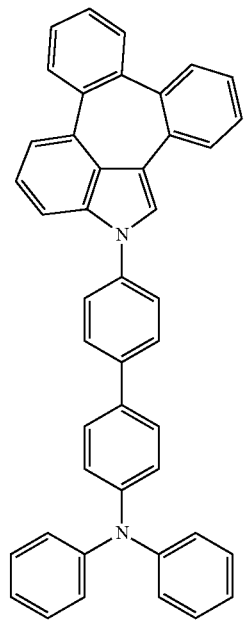
C-14

C-15
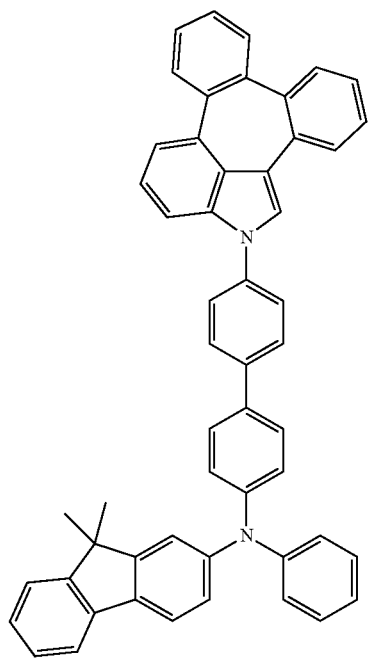
C-16
C-17
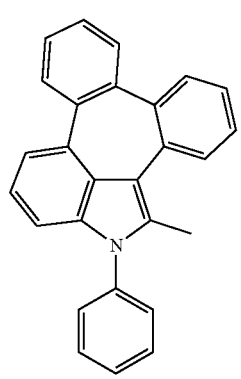
C-18
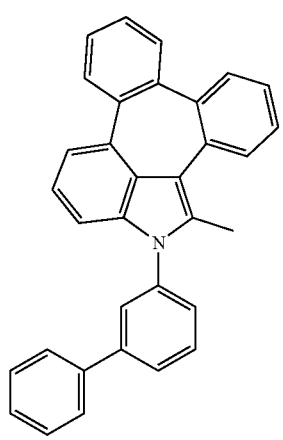
C-19
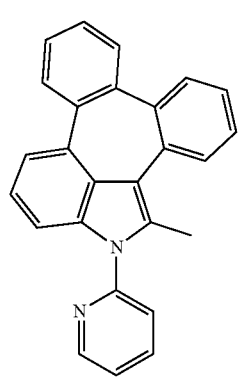
C-20
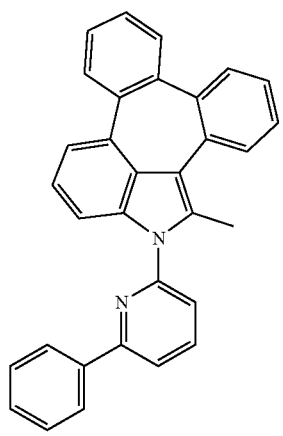
C-21

-continued
C-22
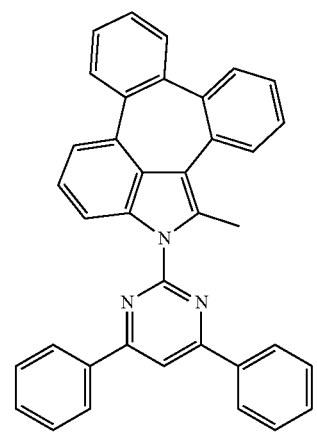
C-23
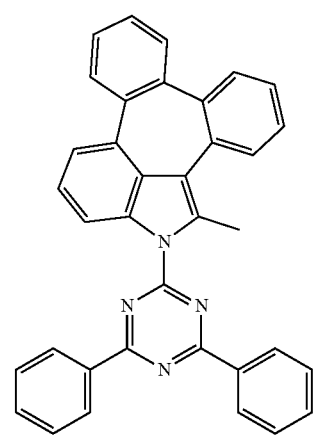
C-24
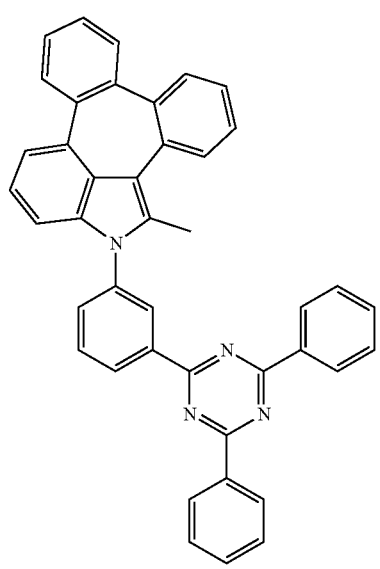
-continued
C-25
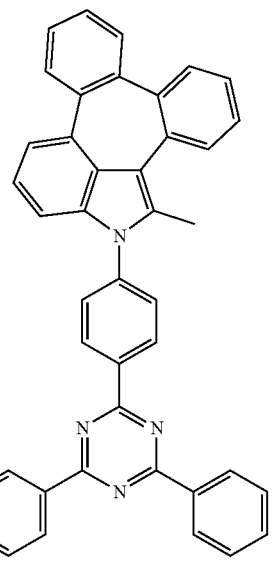
C-26
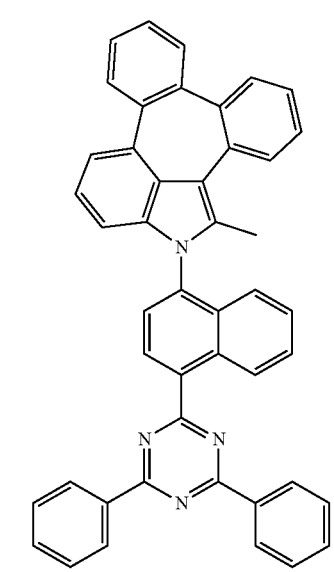
C-27
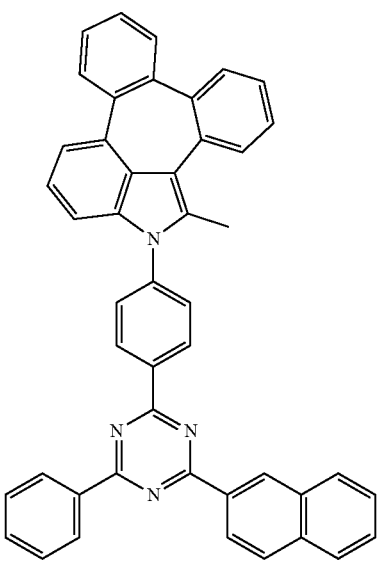

C-28
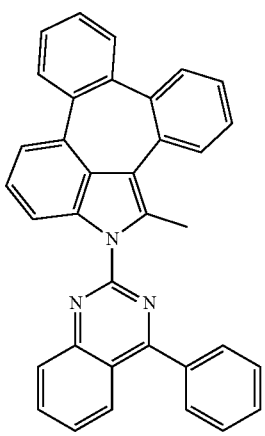
C-29
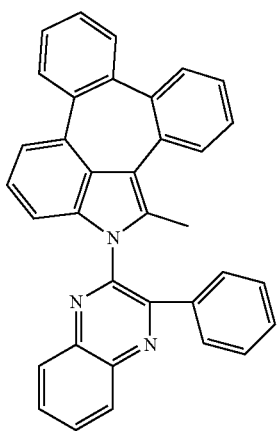
C-30
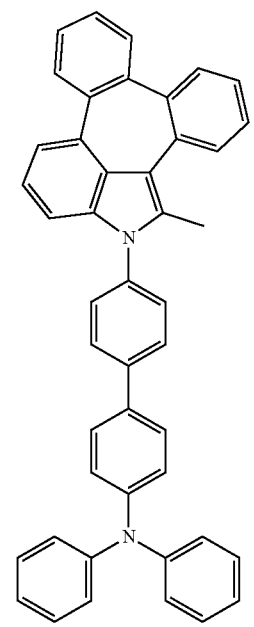
C-31
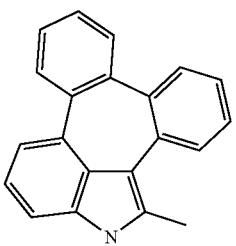
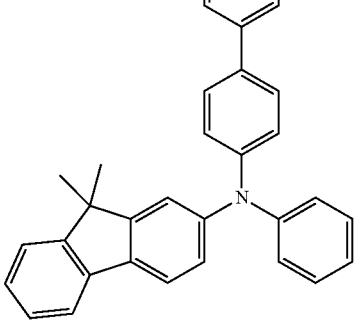
C-32
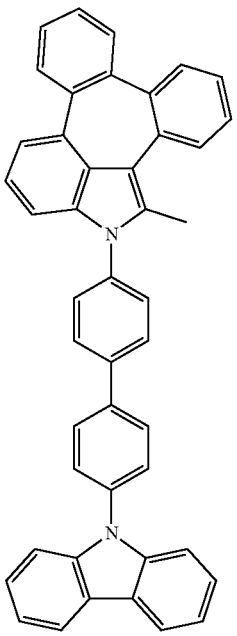
C-33
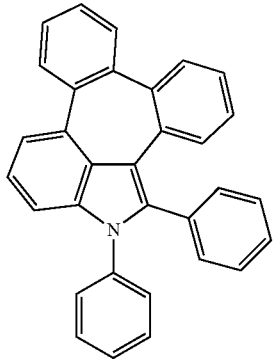

C-34
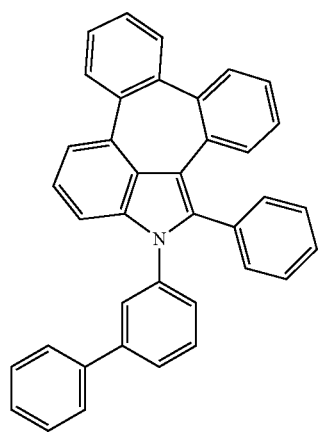
C-35
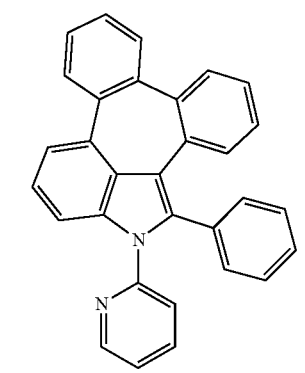
C-36
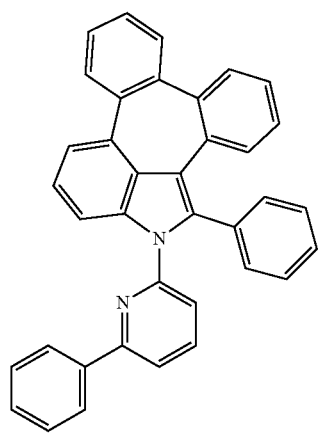
C-37
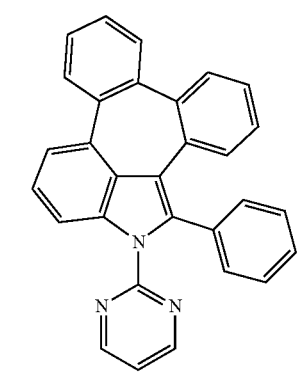
C-38
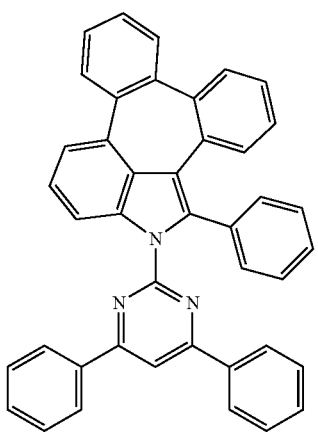
C-39
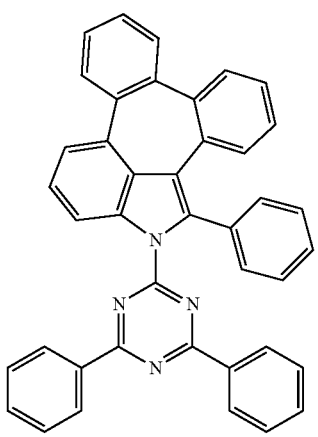
C-40
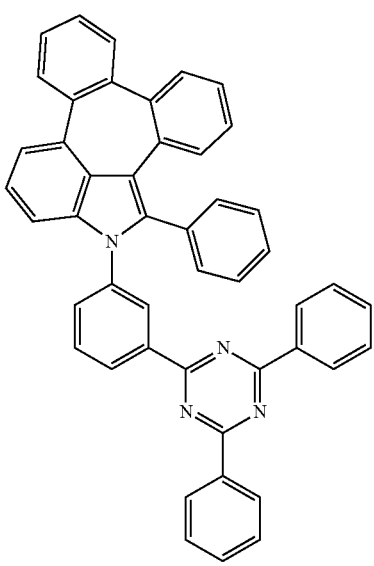

C-41
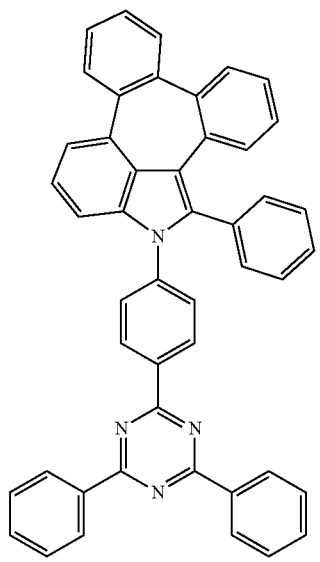
C-42
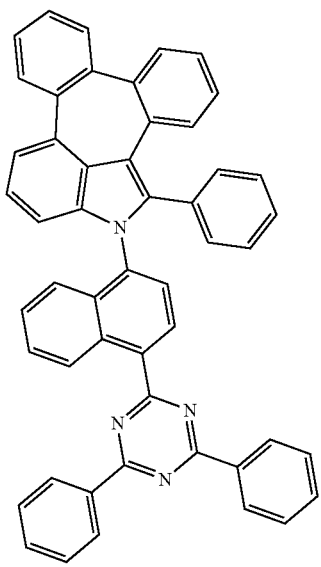
C-43
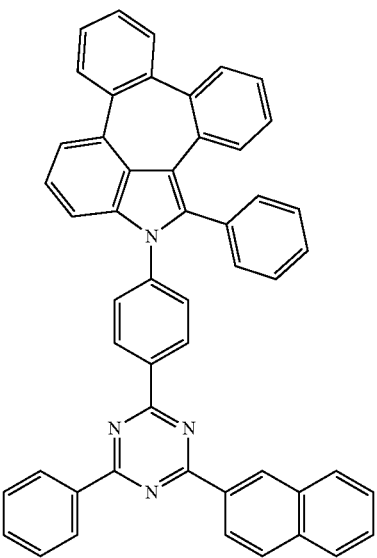
C-44
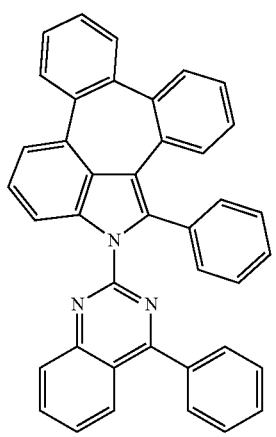
C-45
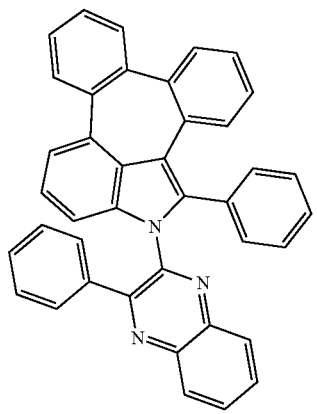

C-46
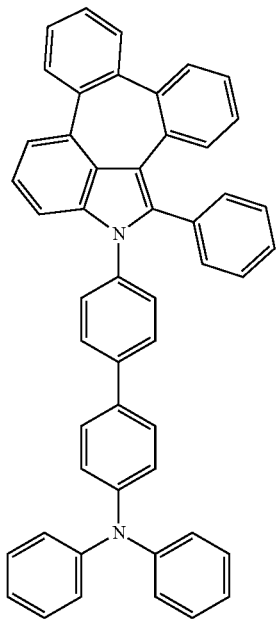
C-47
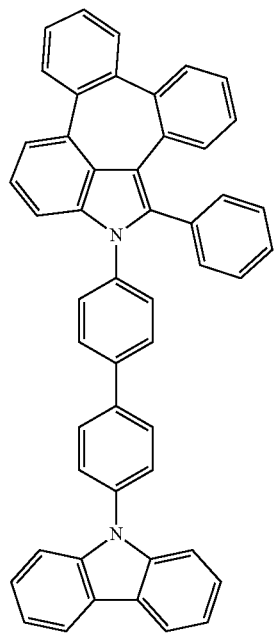
C-48
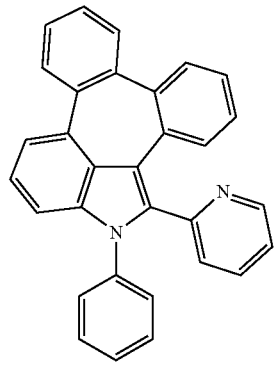
C-49
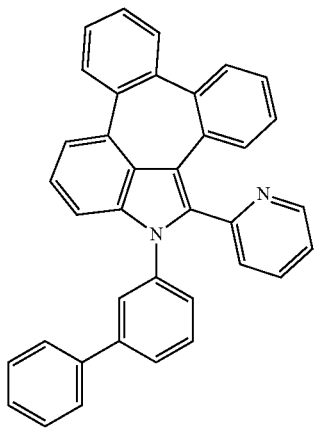
C-50

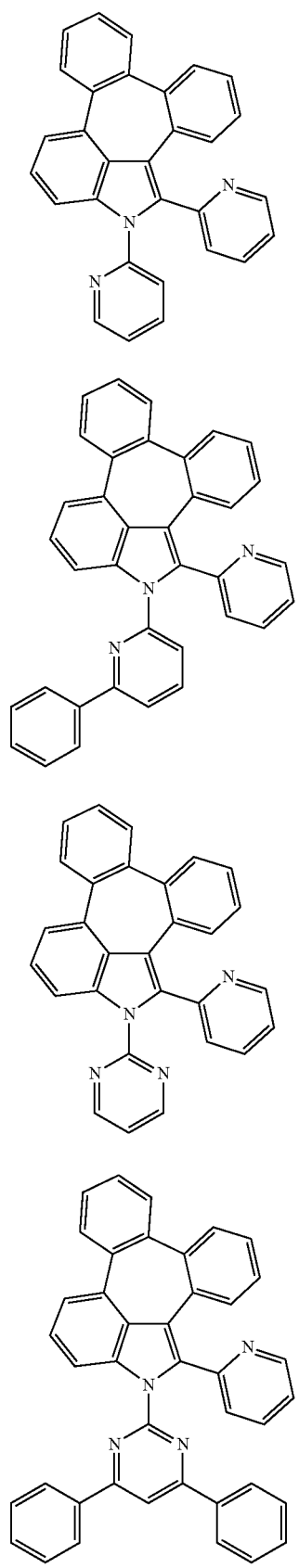
C-51
C-52
C-53
C-54
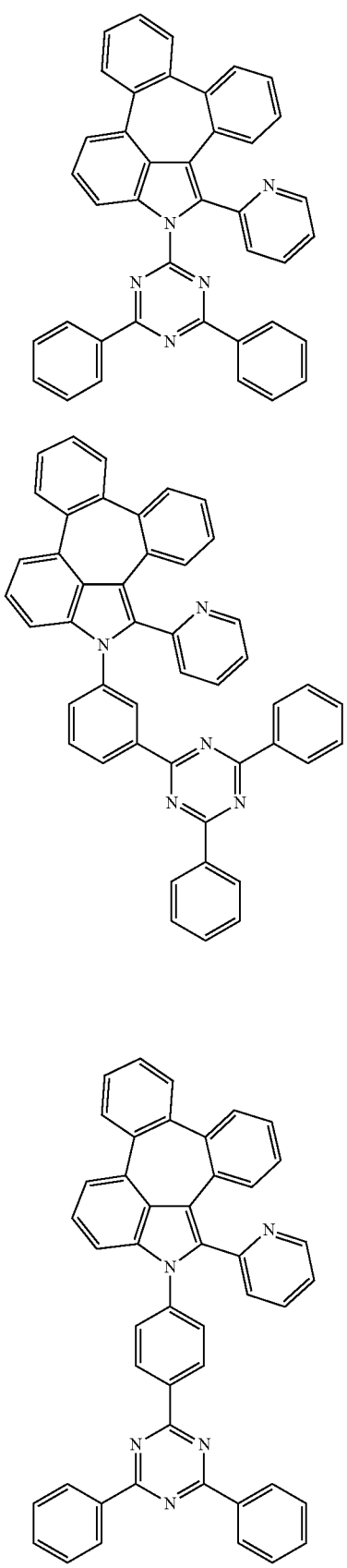
C-55
C-56
C-57

C-58
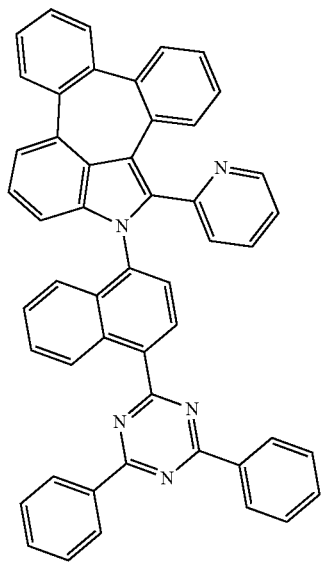
C-59
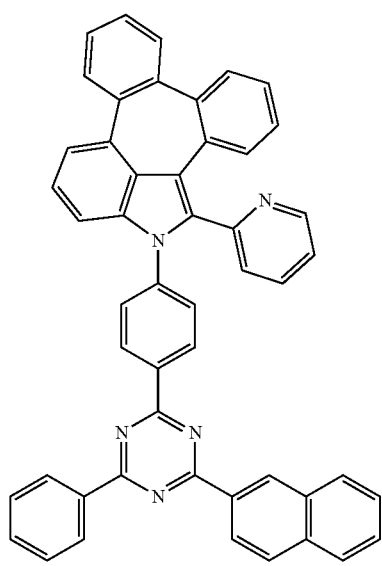
C-60
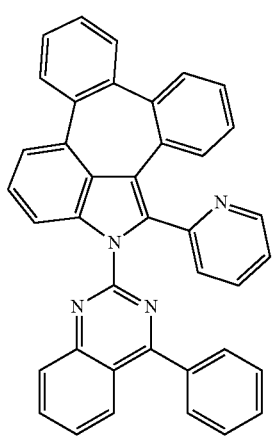
C-61
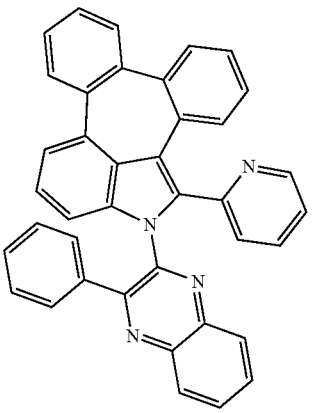
C-62
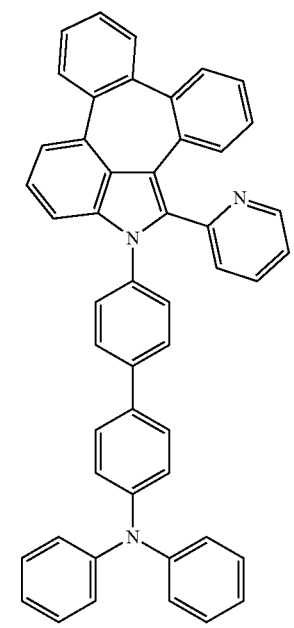

-continued
C-63
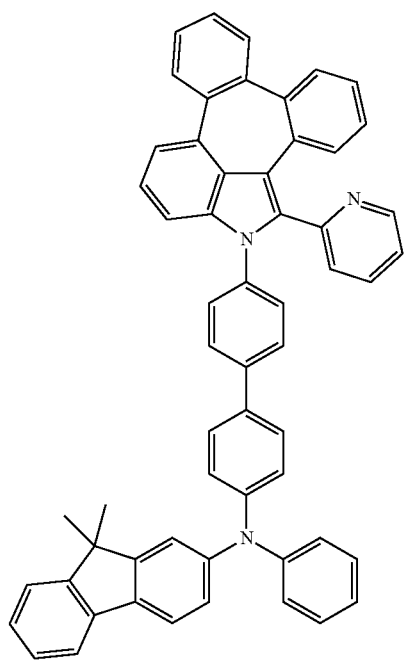
C-64
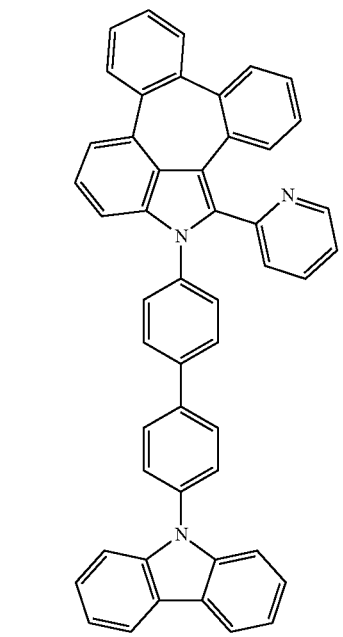
C-65
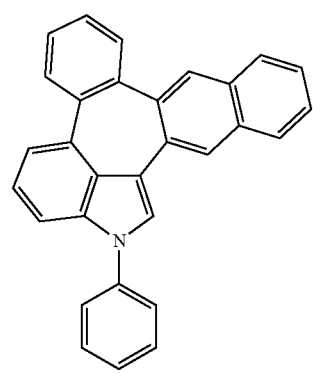
-continued
C-66
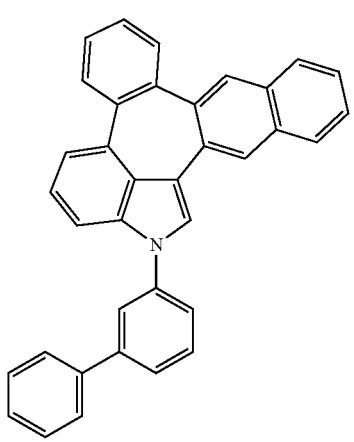
C-67
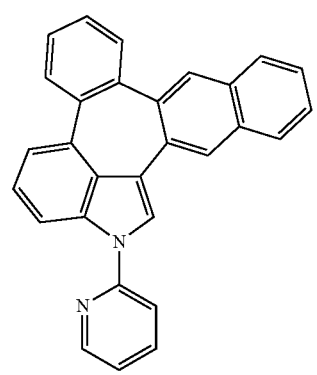
C-68
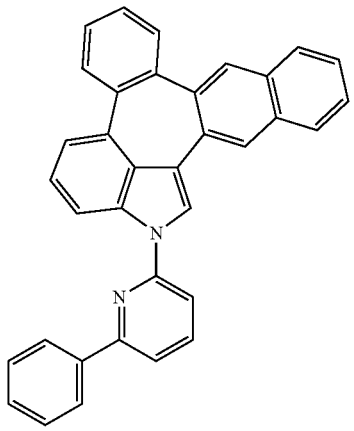
C-69
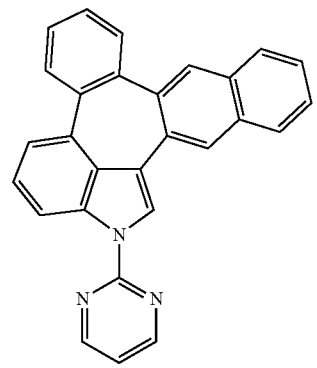

C-70
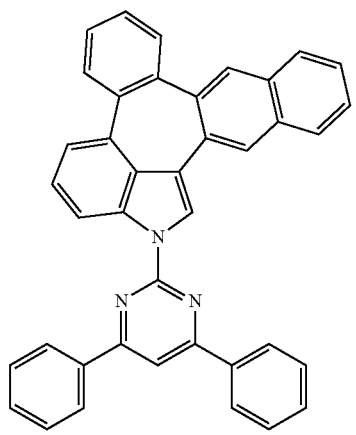
C-71
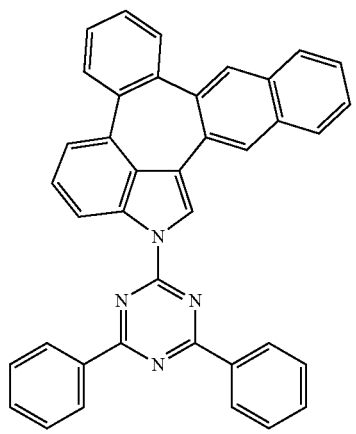
C-72
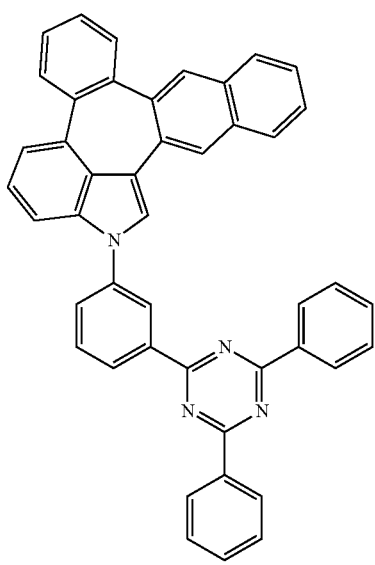
C-73
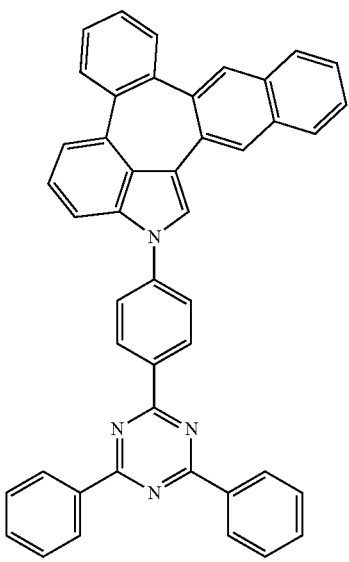
C-74
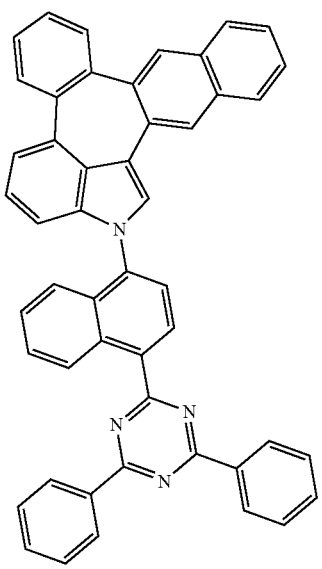

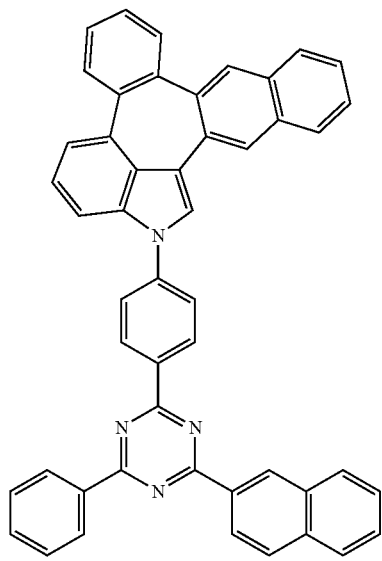
C-75
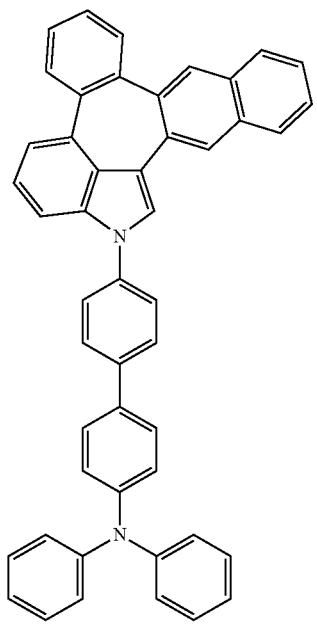
C-78
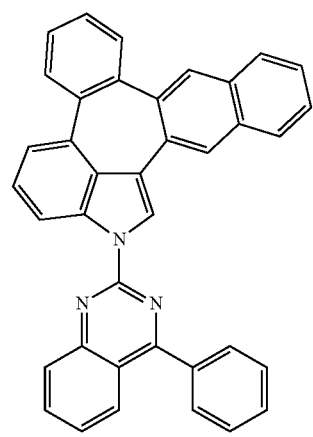
C-76
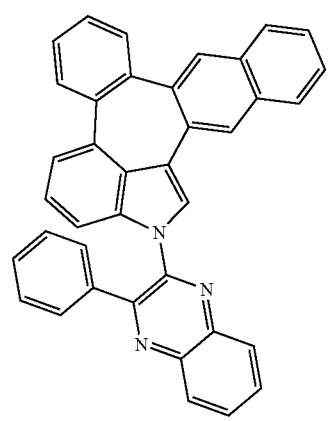
C-77
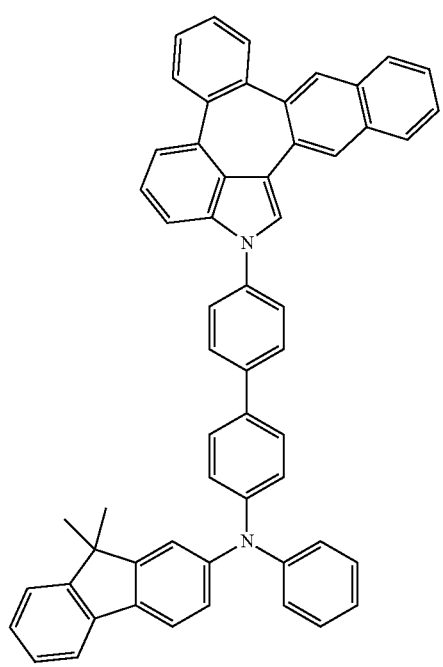
C-79

C-80 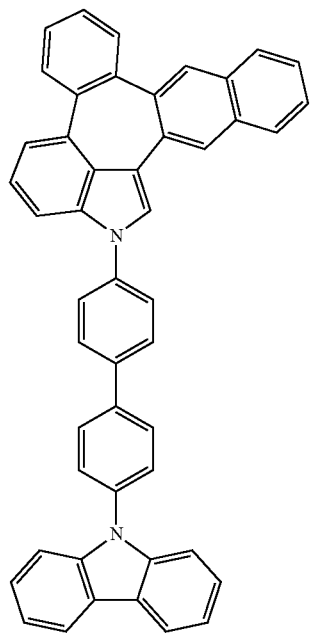
C-81 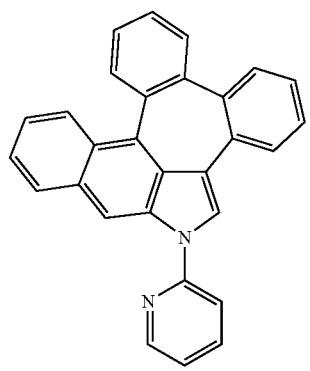
C-82
C-83 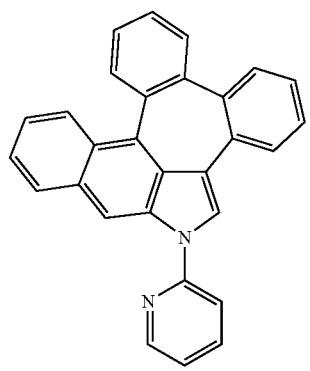
C-84 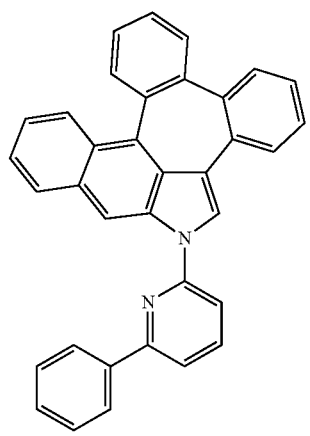
C-85 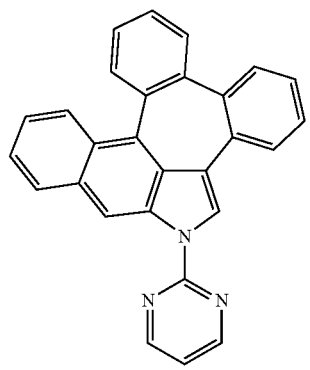
C-86 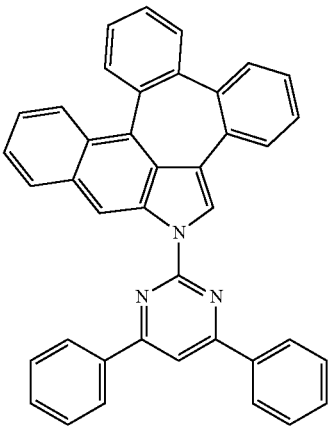

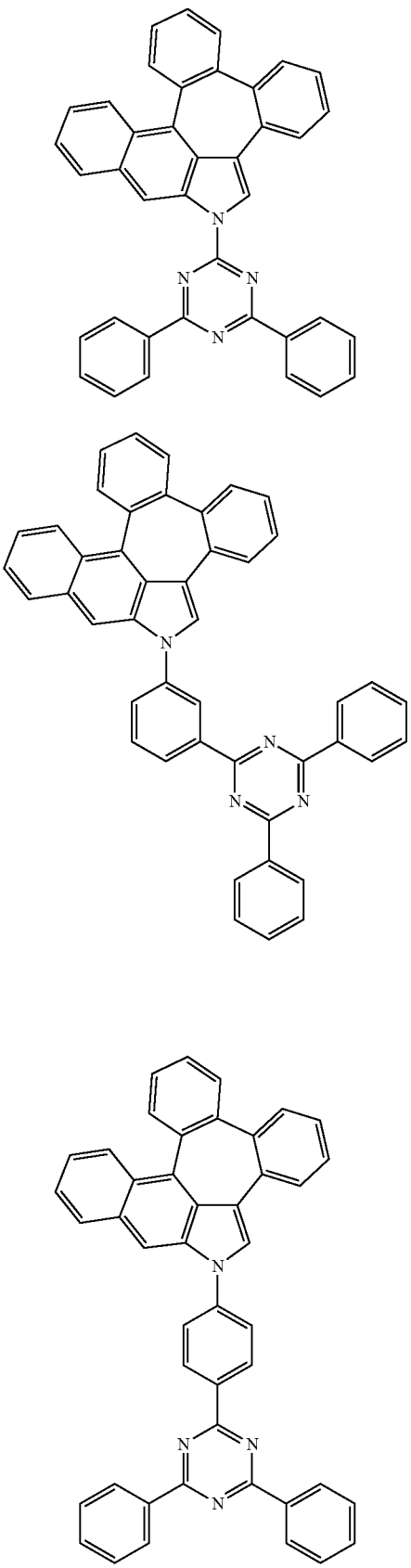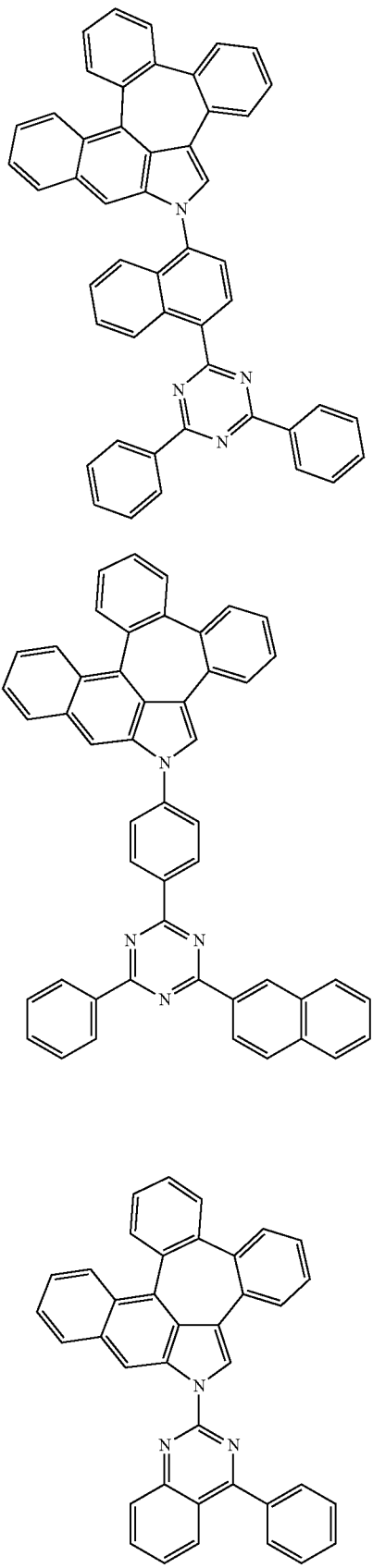

C-93
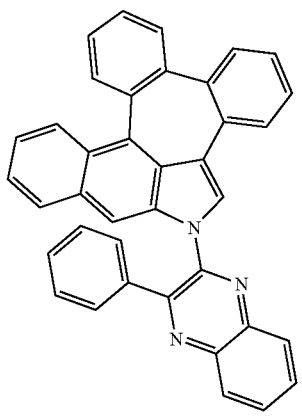
C-94
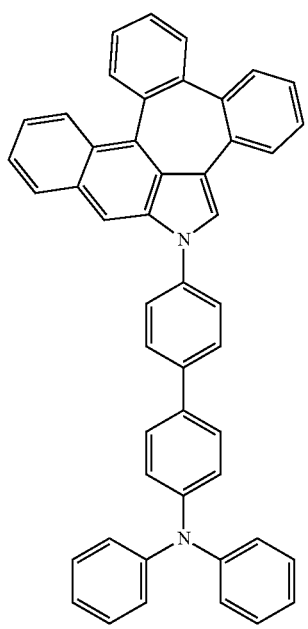
C-95
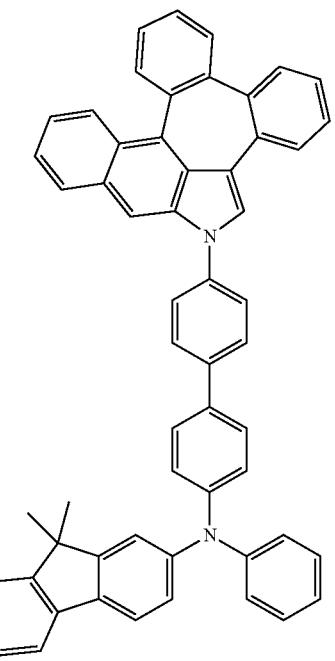
C-96
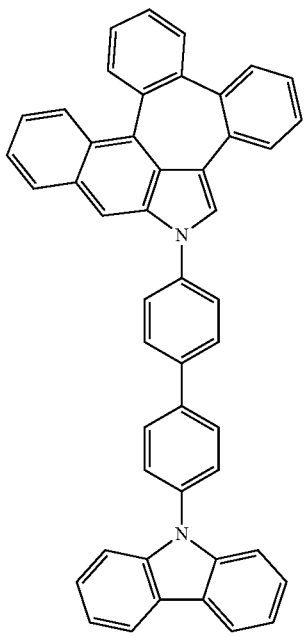

C-97
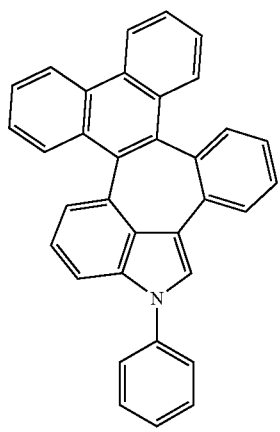
C-100
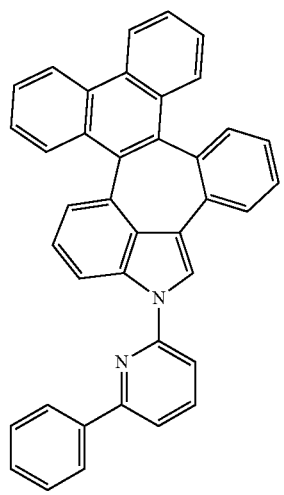
C-98
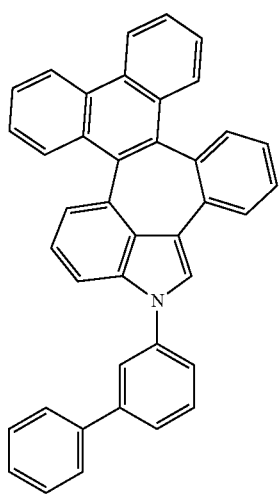
C-101
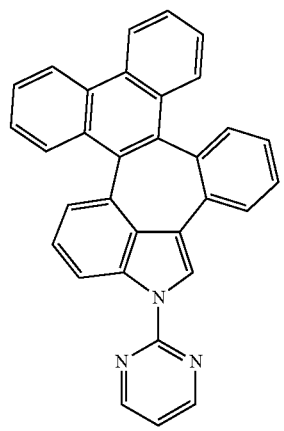
C-99
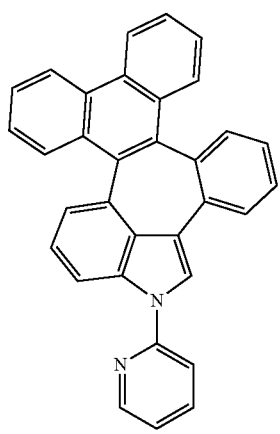
C-102
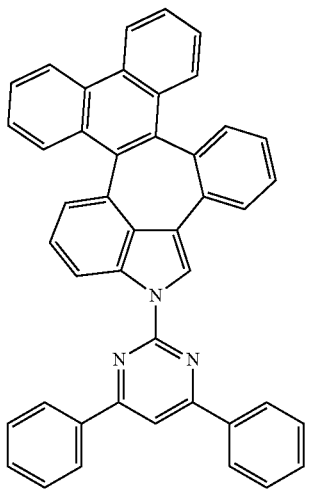

C-103
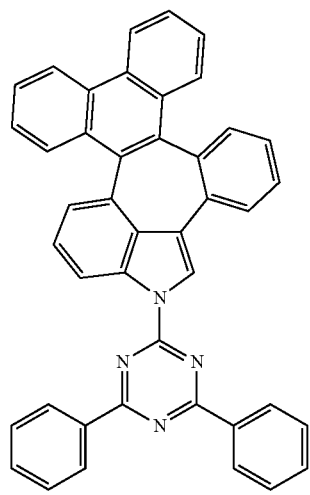
C-104
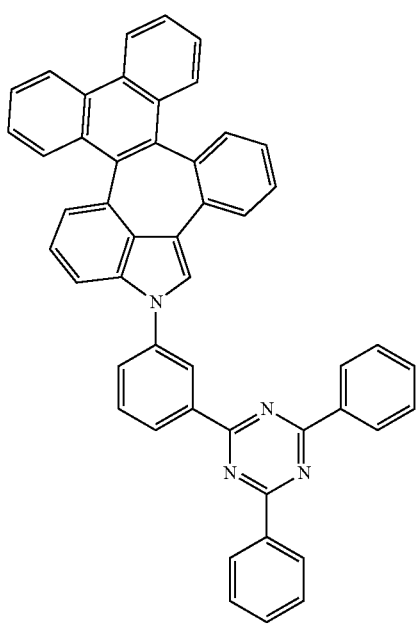
C-105
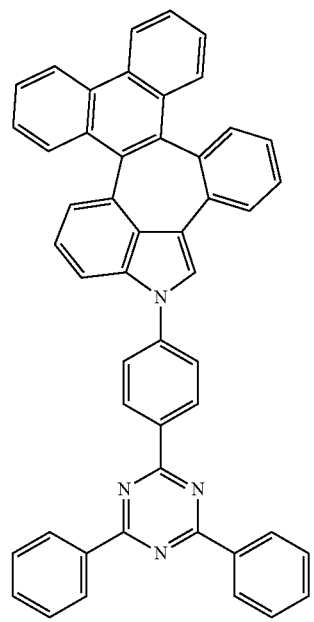
C-106
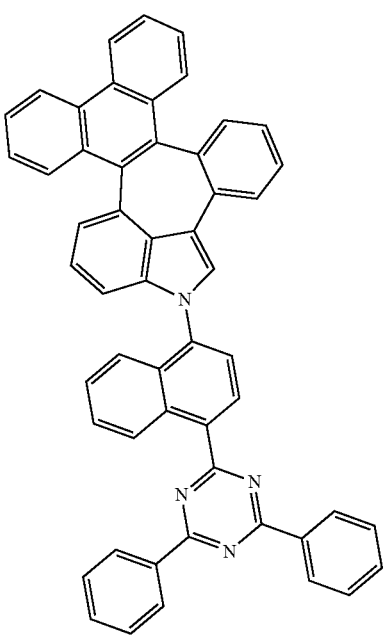

C-107
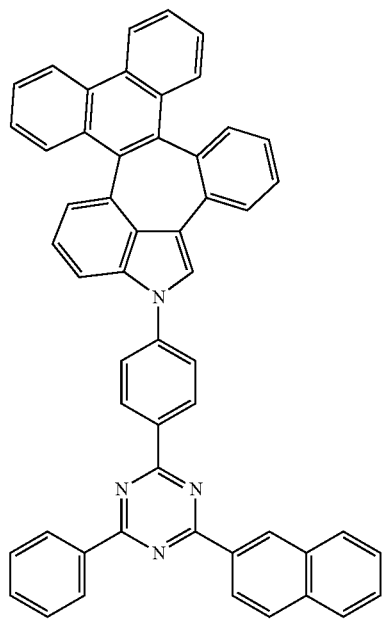
C-108
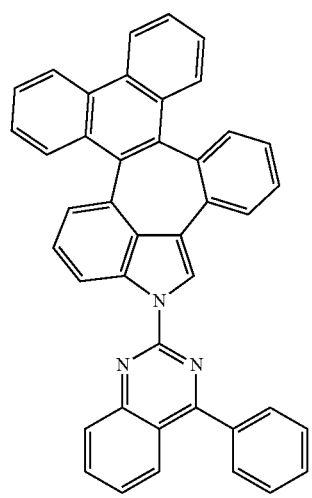
C-109
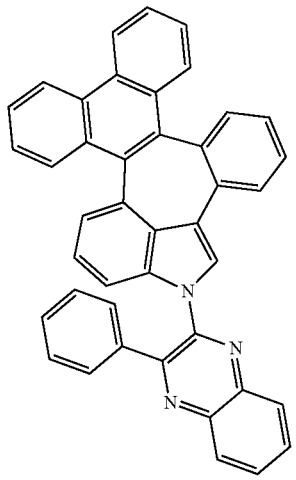
C-200
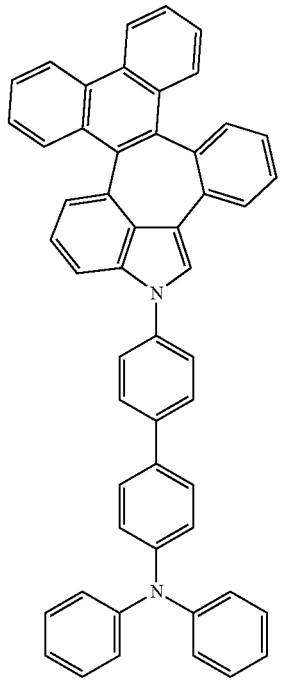
C-201
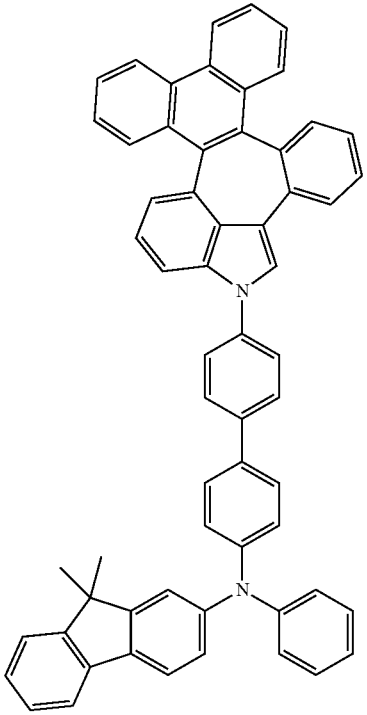

C-202
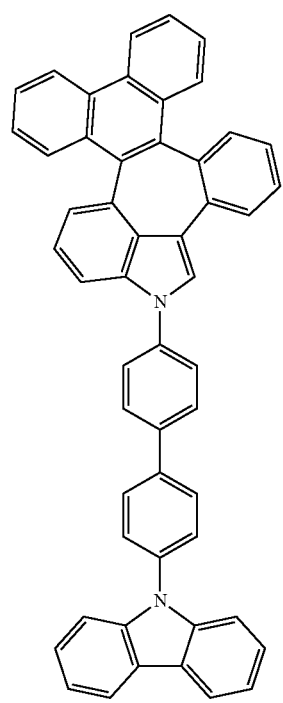
C-203
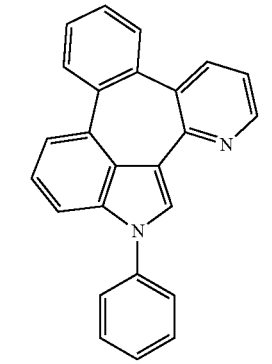
C-204
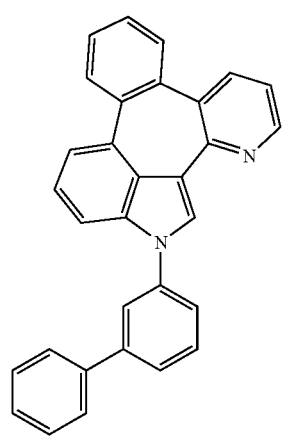
C-205
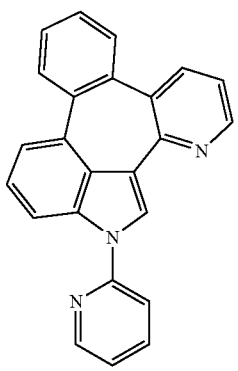
C-206
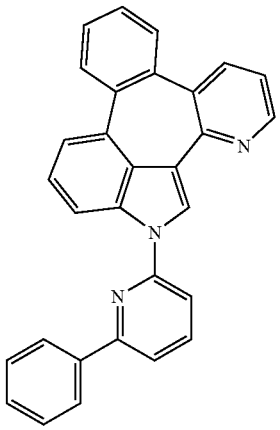
C-207
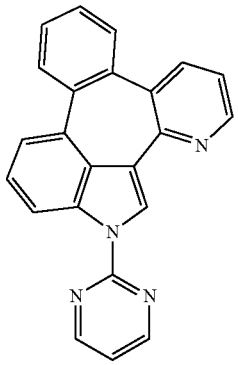
C-208
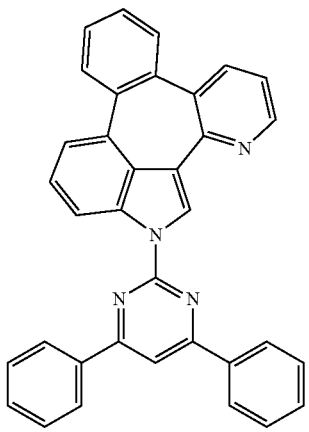

C-209
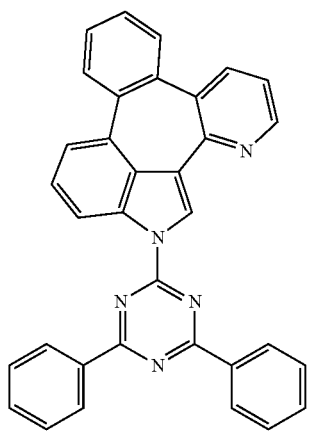
C-210
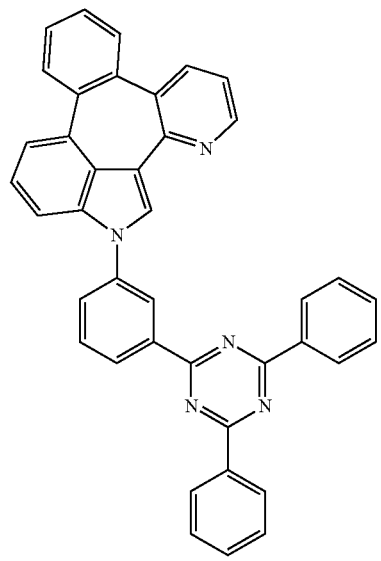
C-211
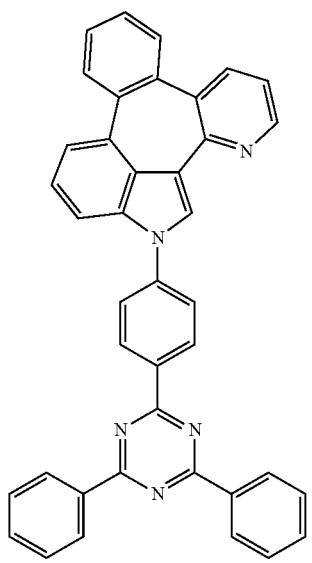
C-212
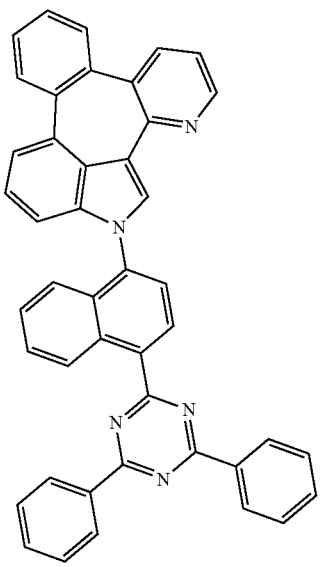
C-213
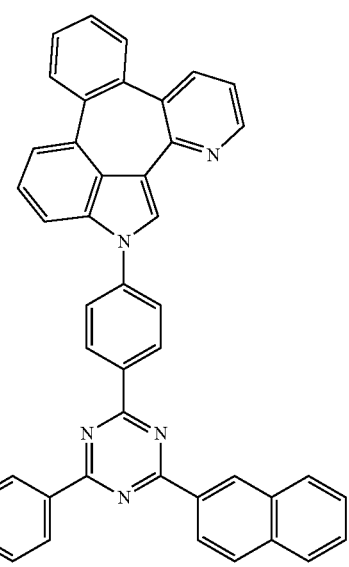
C-214
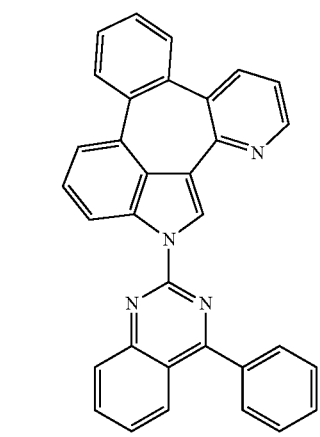

C-215
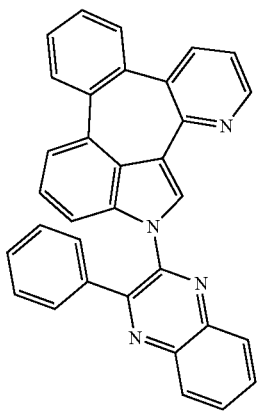
C-217
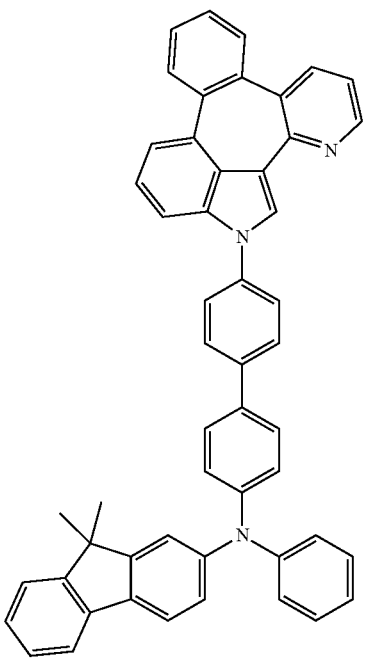
C-216
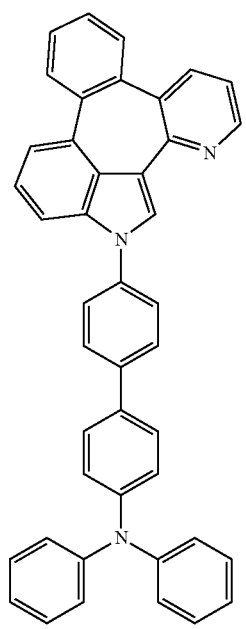
C-218
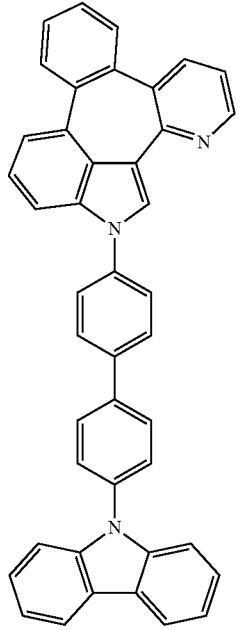

219 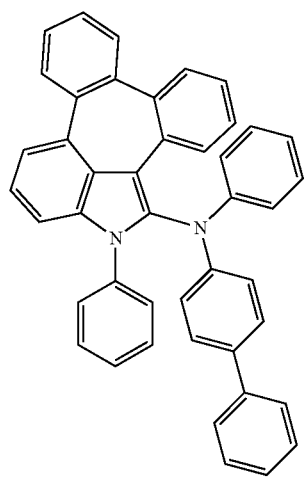
222 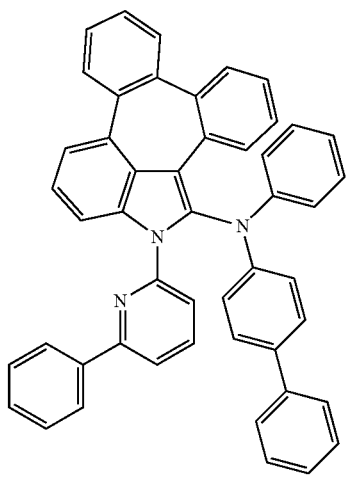
220 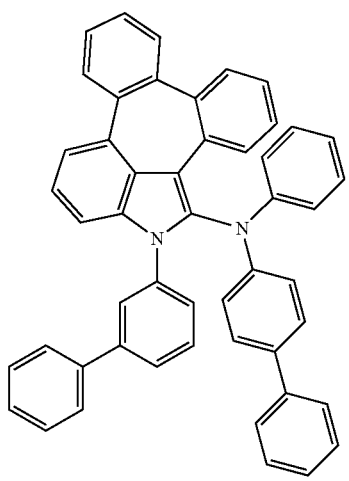
223 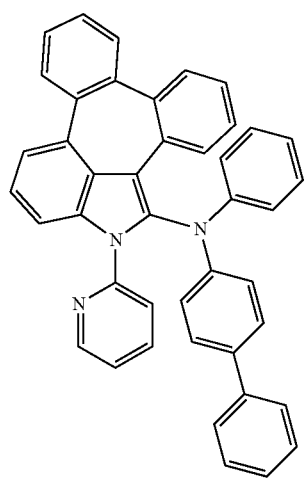
221 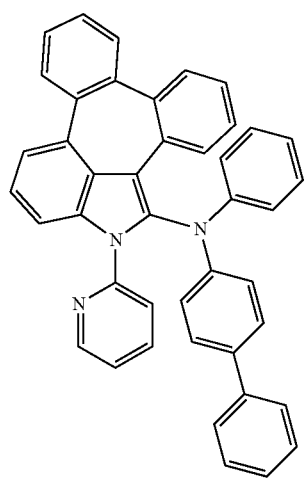
224 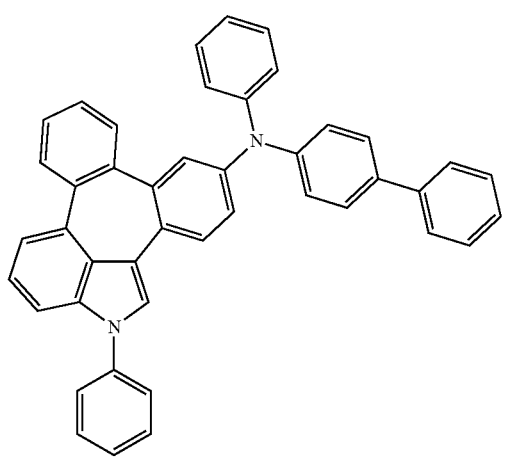

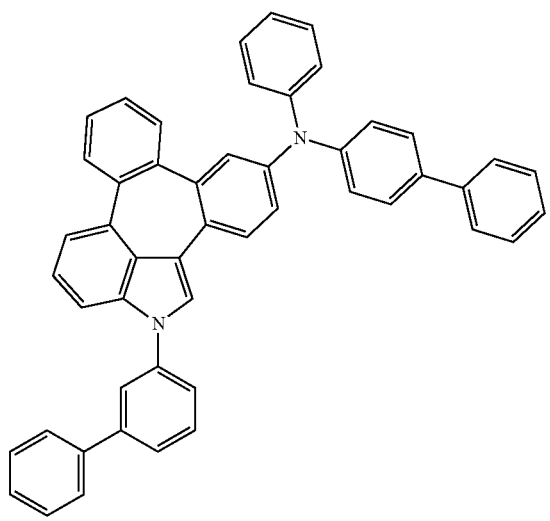
225
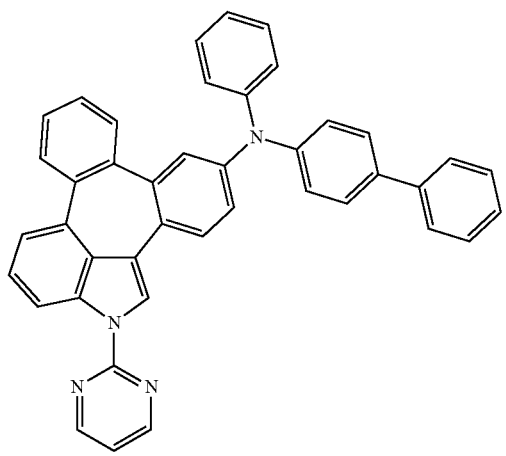
228
226
229
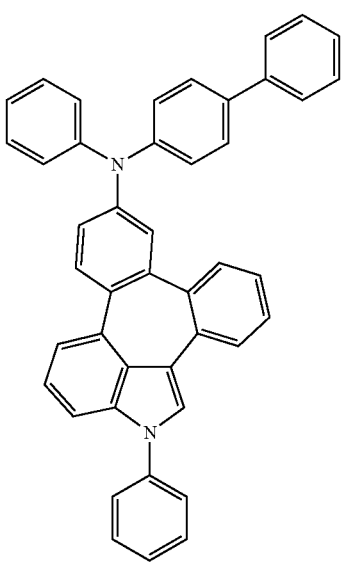
227
230
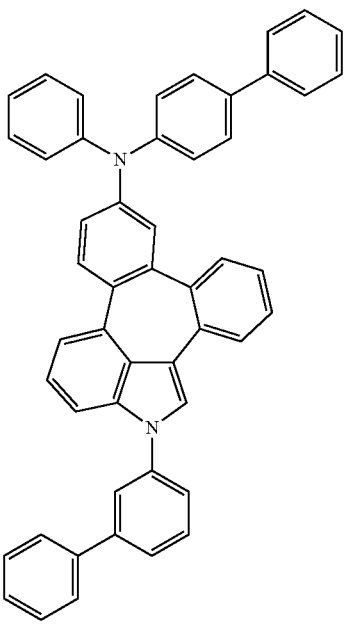

231
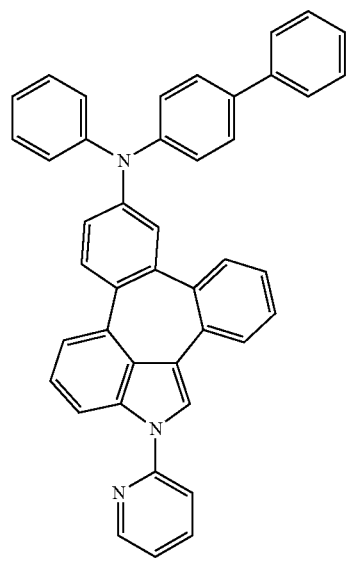
232
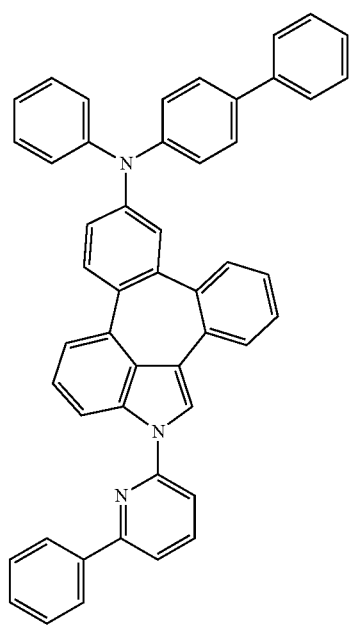
233
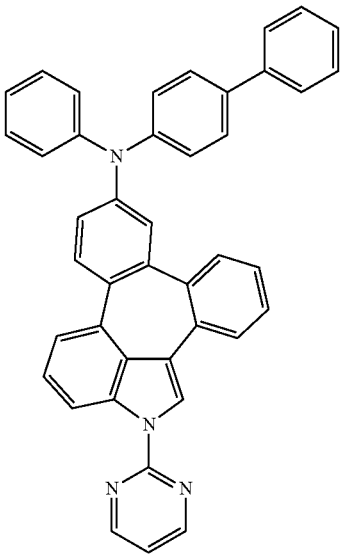
234
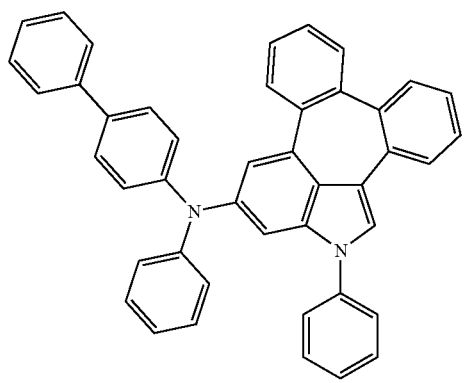
235
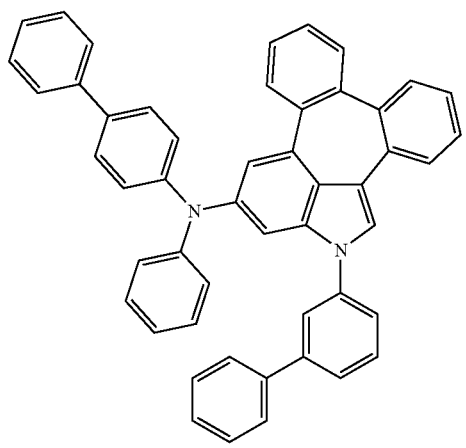

-continued
236
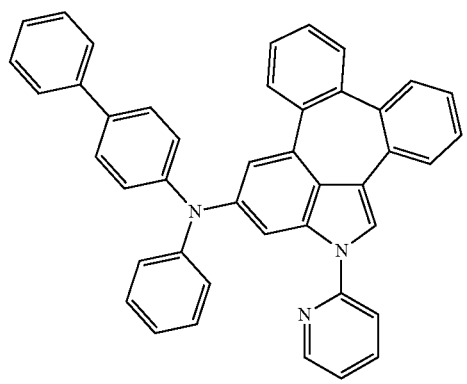
237
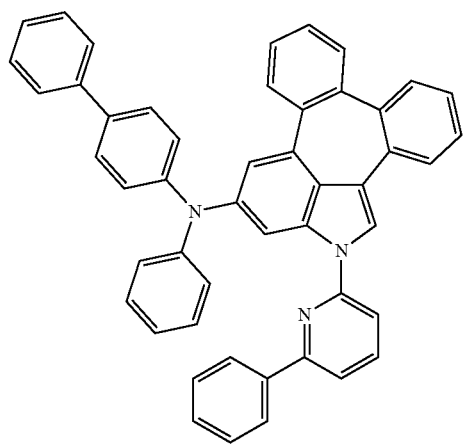
238
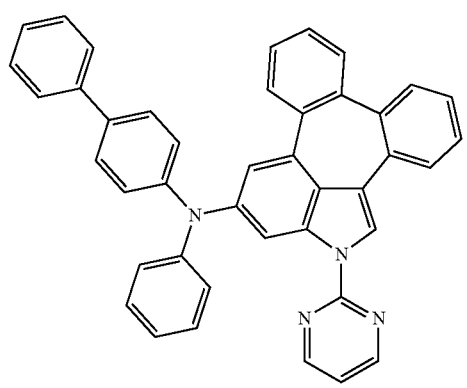
239
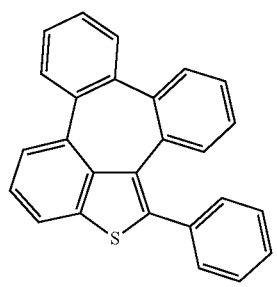
-continued
240
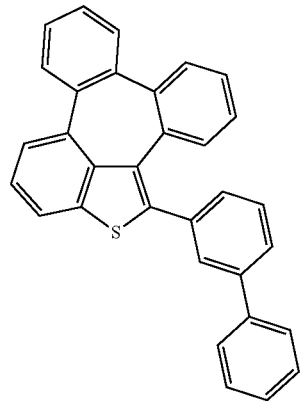
241
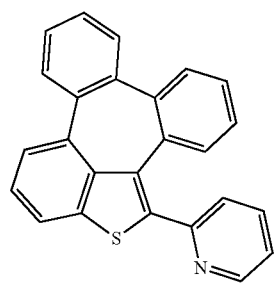
242
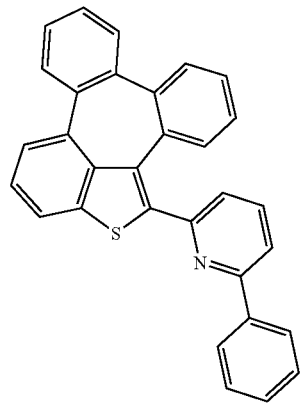
243
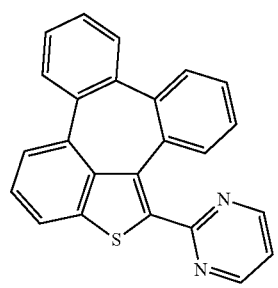

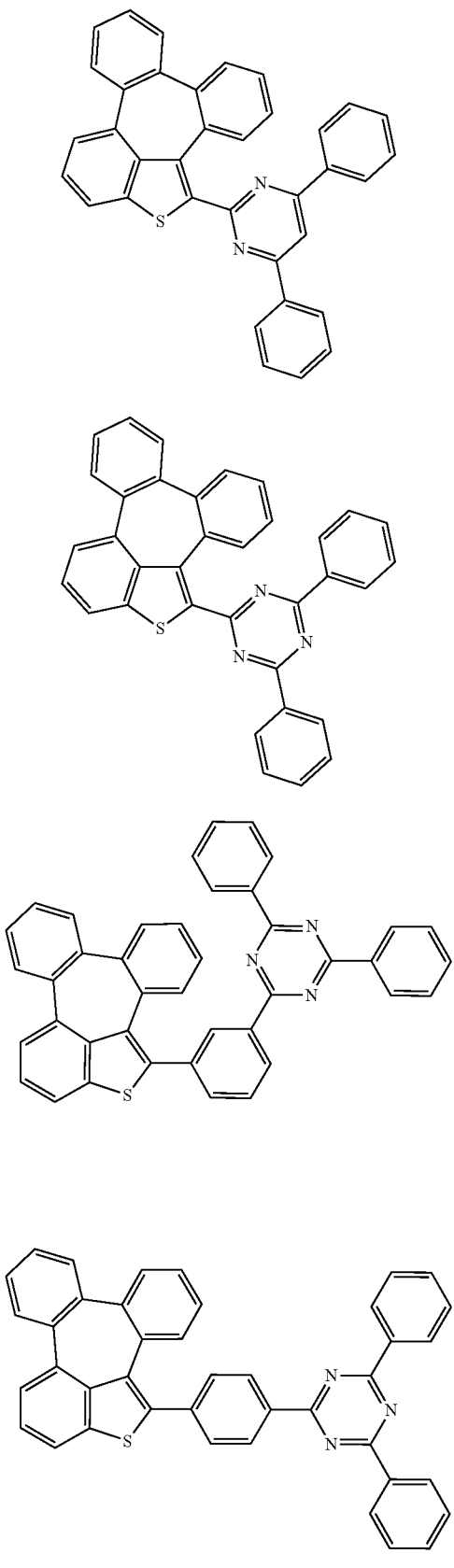
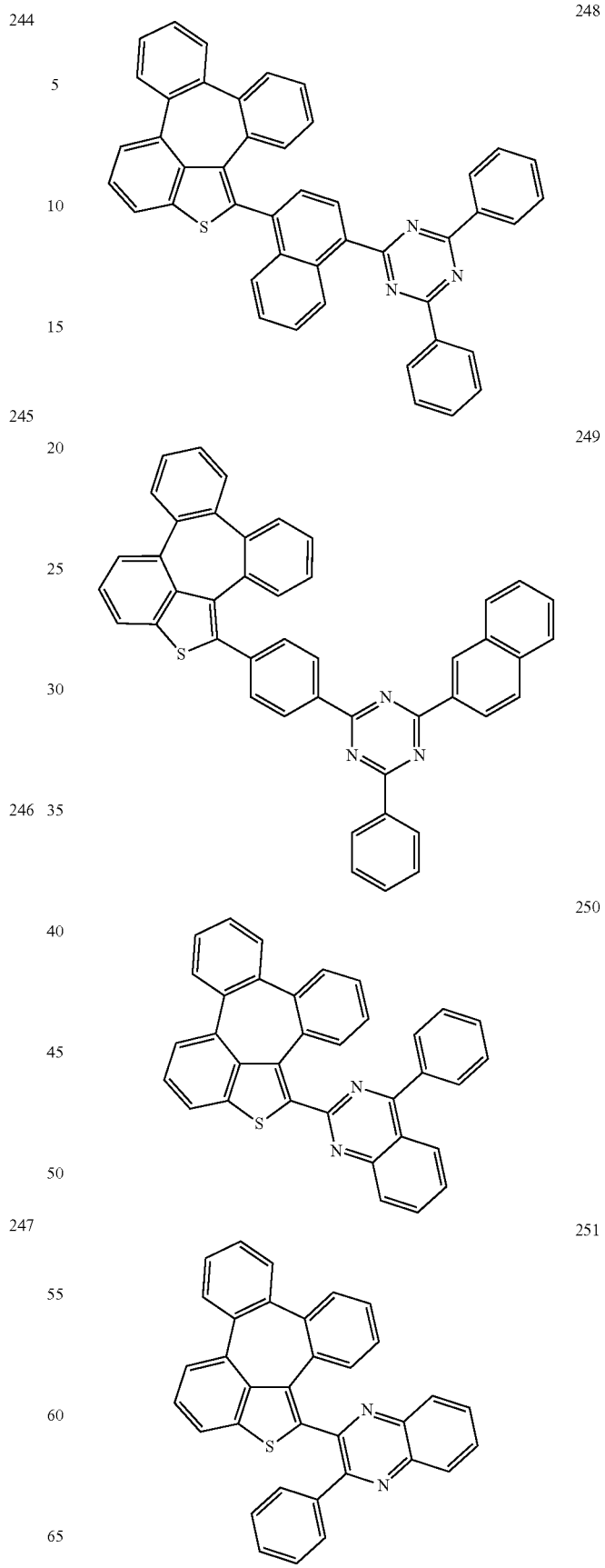

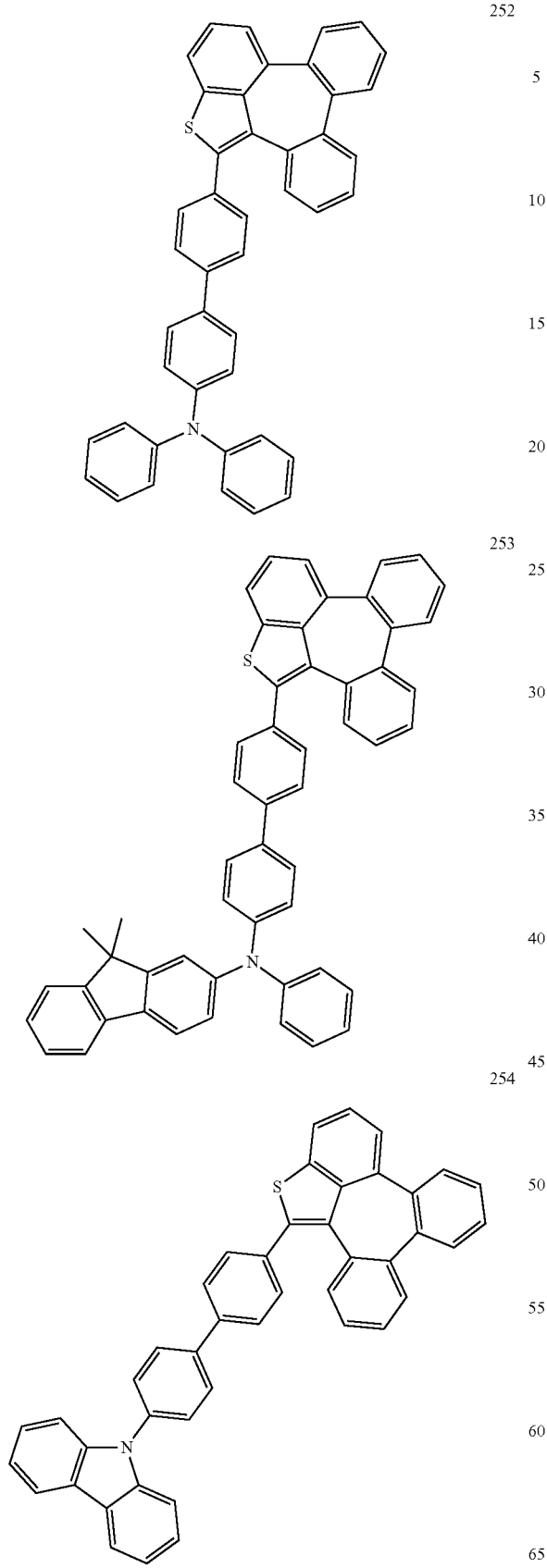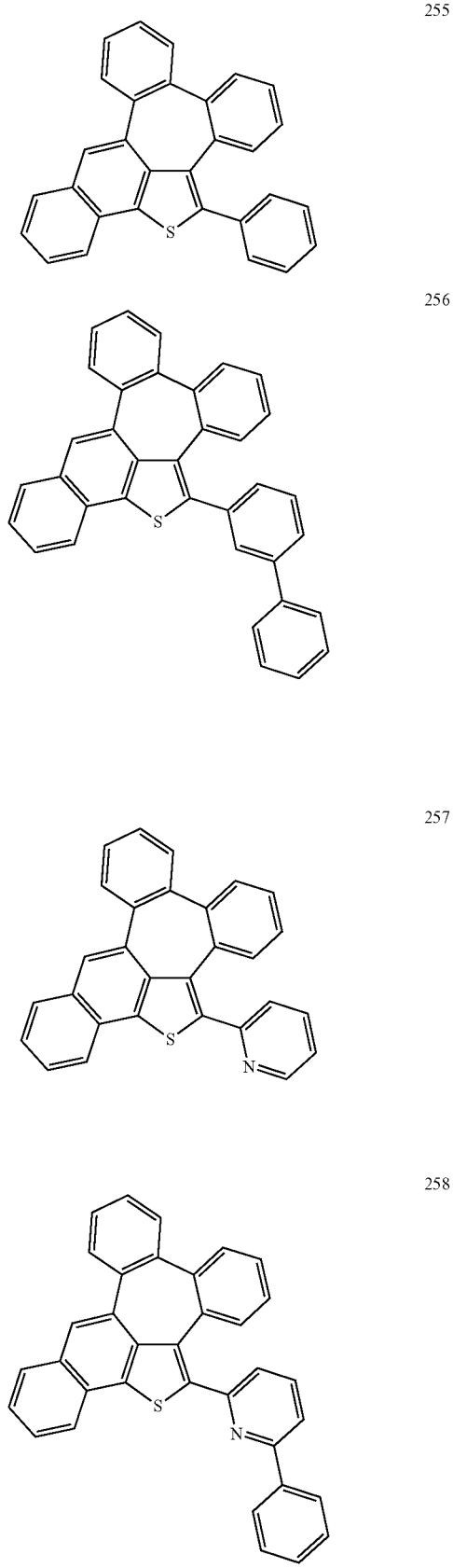

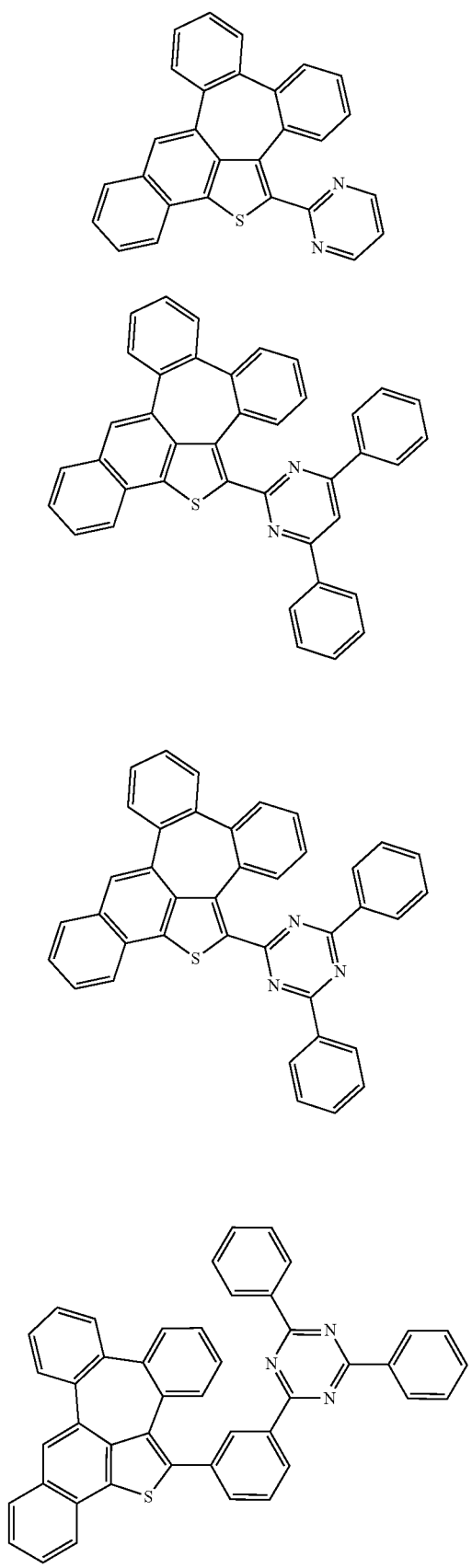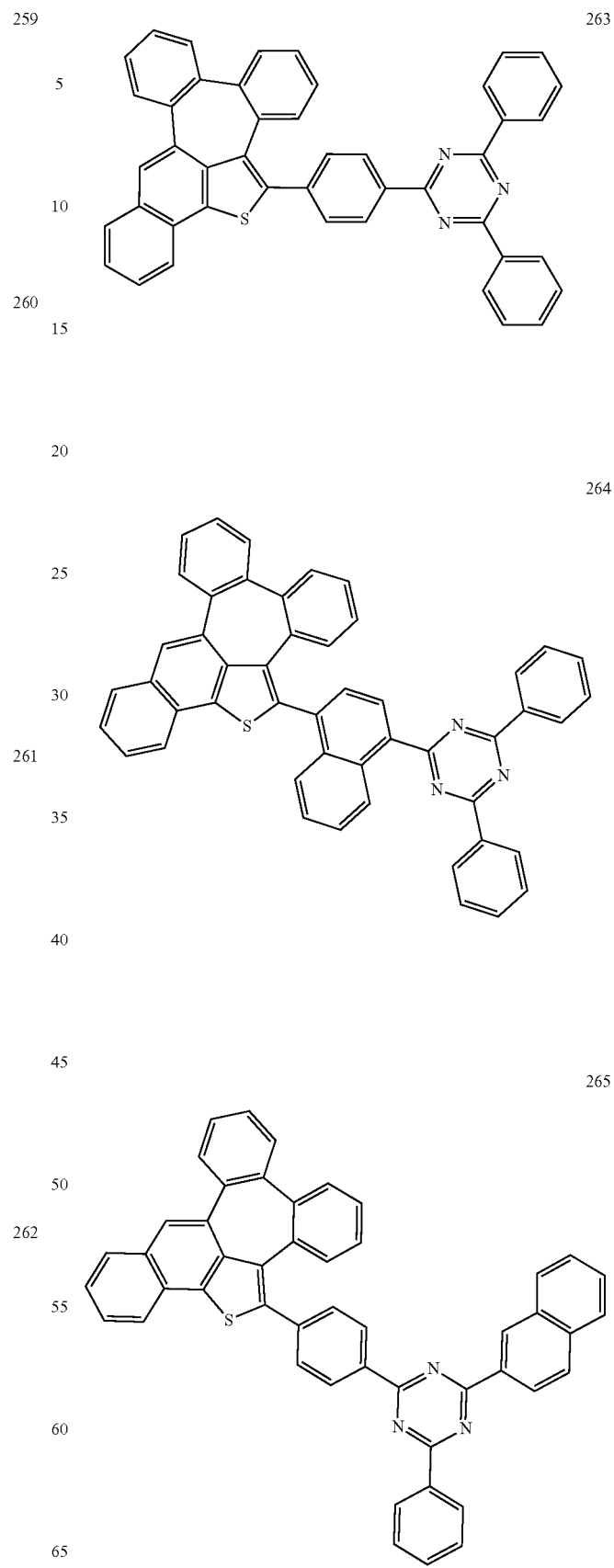

266
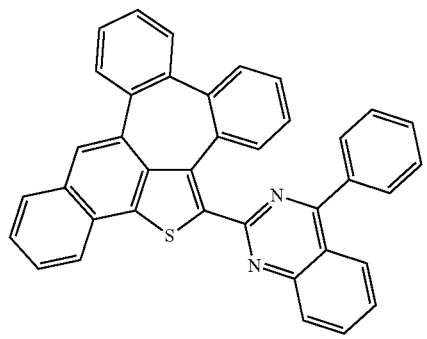
267
269
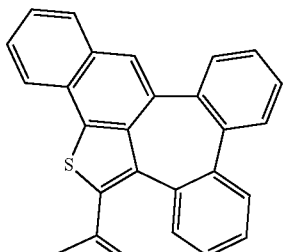
270
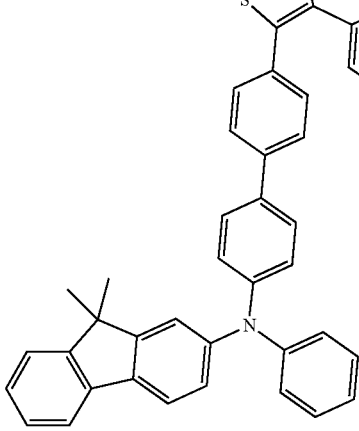
268
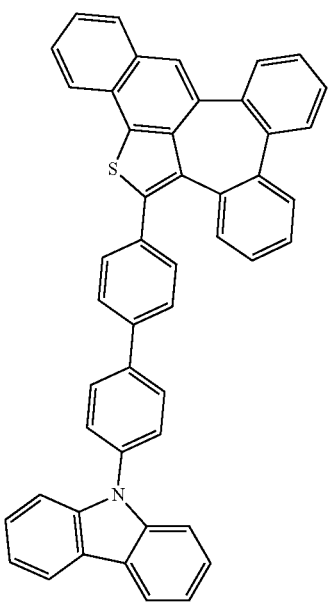
271
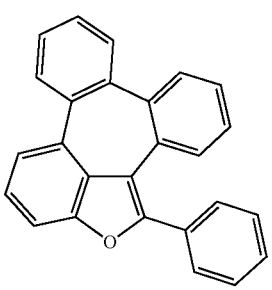

272 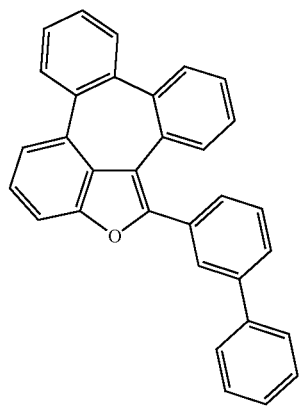
273 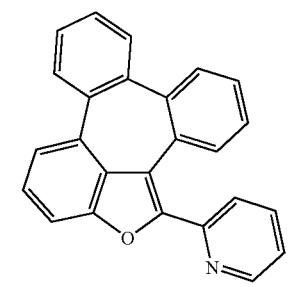
274 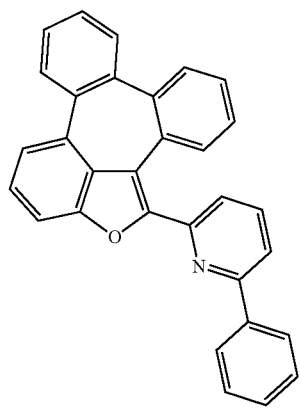
275 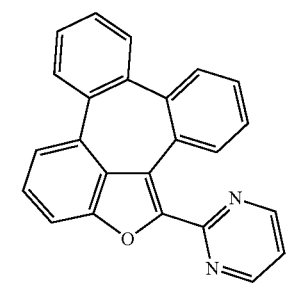
276 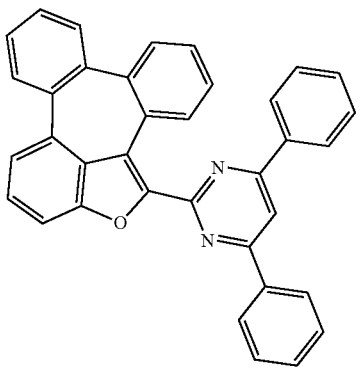
277 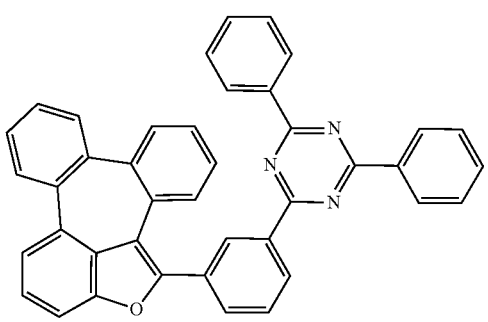
278 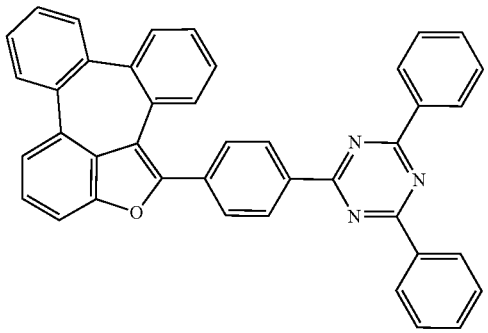
279

280
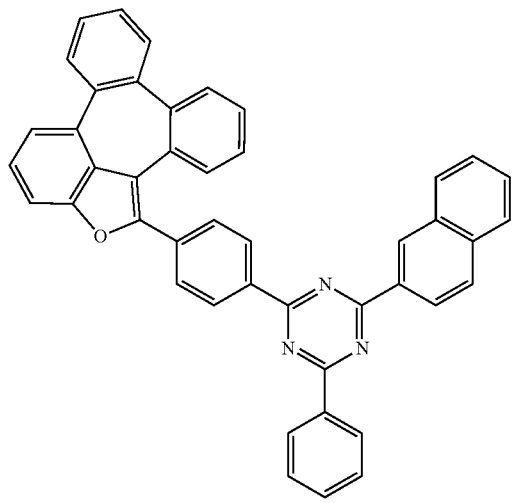
281
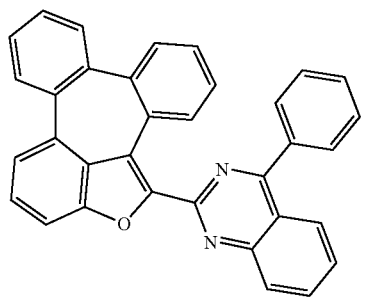
282
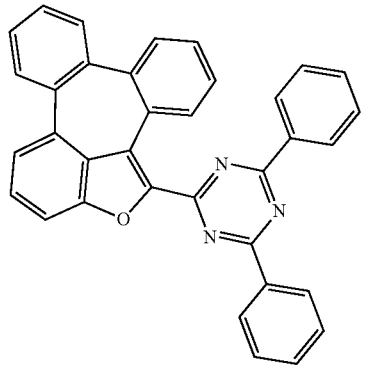
283
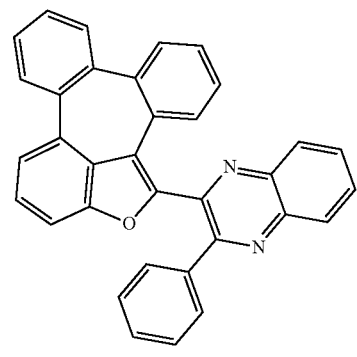
284
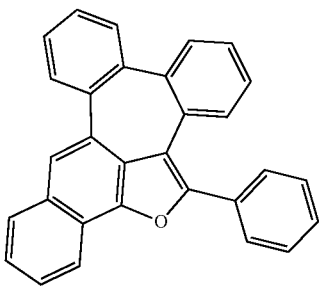
285
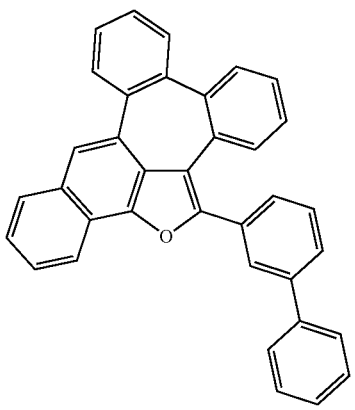
286
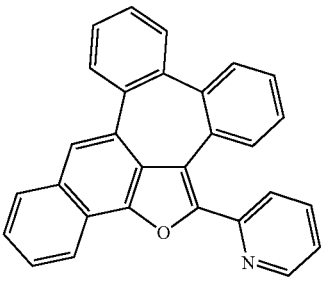
287
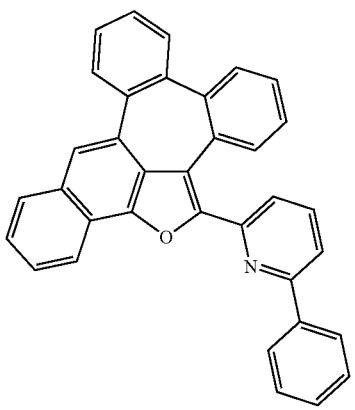

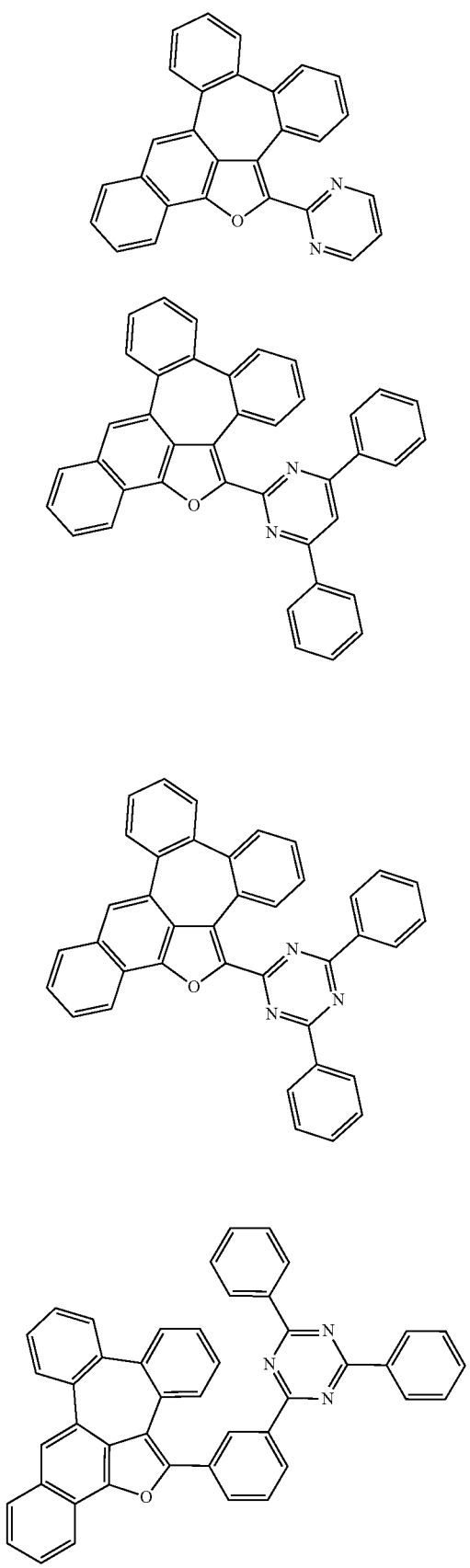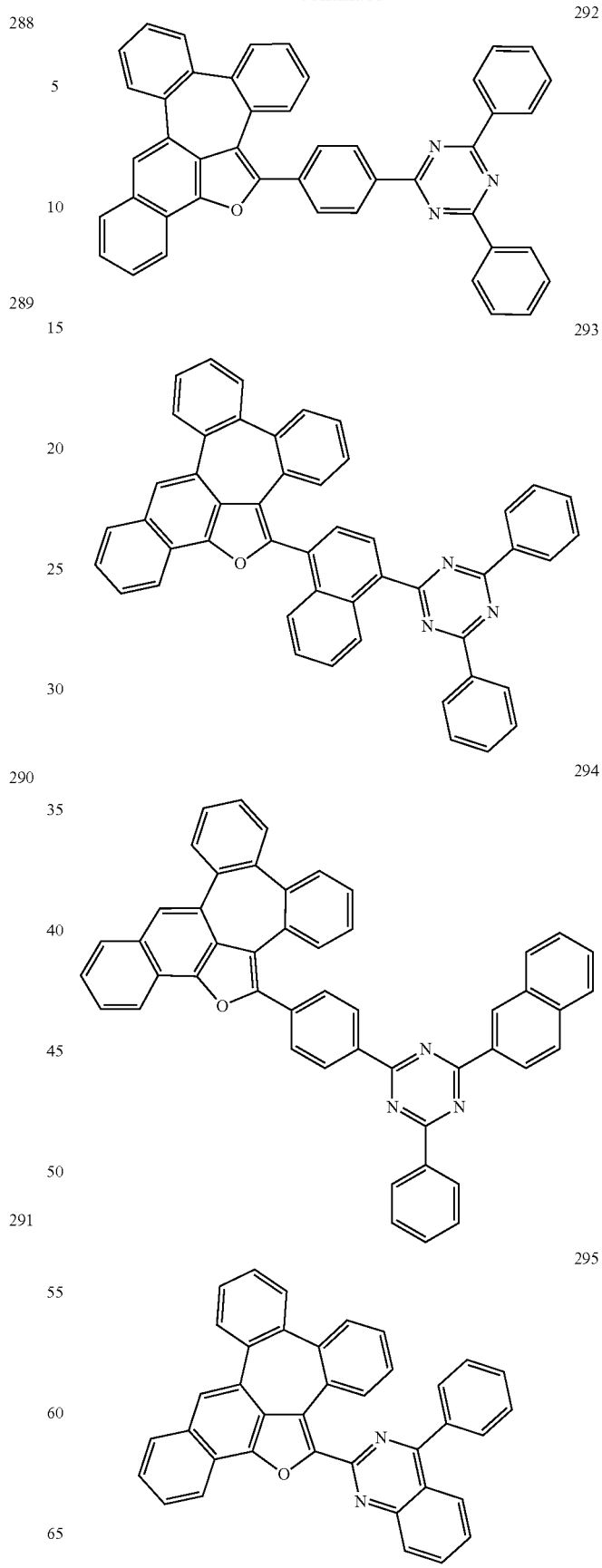

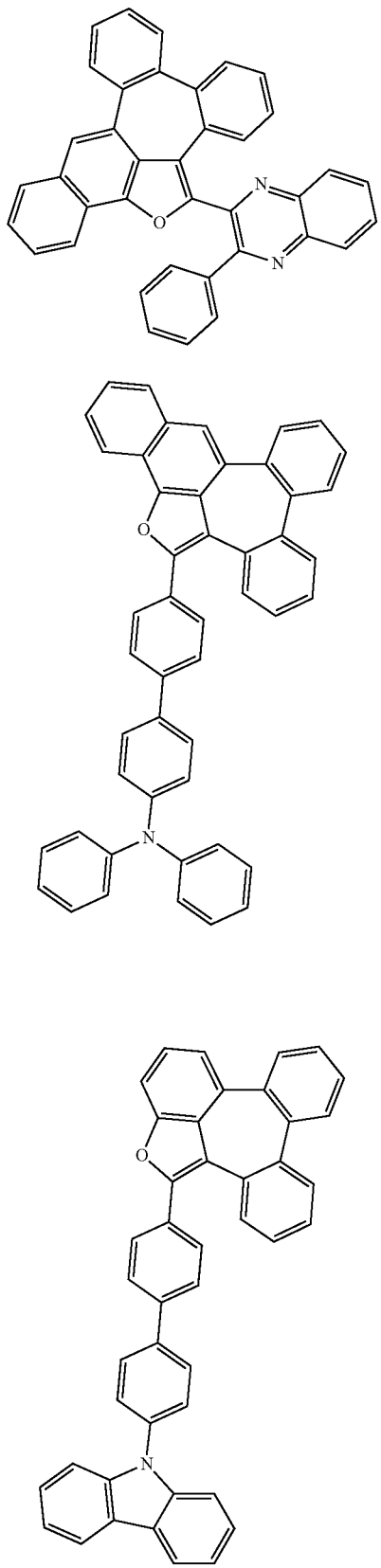
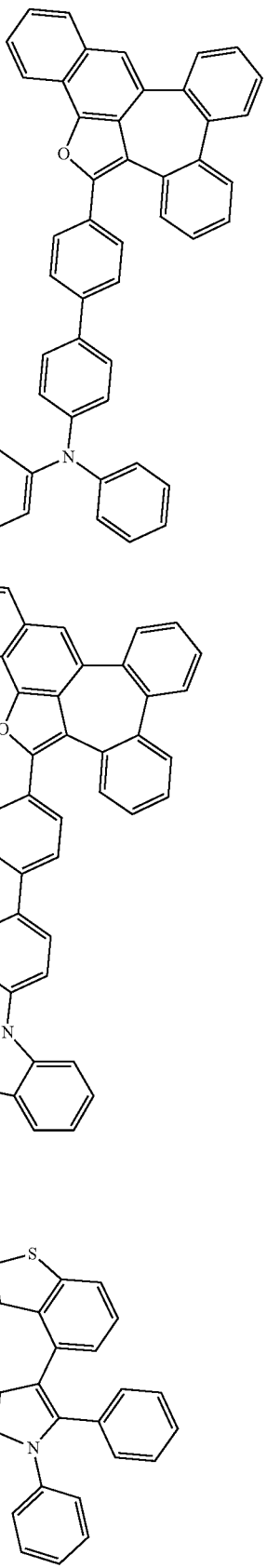

77
-continued
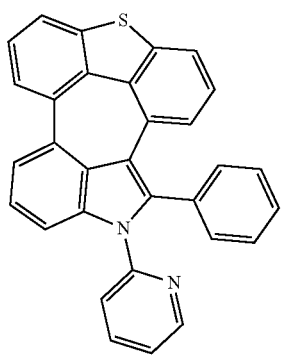
302
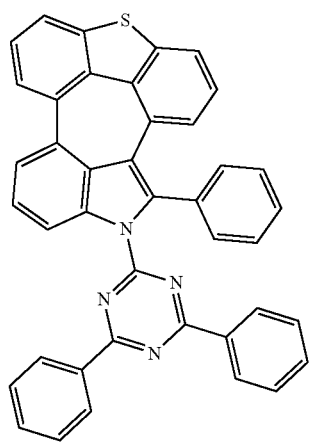
303
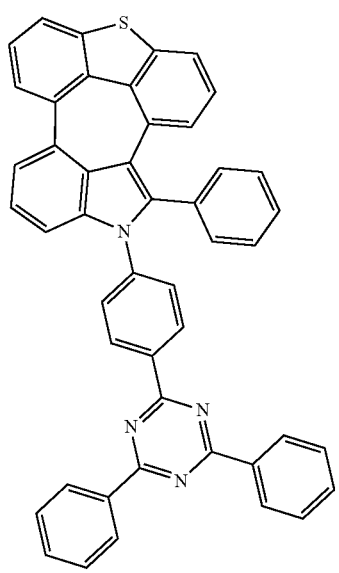
304
78
-continued
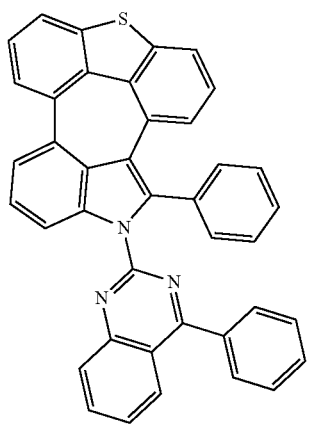
305
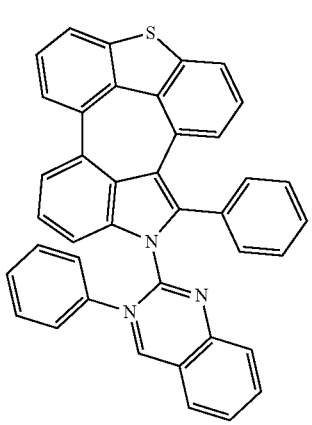
306
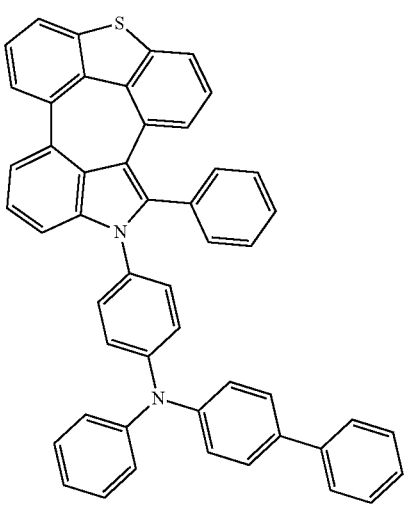
307

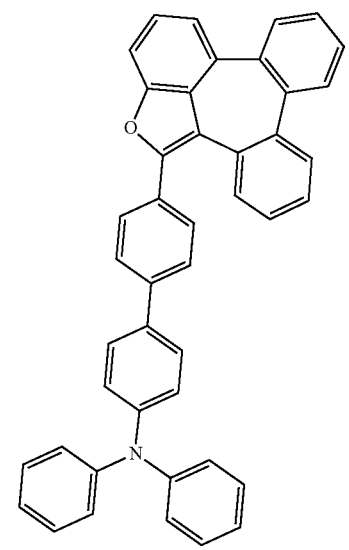
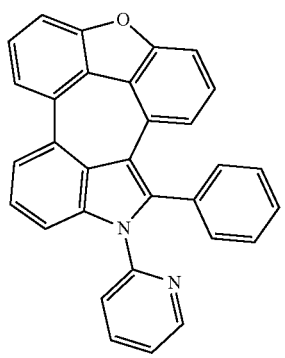
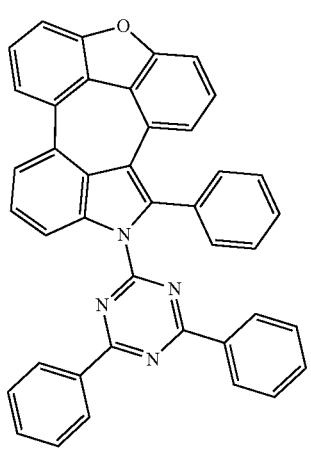
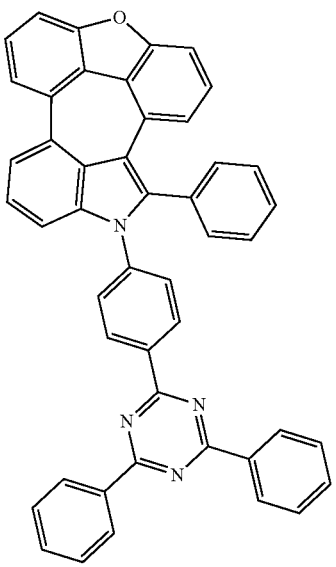

314
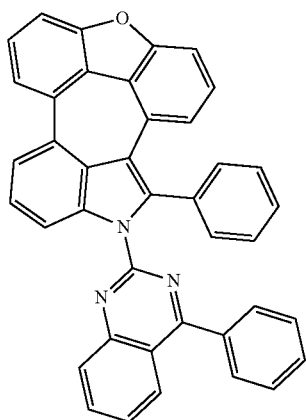
315
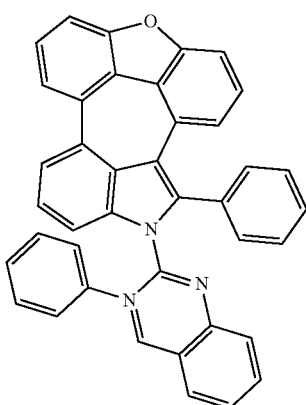
316
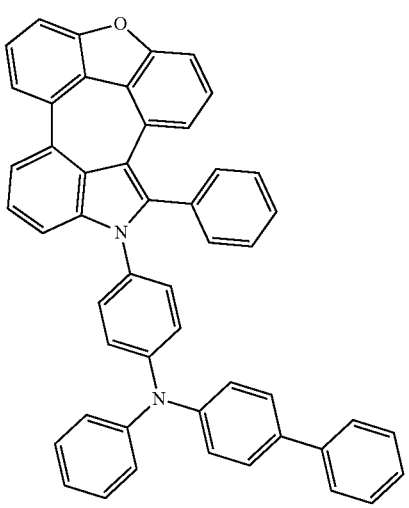
317
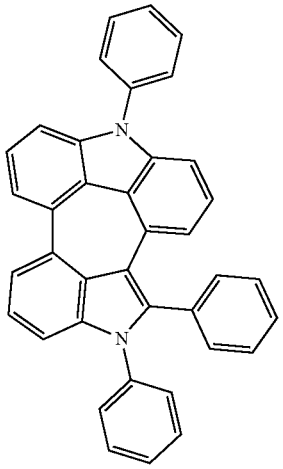
318
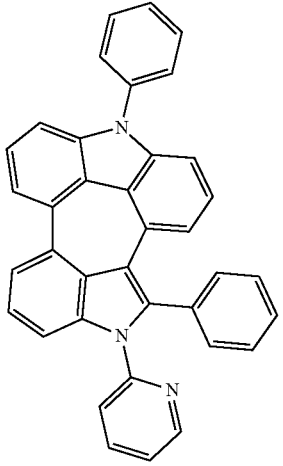
319
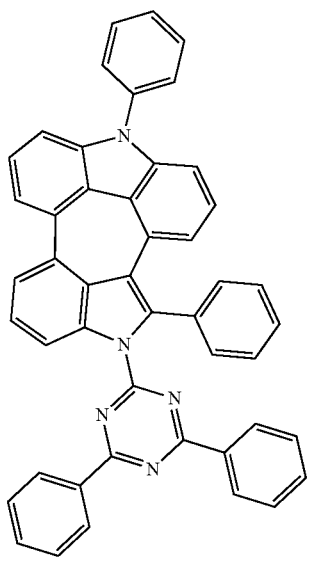

320
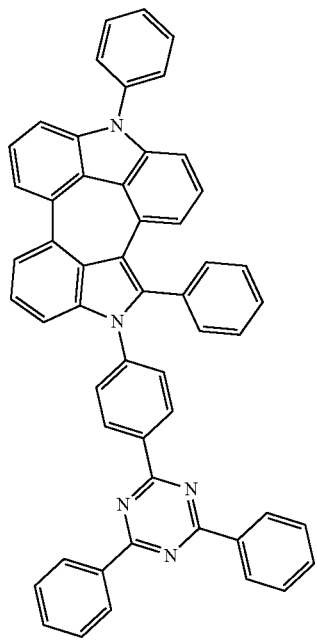
321
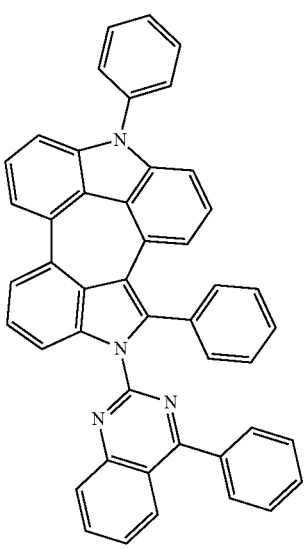
322
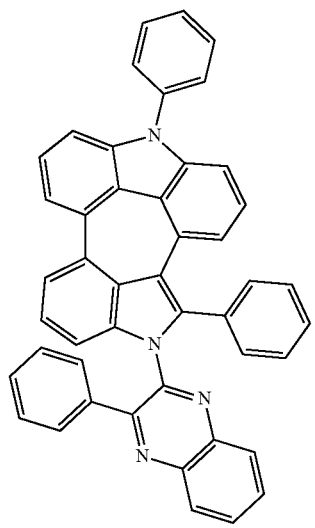
323
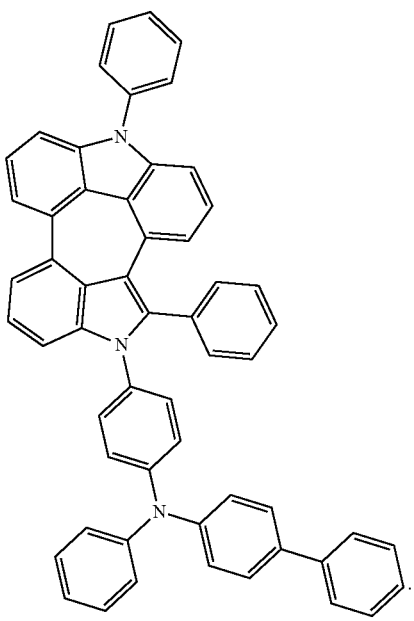
The compounds of formula 1 according to the present disclosure can be prepared by a synthetic method known to one skilled in the art, for example, can be prepared by the following reaction schemes 1 to 3, but is not limited thereto.
[Reaction Scheme 1]
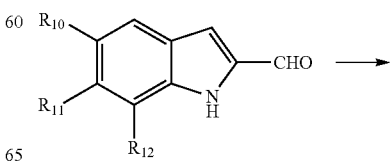

85
-continued
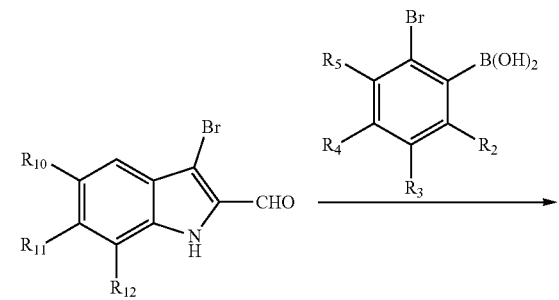
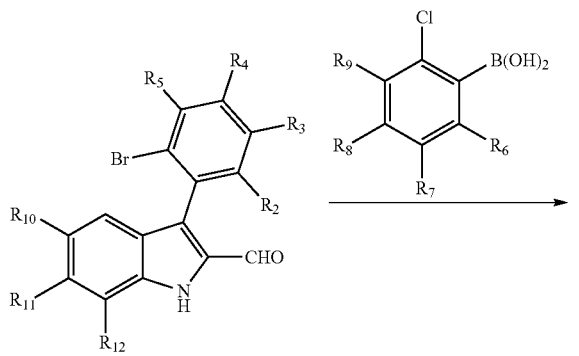
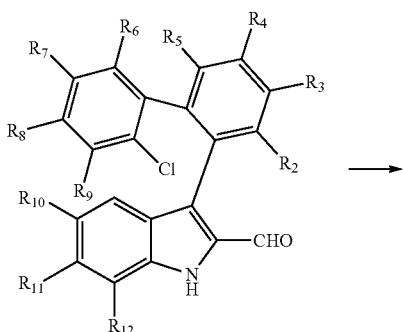
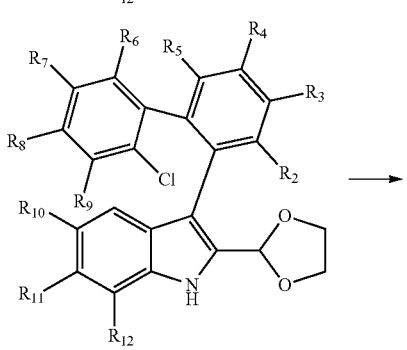
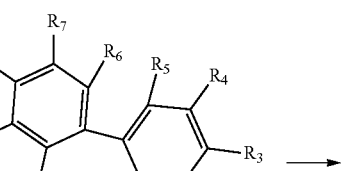
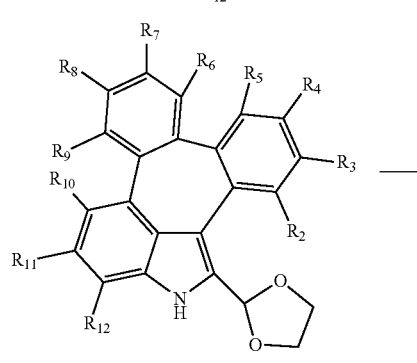
86
-continued
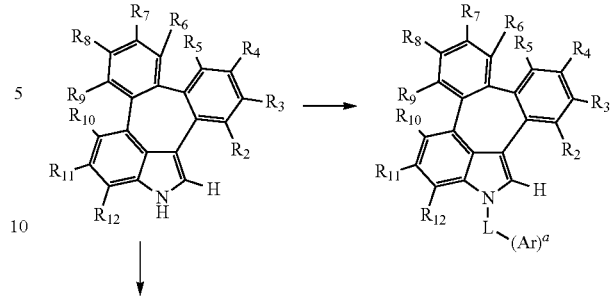
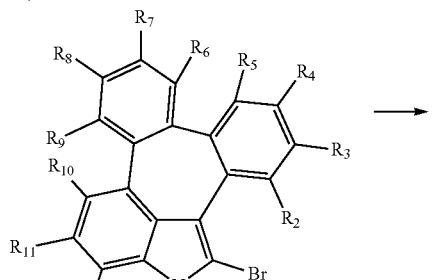
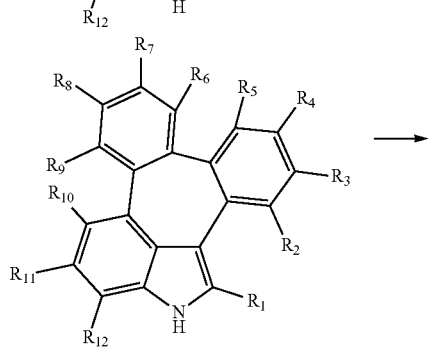
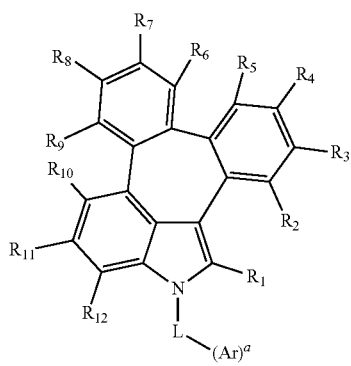
[Reaction Scheme 2]
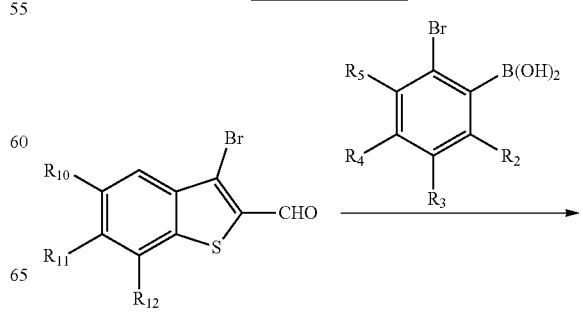

87
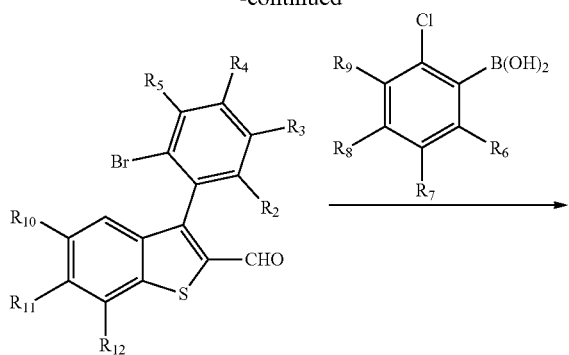
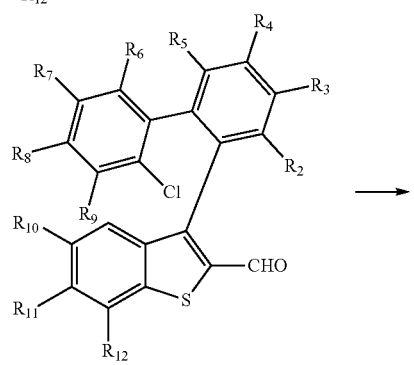
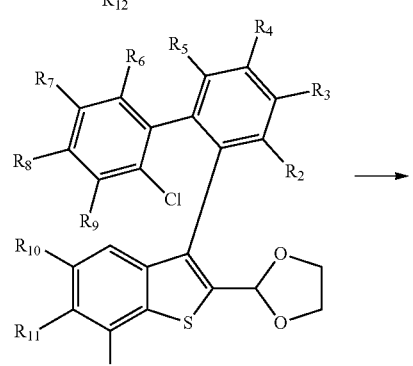
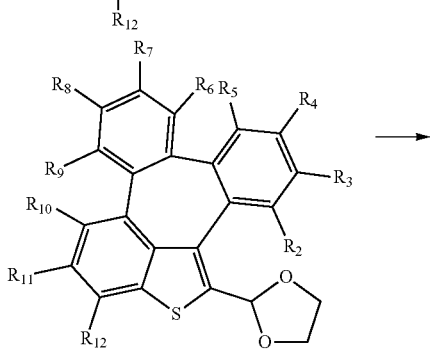
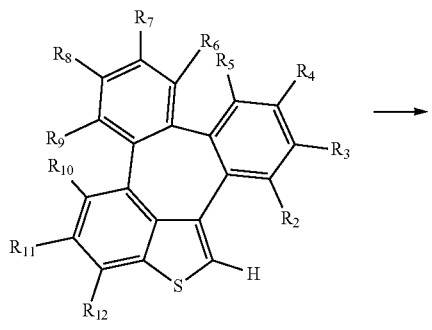
88
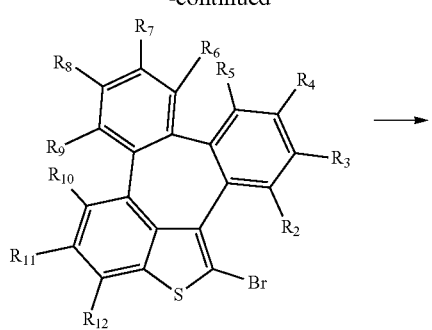
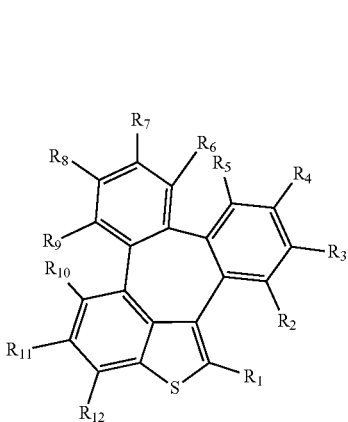
[Reaction scheme 3]
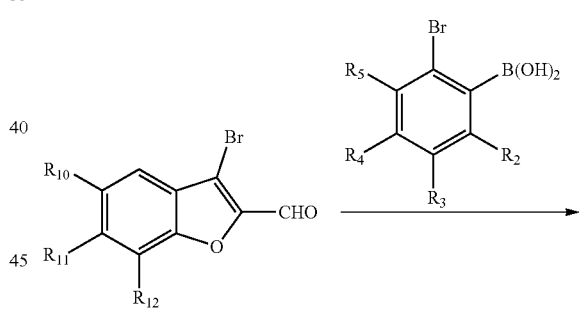
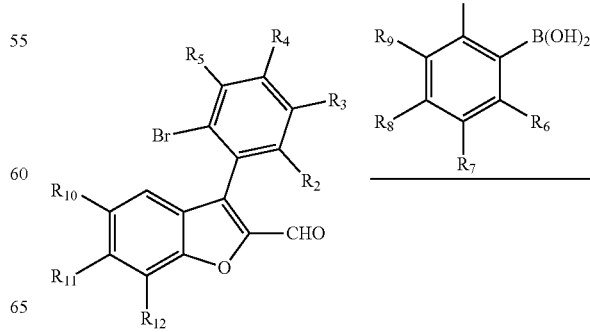

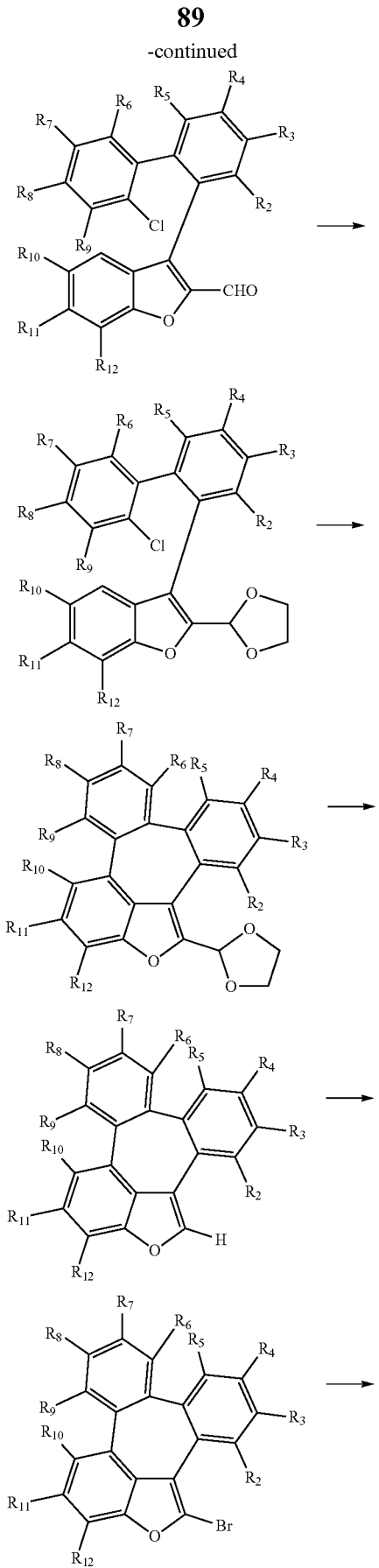

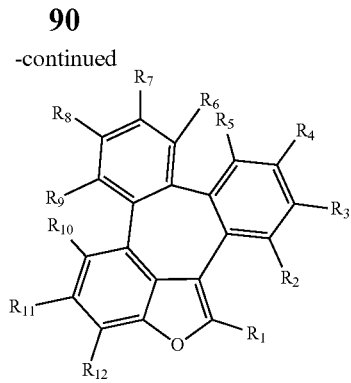

In the reaction schemes 1 to 3, L, Ar, $R_1$, and a are as defined in formula 1, and $R_2$ to $R_{12}$ are as defined in $R_1$.

The present disclosure may provide an organic electroluminescent material comprising an organic electroluminescent compound of formula 1, and an organic electroluminescent device comprising the organic electroluminescent material.

The organic electroluminescent material may consist solely of the organic electroluminescent compound(s) of the present disclosure, or may further comprise conventional materials generally used in organic electroluminescent materials.

The organic electroluminescent compound represented by formula 1 of the present disclosure may be comprised in a hole transport layer (HTL), a light-emitting layer (EML), an electron buffer layer (deposited compound between an electron layer and a light-emitting layer in the deposited device), and an electron transport layer (ETL) etc., preferably, in a light-emitting layer.

Meanwhile, the organic electroluminescent device according to the present disclosure may comprise a first electrode; a second electrode; and at least one organic layer between the first and second electrodes. The organic layer may comprise at least one organic electroluminescent compound of formula 1. In addition, the organic layer may further comprise at least one compound selected from the group consisting of arylamine-based compounds and styrylarylamine-based compounds. Also, the organic layer may further comprise at least one metal selected from the group consisting of metals of Group 1, metals of Group 2, transition metals of the $4^{th}$ period, transition metals of the $5^{th}$ period, lanthanides, and organic metals of the d-transition elements of the Periodic Table, or at least one complex compound comprising the metal.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron injection layer, an interlayer, a hole blocking layer, an electron blocking layer, and an electron buffer layer.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. The electron blocking layer may be placed between the hole transport layer (or the hole injection layer) and the light-emitting layer, and can confine the excitons within the light-emitting layer by blocking the overflow of electrons from the light-emitting layer to prevent light-emitting leakage. The hole transport layer or the electron blocking layer may also be formed of multi-layers, wherein each of the multi-layers may use a plurality of compounds.

An electron buffer layer, a hole blocking layer, an electron transport layer, or an electron injection layer, or a combination thereof can be used between the light-emitting layer and the cathode. The electron buffer layer may be multi-layers in order to control the injection of the electrons and enhance the interfacial characteristics between the light-emitting layer and the electron injection layer, wherein each of the multi-layers may use two compounds simultaneously. The hole blocking layer or the electron transport layer may also be formed of multi-layers, and each layer can may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. Also, the hole auxiliary layer may be placed between the hole transport layer (or hole injection layer) and the light-emitting layer, and may be effective to promote or block the hole transport rate (or the hole injection rate), thereby enabling the charge balance to be controlled. When an organic electroluminescent device includes two or more hole transport layers, the hole transport layer, which is further included, may be used as a hole auxiliary layer or an electron blocking layer. The light-emitting auxiliary layer, the hole auxiliary layer or the electron blocking layer may have an effect of improving the efficiency and/or the lifespan of the organic electroluminescent device.

In the organic electroluminescent device of the present disclosure, preferably, at least one layer (hereinafter, "a surface layer") selected from a chalcogenide layer, a metal halide layer, and a metal oxide layer may be placed on at least one of an inner surface(s) of a pair of electrodes. Specifically, a chalcogenide (including oxides) layer of silicon and aluminum is preferably placed on an anode surface of a light-emitting medium layer, and a metal halide layer or a metal oxide layer is preferably placed on a cathode surface of a light-emitting medium layer. The operation stability for the organic electroluminescent device may be obtained by the surface layer. Preferably, the chalcogenide includes $SiO_x(1 \leq X \leq 2)$, $AlO_x(1 \leq X \leq 1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In addition, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the light-emitting medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an organic electroluminescent device having two or more light-emitting layers and emitting white light.

The compound of the present disclosure represented by formula 1 may be comprised in the light-emitting layer. When used in the light-emitting layer, the organic electroluminescence compound of formula 1 may be comprised as a host material. Preferably, the light-emitting layer may further comprise at least one dopant. If necessary, the compound other than the organic electroluminescent compound represented by formula 1 of the present disclosure may be further comprised as a second host material. Herein, the weight ratio of the first host material to the second host material is in the range of 1:99 to 99:1. Any of the known phosphorescent hosts are available for use as the second host material.

The dopant comprised in the organic electroluminescent device of the present disclosure is preferably at least one phosphorescent dopant. The phosphorescent dopant material comprised in the organic electroluminescent device of the present disclosure is not particularly limited, but may be preferably selected from metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant comprised in the organic electroluminescent device according to the present disclosure may use at least one selected from the compounds represented by the following formulae 101 to 104, but is not limited thereto.

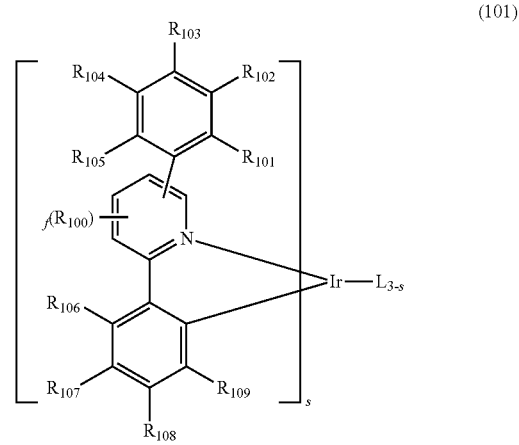

(101)

-continued (102)
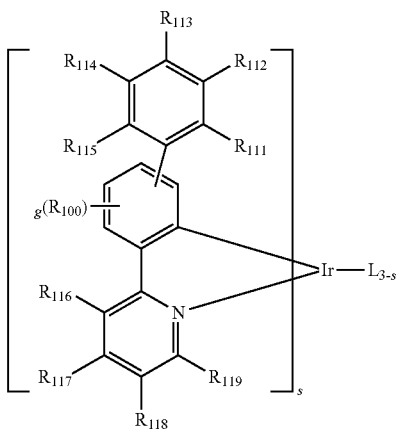

(103)
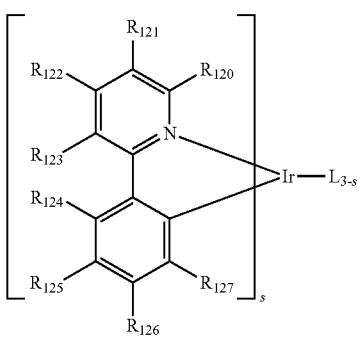

(104)
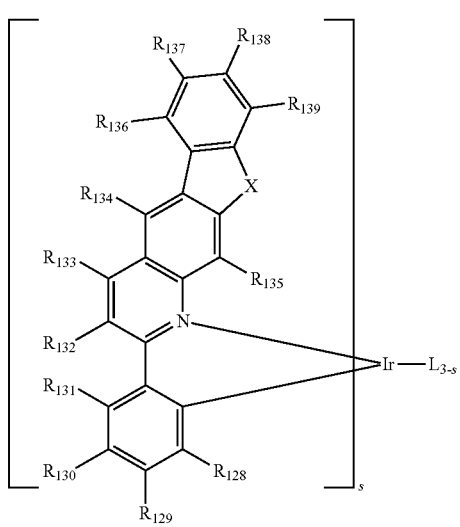

wherein,
L is selected from the following structures:

(structure 1)
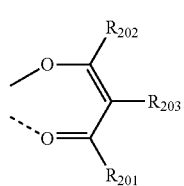

(structure 2)

$R_{100}$, $R_{134}$, and $R_{135}$ each independently, represent hydrogen, deuterium, a substituted or unsubstituted (C1-C30)alkyl, or a substituted or unsubstituted (C3-C30)cycloalkyl;

$R_{101}$ to $R_{109}$, and $R_{111}$ to $R_{123}$ each independently, represent hydrogen, deuterium, halogen, a (C1-C30)alkyl unsubstituted or substituted with deuterium or halogen, a substituted or unsubstituted (C3-C30)cycloalkyl, a substituted or unsubstituted (C6-C30)aryl, cyano, or a substituted or unsubstituted (C1-C30)alkoxy, where $R_{106}$ to $R_{109}$ may be linked to adjacent $R_{106}$ to $R_{109}$ to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl; and $R_{120}$ to $R_{123}$ may be linked to adjacent $R_{120}$ to $R_{123}$ to form a substituted or unsubstituted fused ring, e.g., a quinoline unsubstituted or substituted with at least one selected from an alkyl, an aryl, an aralkyl, and an alkylaryl;

$R_{124}$ to $R_{133}$ and $R_{136}$ to $R_{139}$, each independently, represent hydrogen, deuterium, halogen, a substituted or unsubstituted (C1-C30)alkyl, or a substituted or unsubstituted (C6-C30)aryl, where $R_{124}$ to $R_{127}$ may be linked to adjacent $R_{124}$ to $R_{127}$ to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl;

X represents $CR_{11}R_{12}$, O, or S;

$R_{11}$ and $R_{12}$, each independently, represent a substituted or unsubstituted (C1-C10)alkyl, or a substituted or unsubstituted (C6-C30)aryl;

$R_{201}$ to $R_{211}$, each independently, represent hydrogen, deuterium, halogen, a (C1-C30)alkyl unsubstituted or substituted with deuterium or halogen, a substituted or unsubstituted (C3-C30)cycloalkyl, or a (C6-C30)aryl unsubstituted or substituted with an alkyl or deuterium, where $R_{208}$ to $R_{211}$ may be linked to adjacent $R_{208}$ to $R_{211}$ to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl;

f and g, each independently, represent an integer of 1 to 3; where if f or g is an integer of 2 or more, each $R_{100}$ may be the same or different; and s represents an integer of 1 to 3.

Specifically, the dopant material may be more specifically illustrated as follows, but is not limited thereto:

D-1 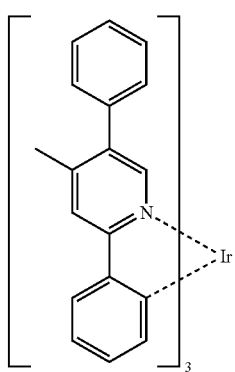
D-2 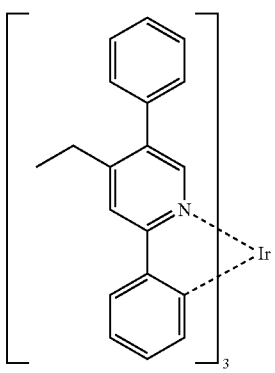
D-3 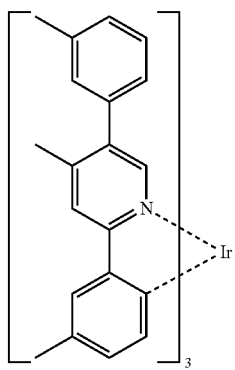
D-4 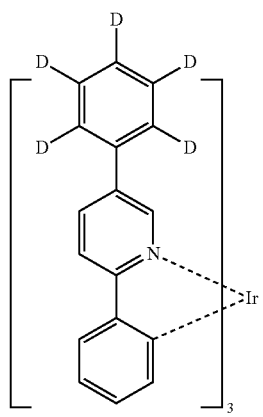
-continued
D-5 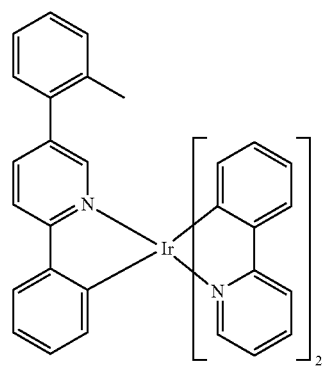
D-6 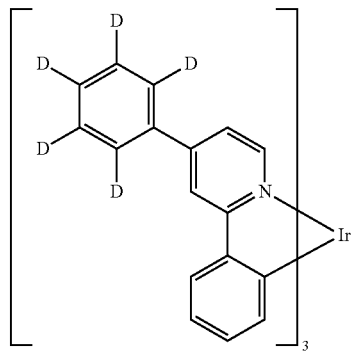
D-7 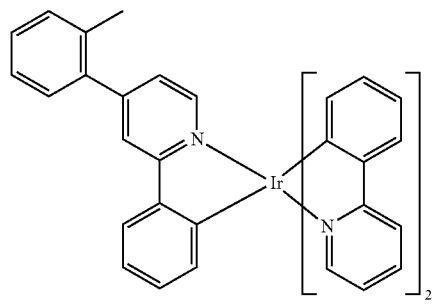
D-8 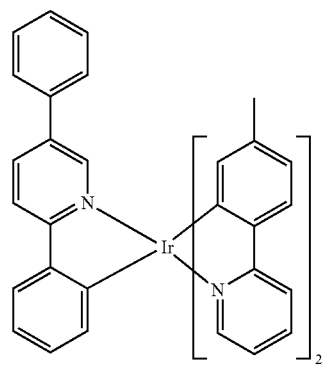

D-9
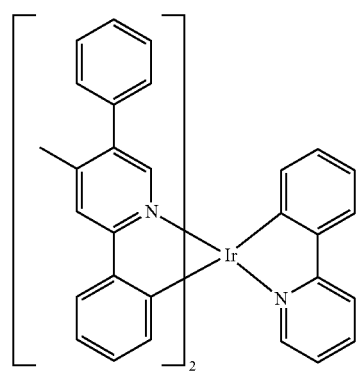
D-10
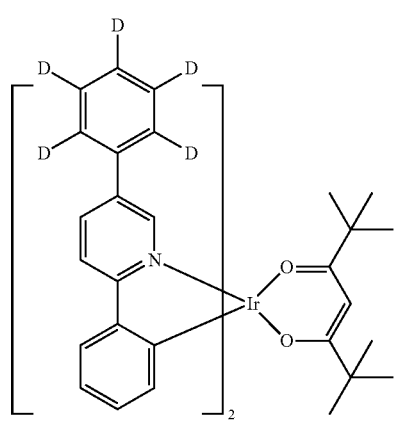
D-11
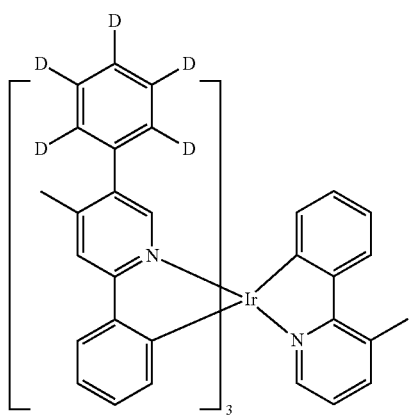
D-12
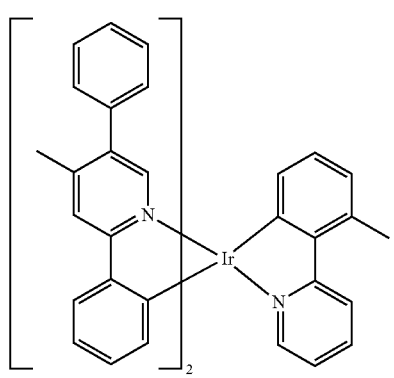
D-13
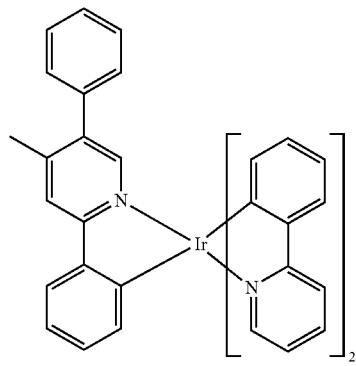
D-14
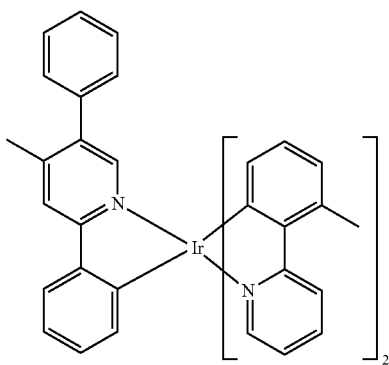
D-15
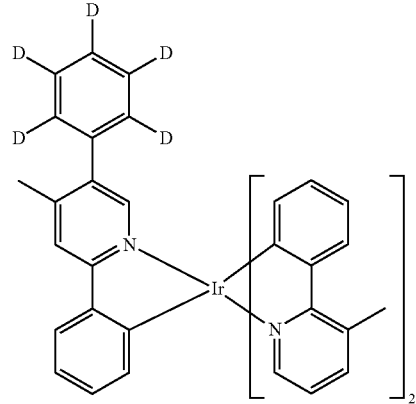
D-16
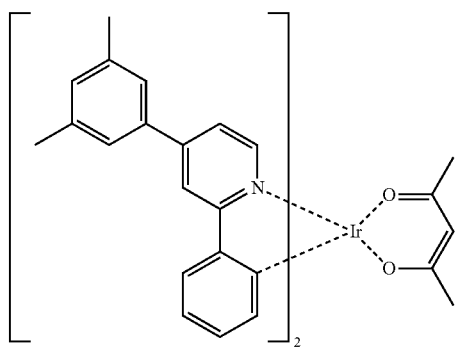

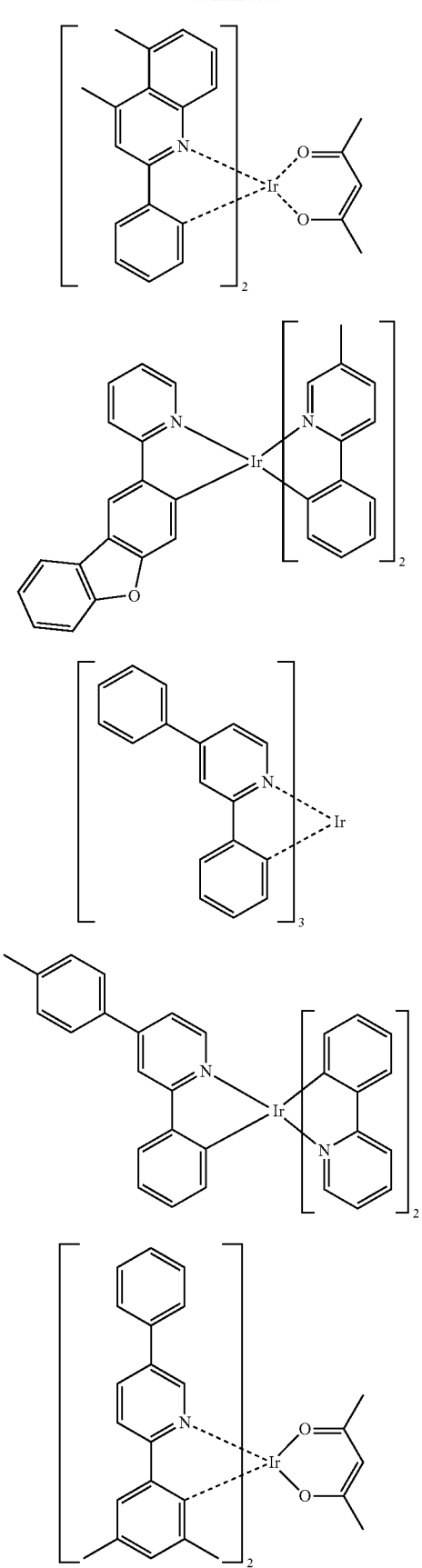
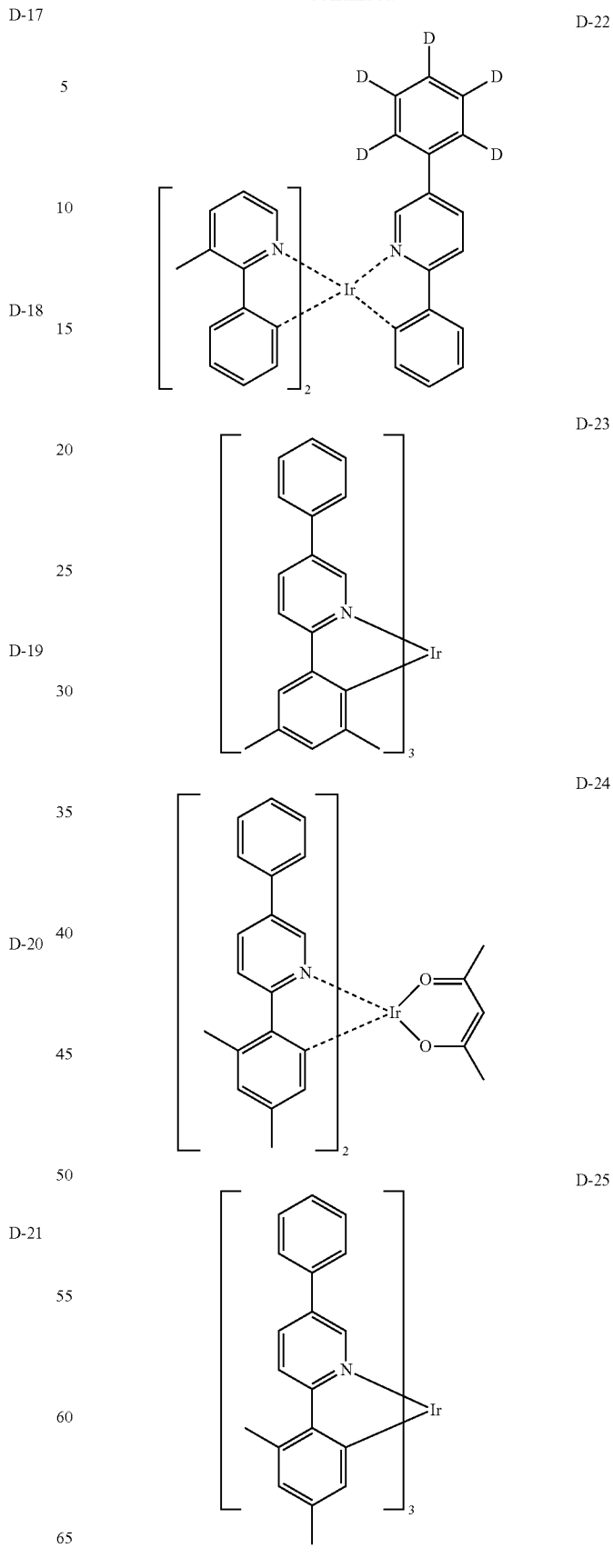

-continued
D-26
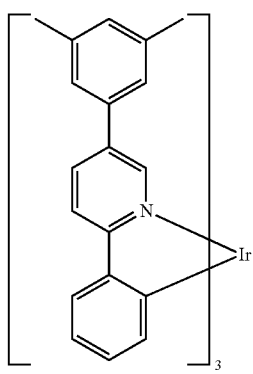
D-27
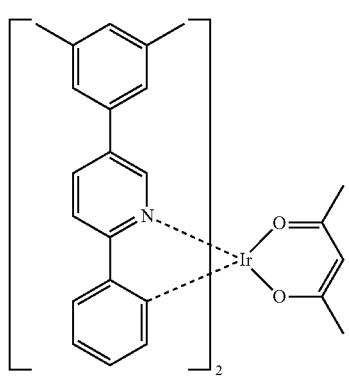
D-28
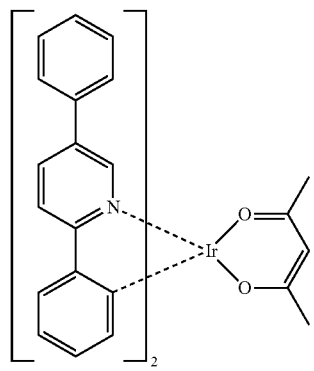
D-29
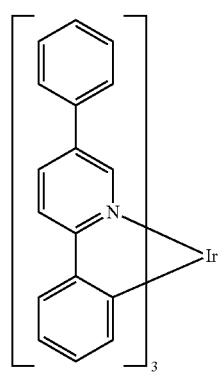
-continued
D-30
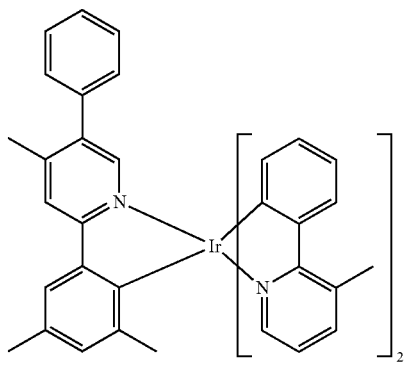
D-31
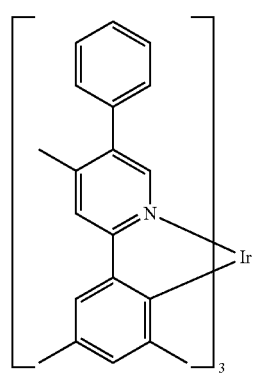
D-32
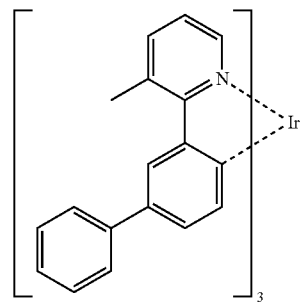
D-33
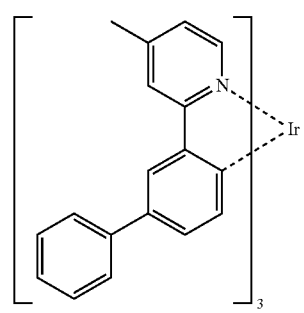

-continued
D-34
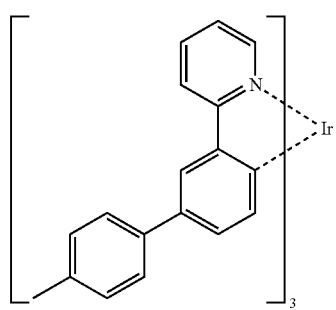
D-35
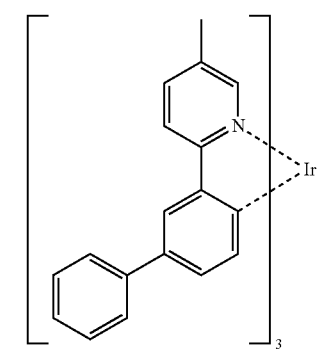
D-36
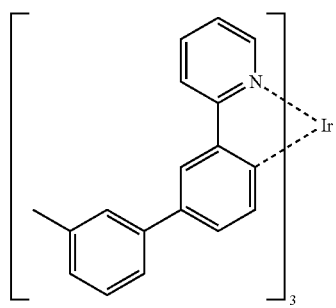
D-37
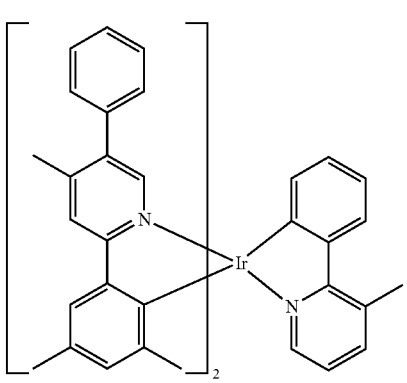
-continued
D-38
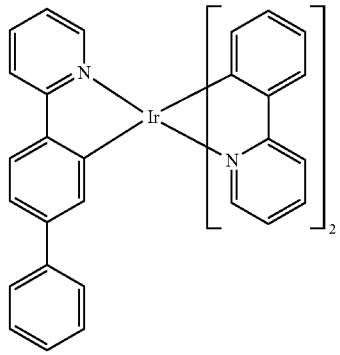
D-39
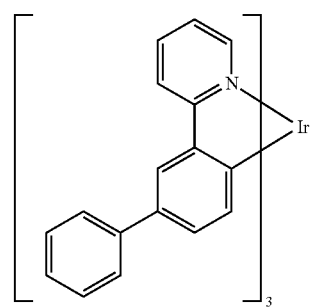
D-40
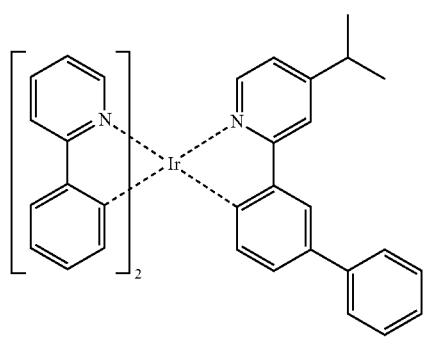
D-41
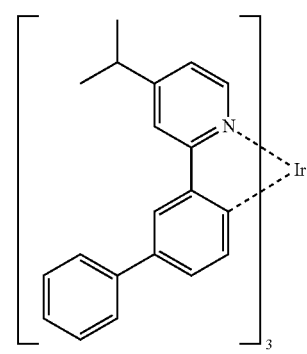
D-42
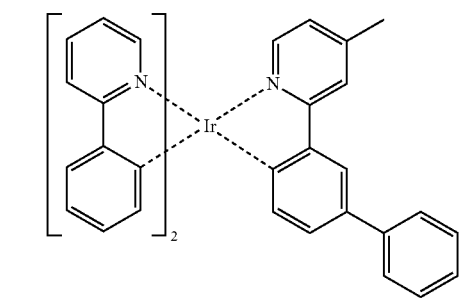

D-43
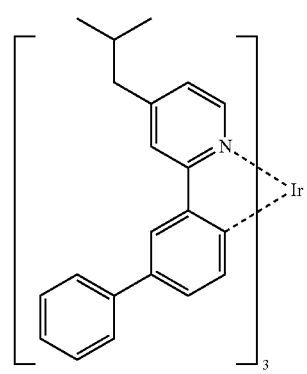
D-44
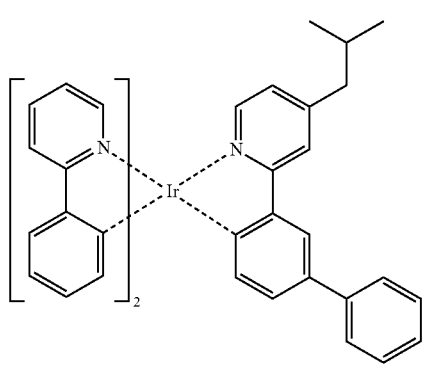
D-45
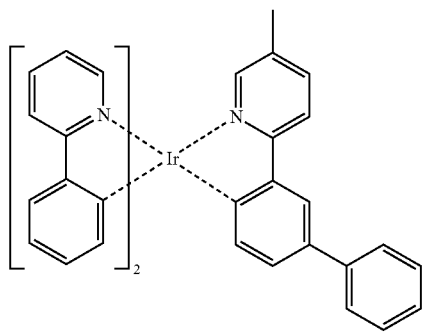
D-46
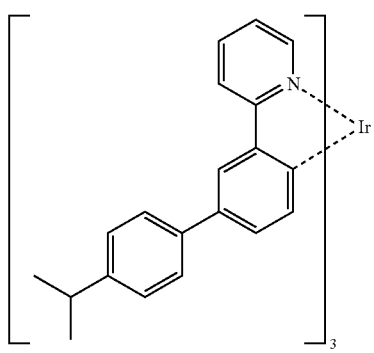
D-47
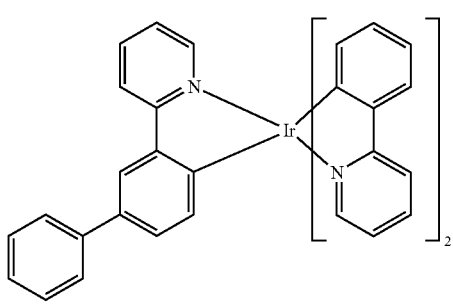
D-48
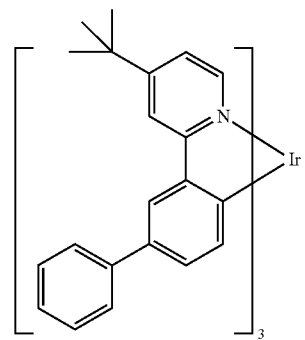
D-49
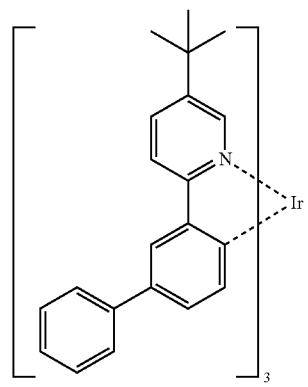
D-50
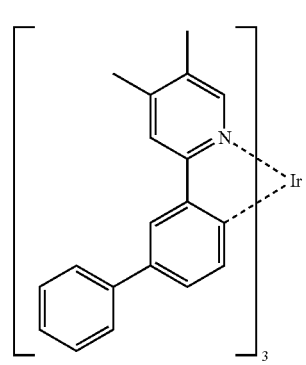

D-51
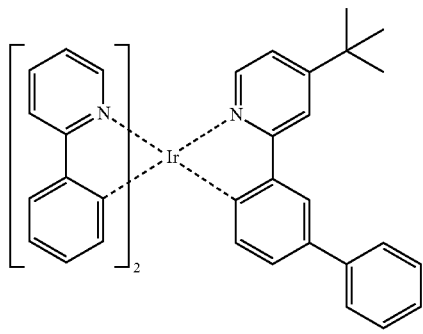
D-52
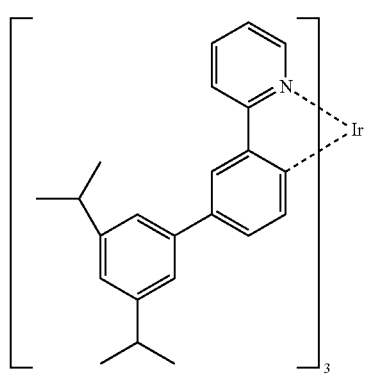
D-53
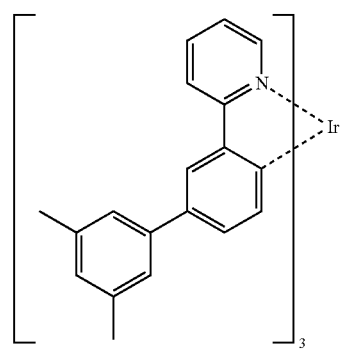
D-54
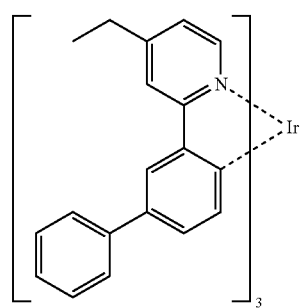
D-55
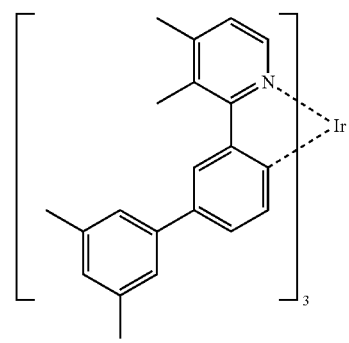
D-56
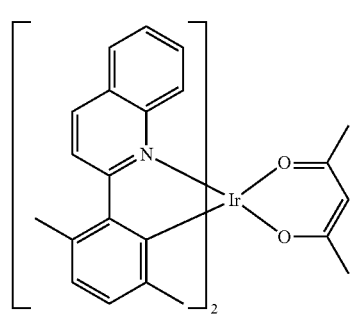
D-57
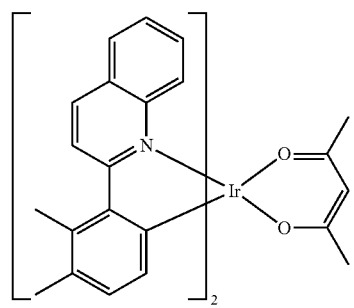
D-58
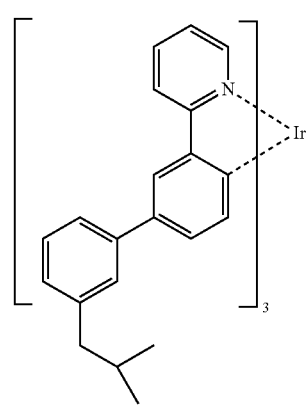

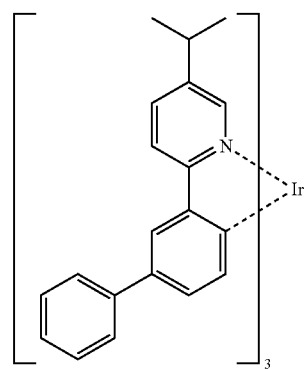
D-59
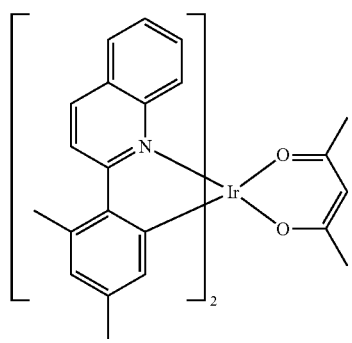
D-60
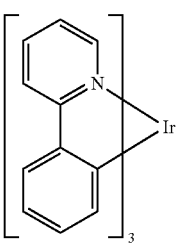
D-61
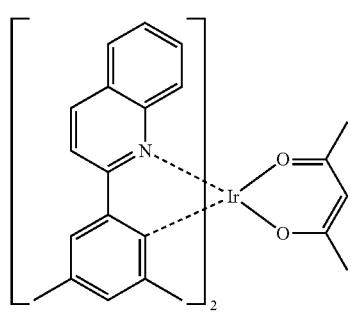
D-62
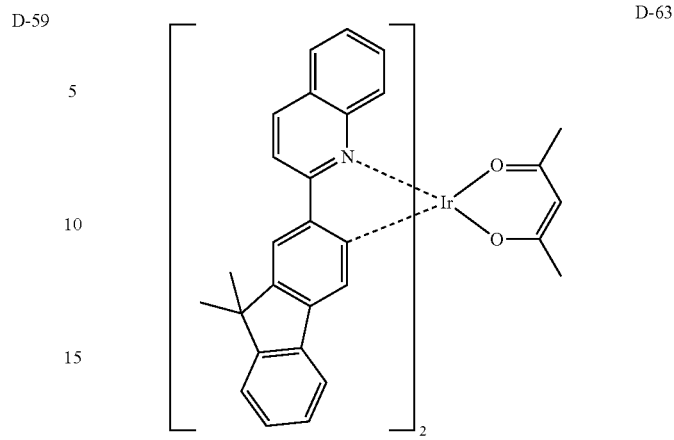
D-63
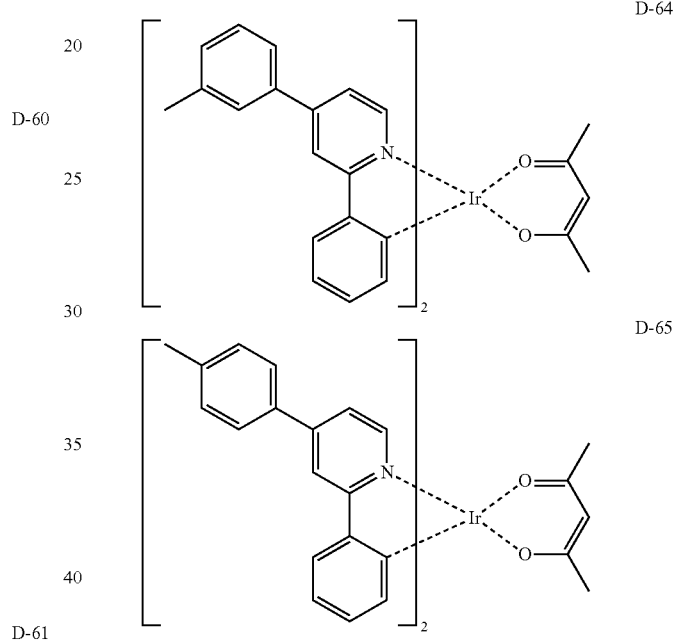
D-64
D-65
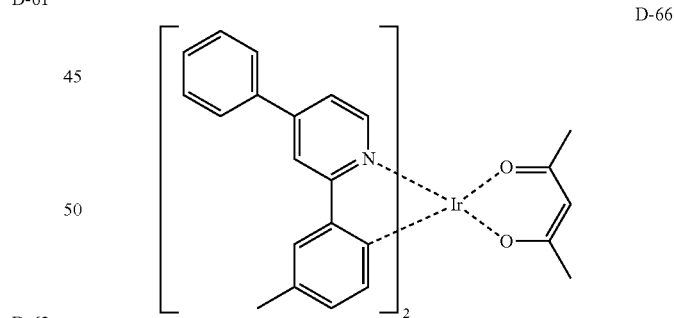
D-66
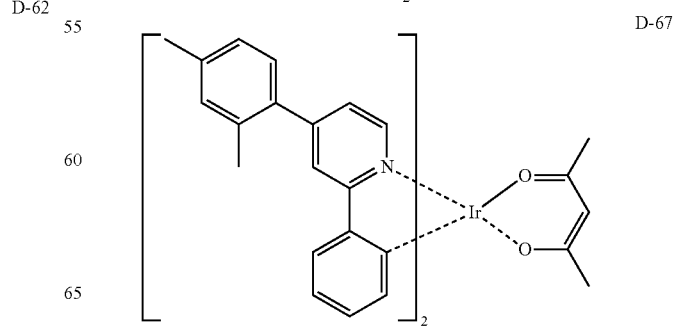
D-67

-continued
D-68
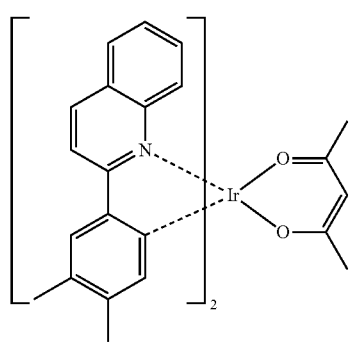
D-69
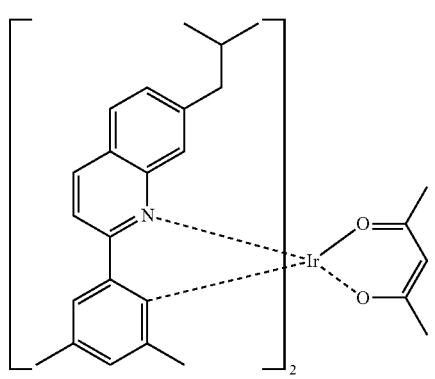
D-70
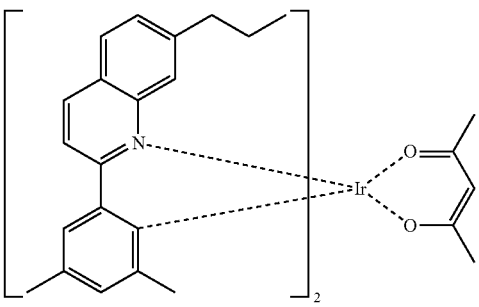
D-71
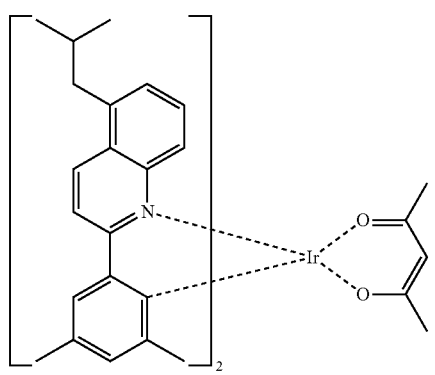
-continued
D-72
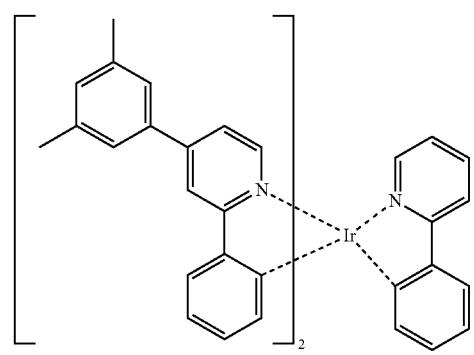
D-73
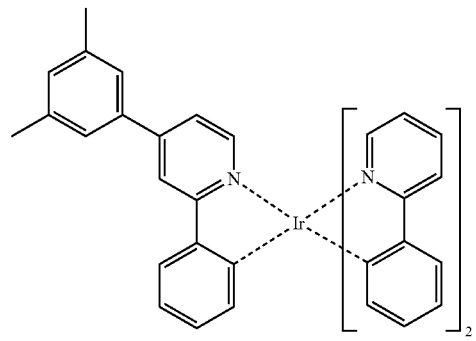
D-74
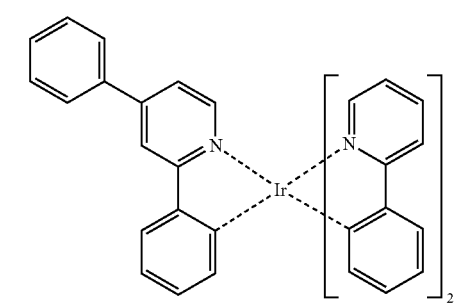
D-75
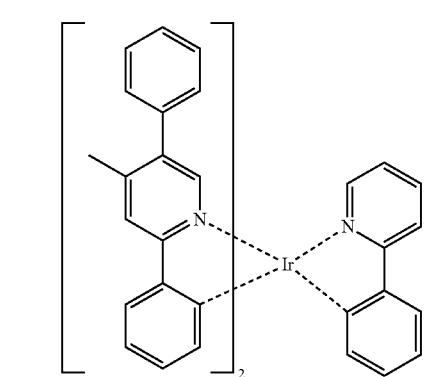

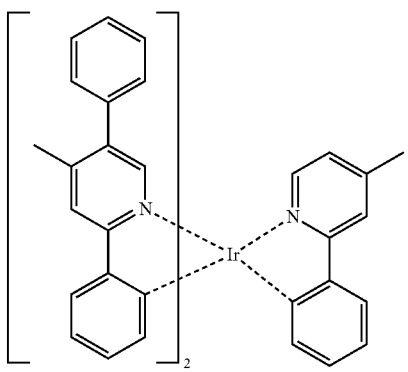
D-76
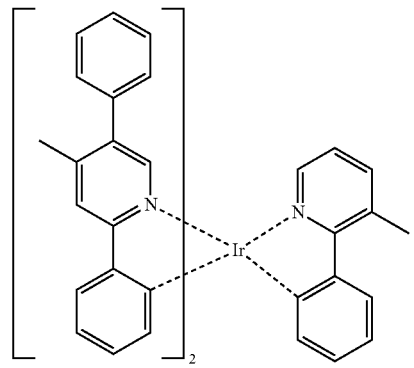
D-80
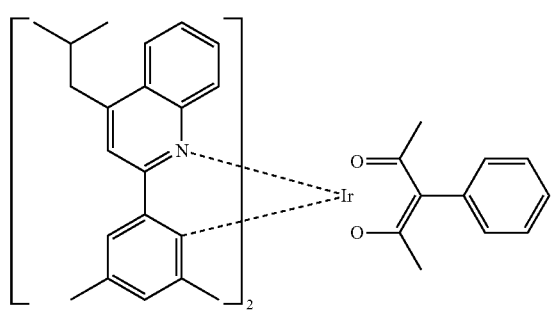
D-77
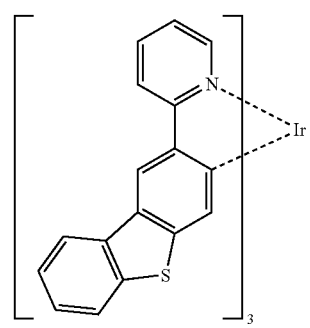
D-81
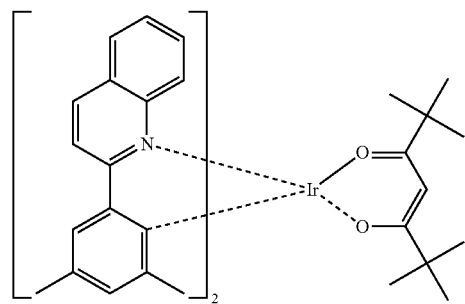
D-78
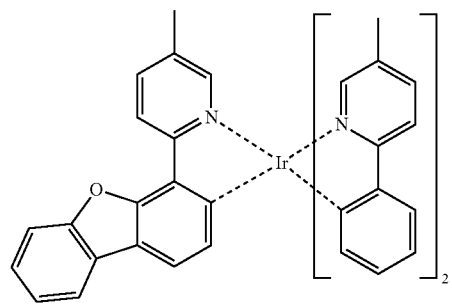
D-82
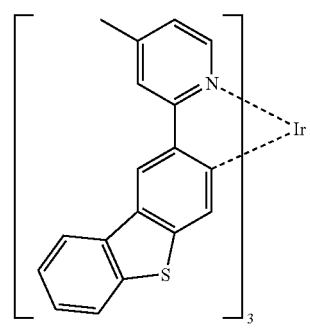
D-83
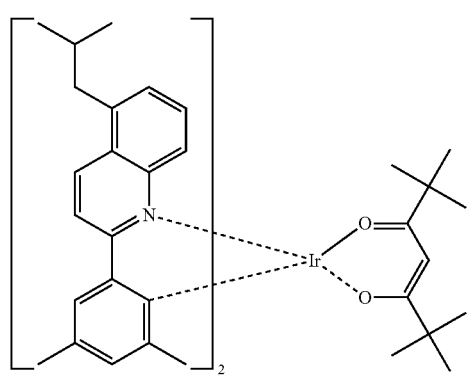
D-79
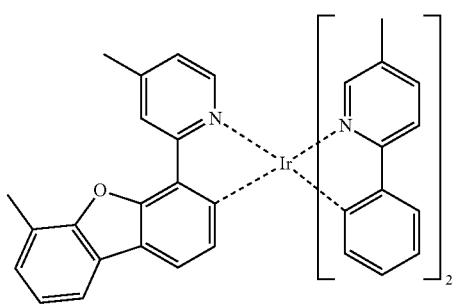
D-84

-continued
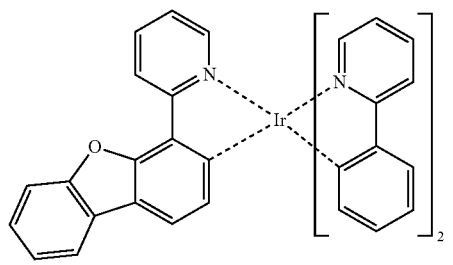
D-85
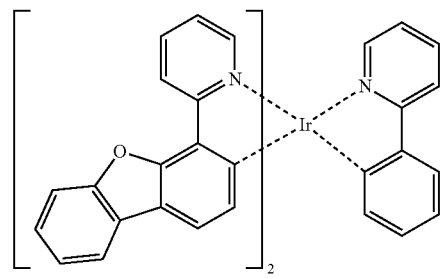
D-86
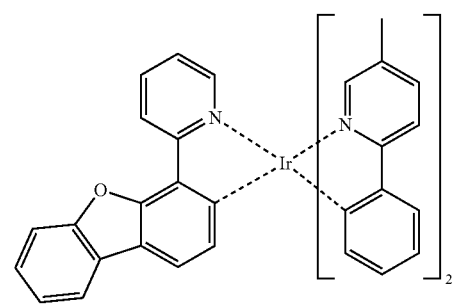
D-87
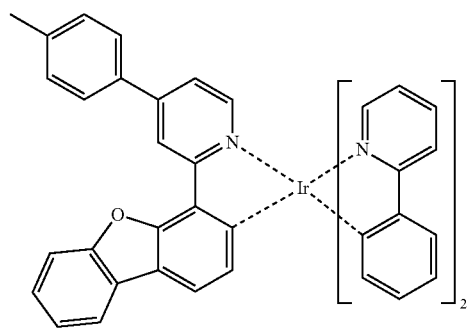
D-88
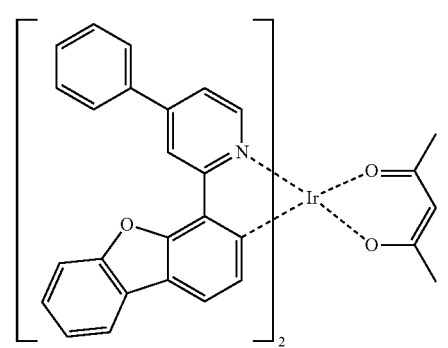
D-89
-continued
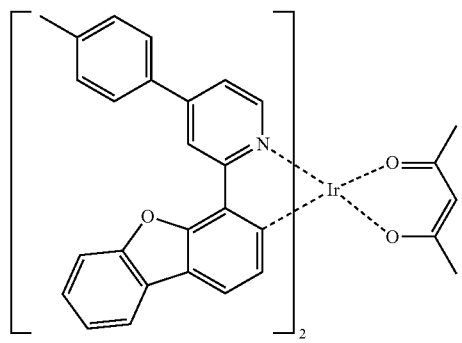
D-90
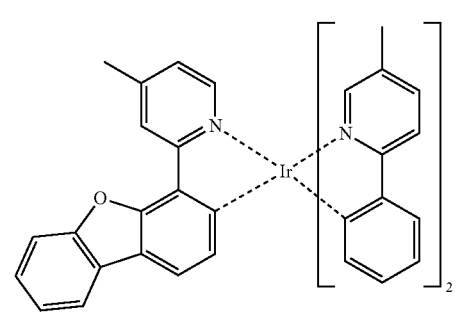
D-91
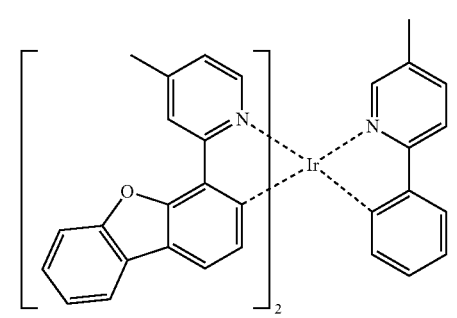
D-92
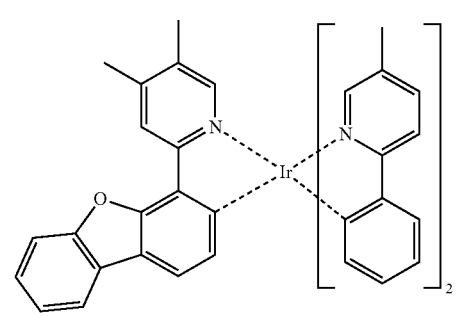
D-93
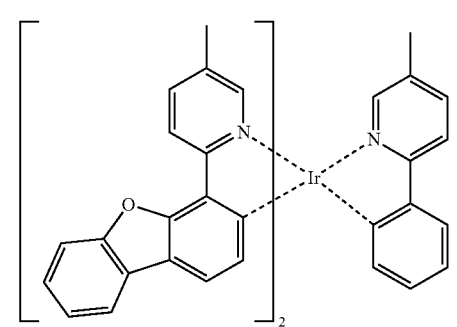
D-94

D-95
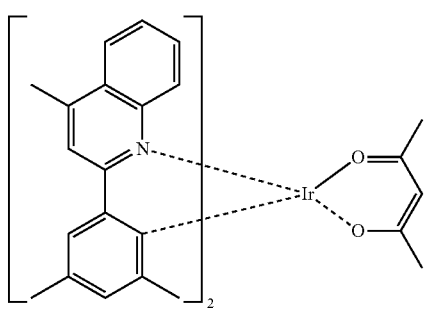
D-96
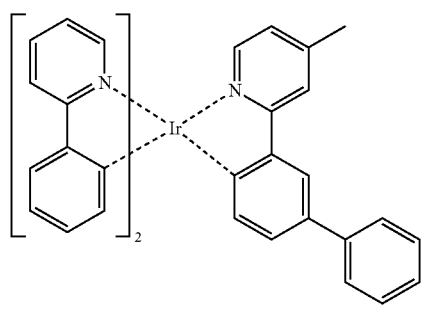
D-97
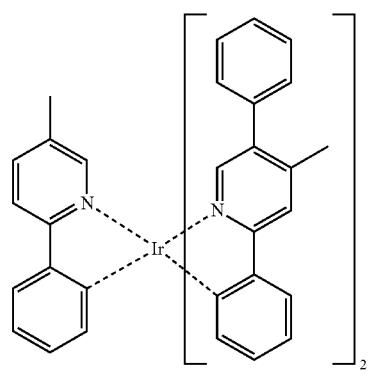
D-98
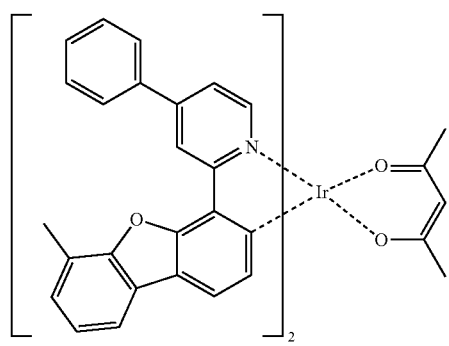
D-99
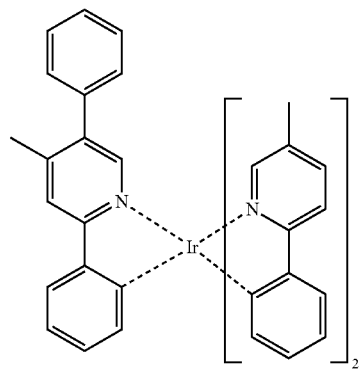
D-100
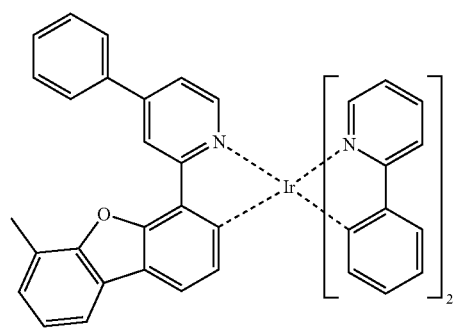
D-101
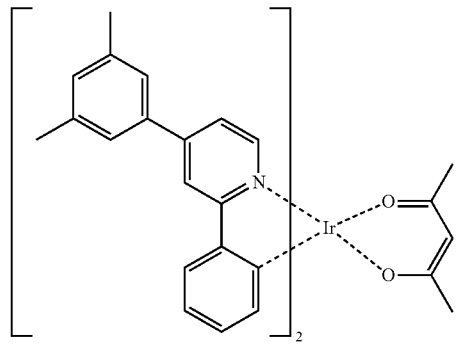
D-102
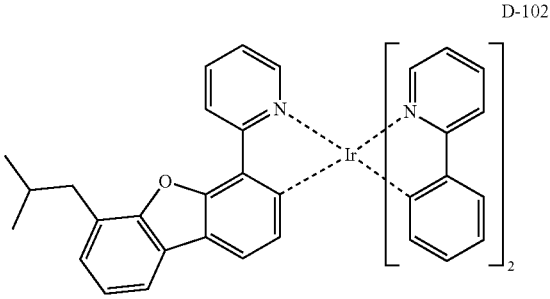

D-103
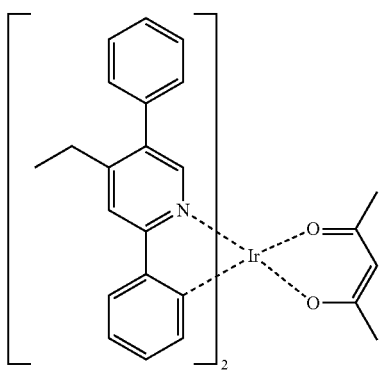
D-107
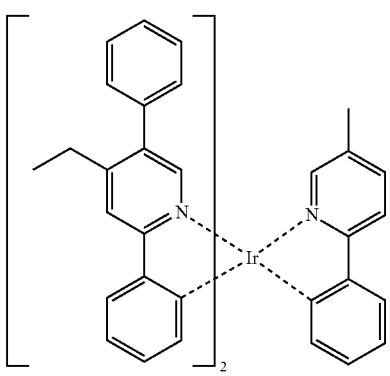
D-104
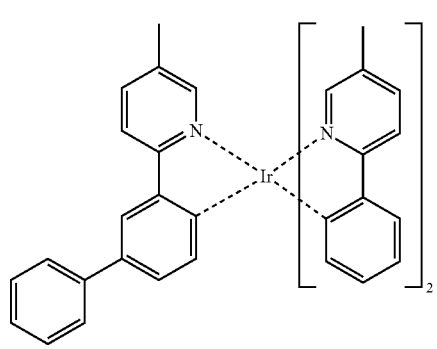
D-108
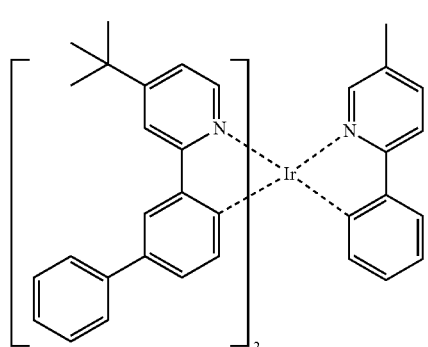
D-105
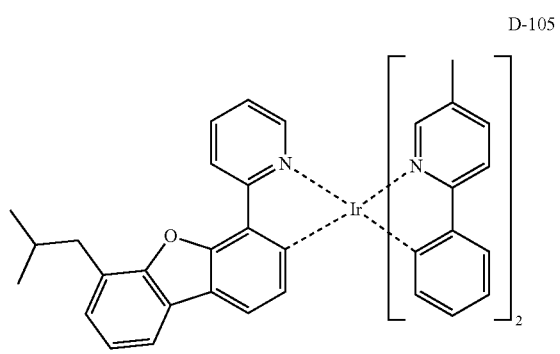
D-109
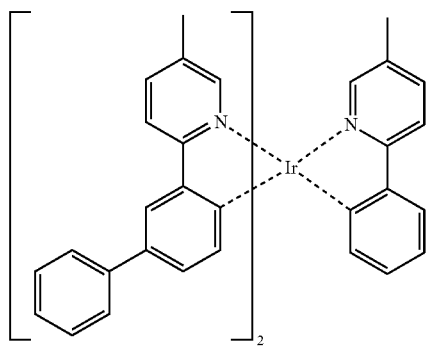
D-106
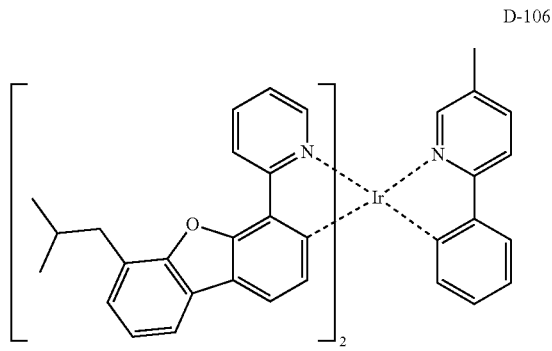
D-110
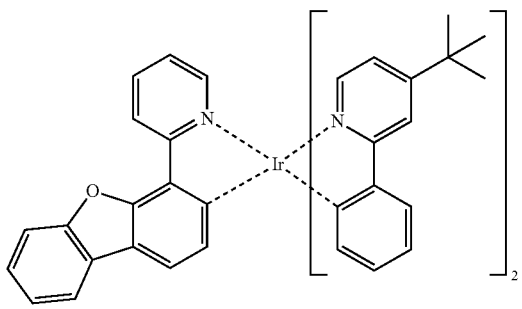

D-111 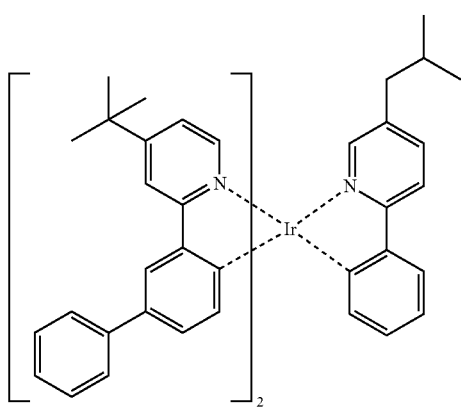
D-112 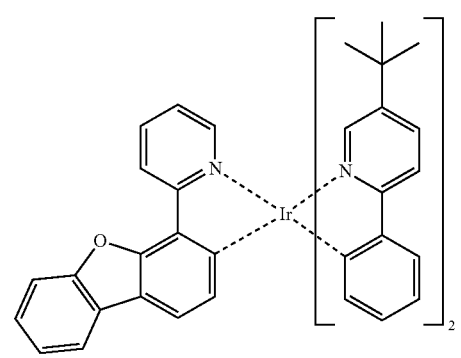
D-113 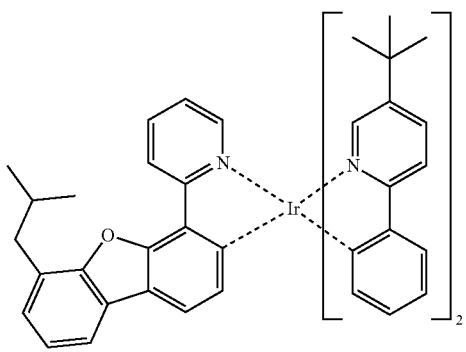
D-114 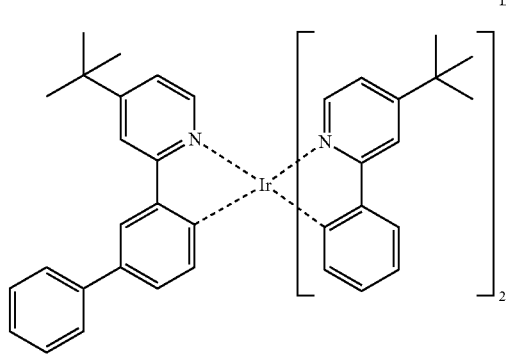
D-115 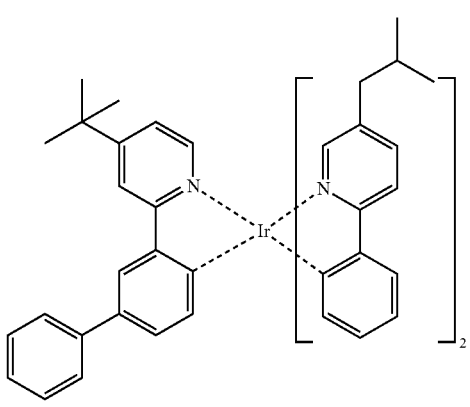
D-116 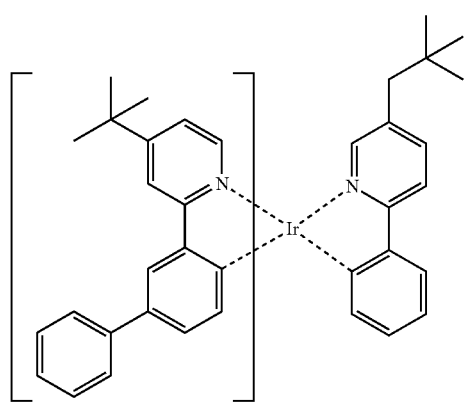
D-117 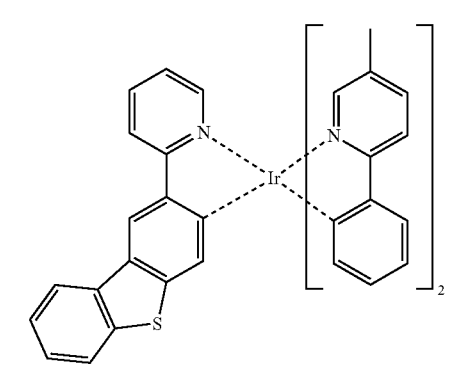
D-118 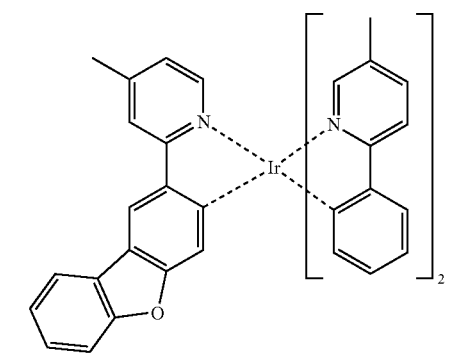

D-119
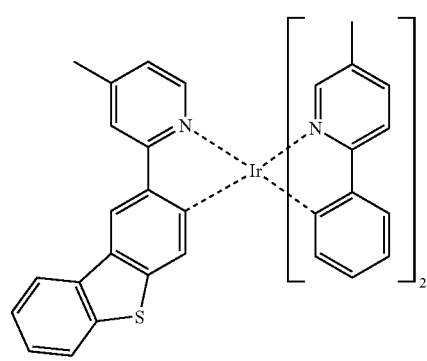
D-120
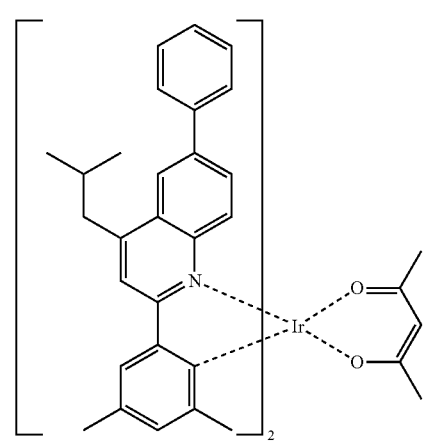
D-121
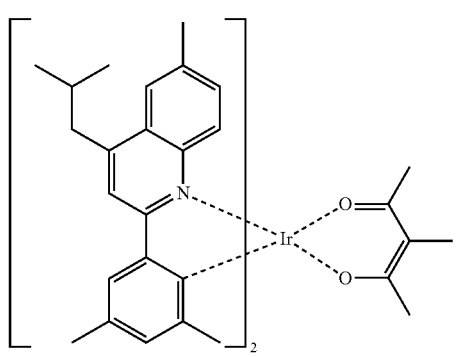
D-122
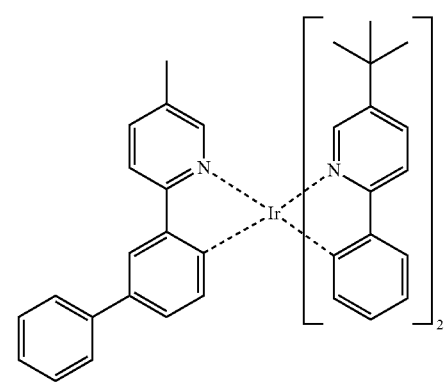
D-123
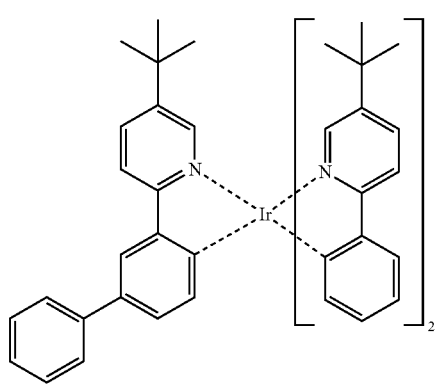
D-124
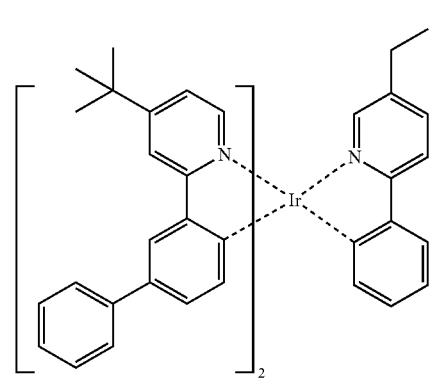
D-125
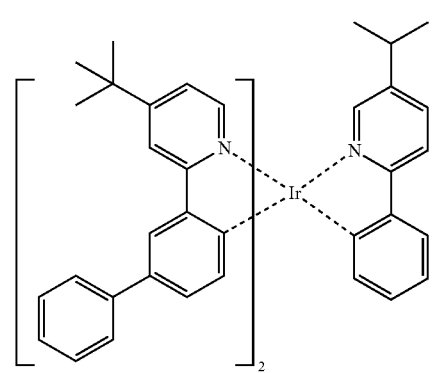
D-126
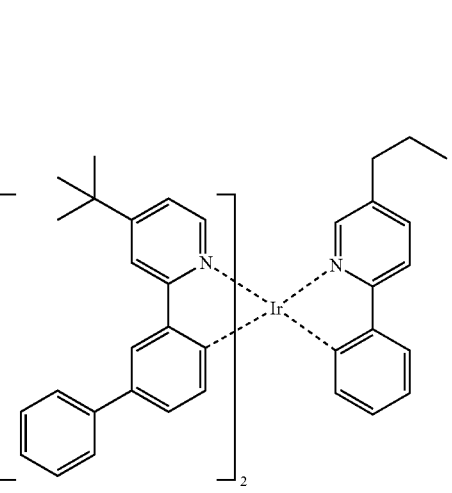

-continued
D-127
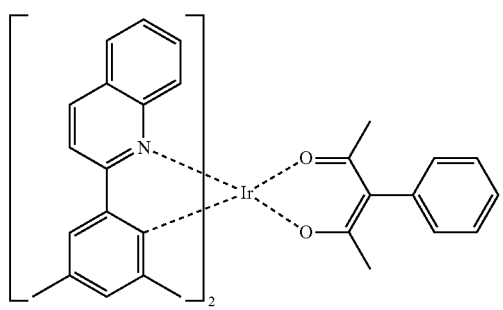
D-128
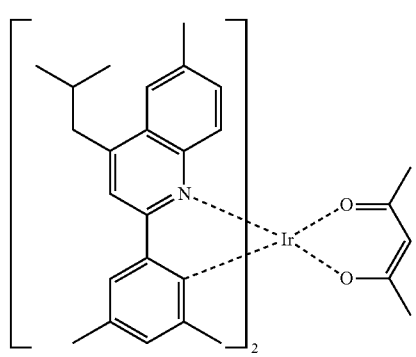
D-129
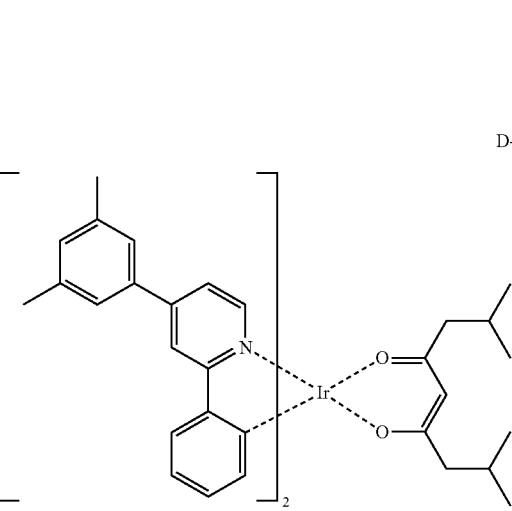
D-130
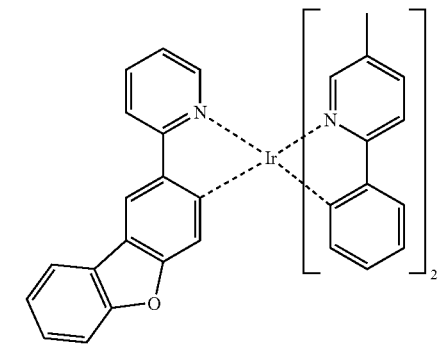
-continued
D-131
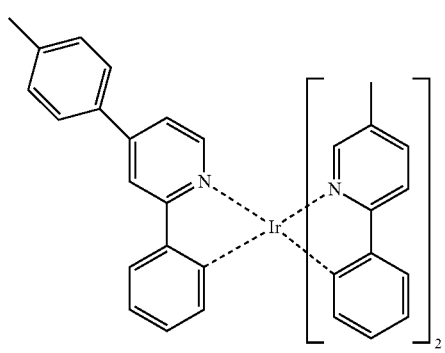
D-132
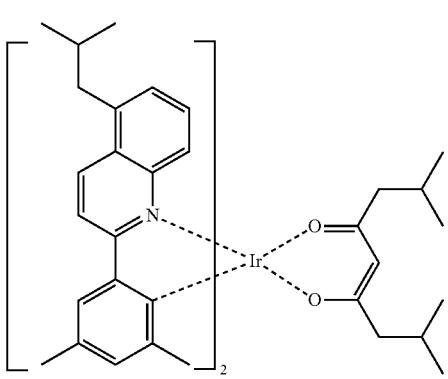
D-133
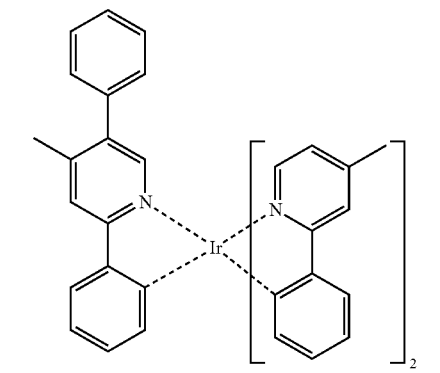
D-134
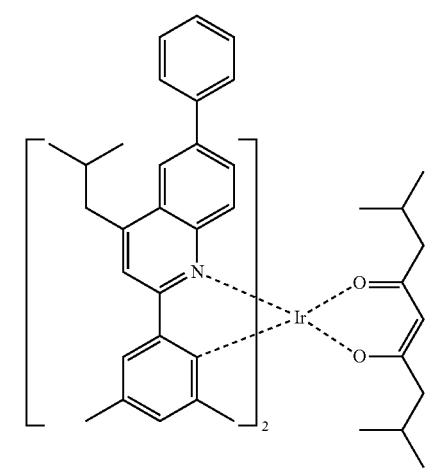

D-135
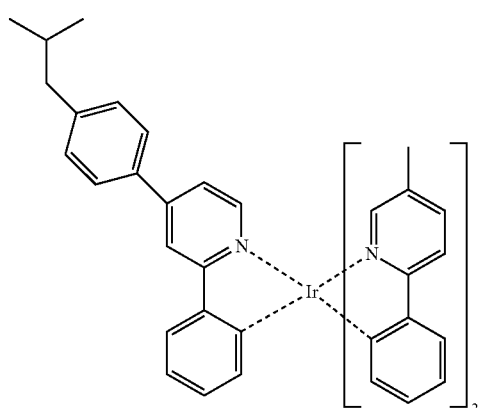
D-136
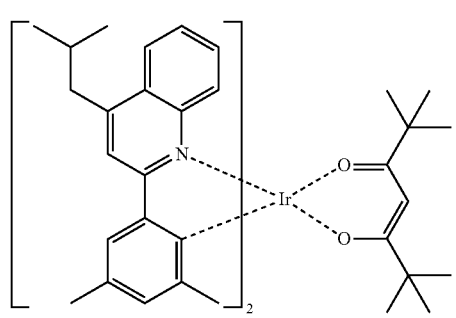
D-137
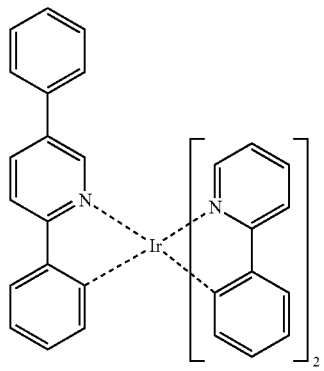
D-138
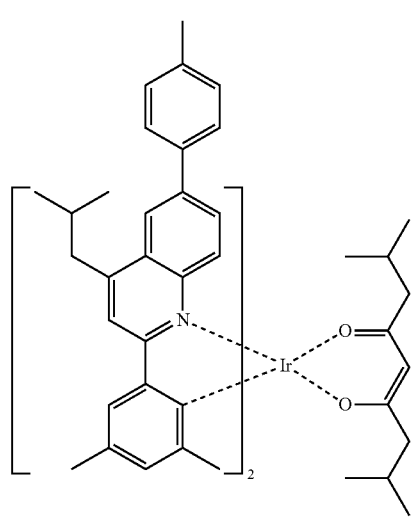
D-139
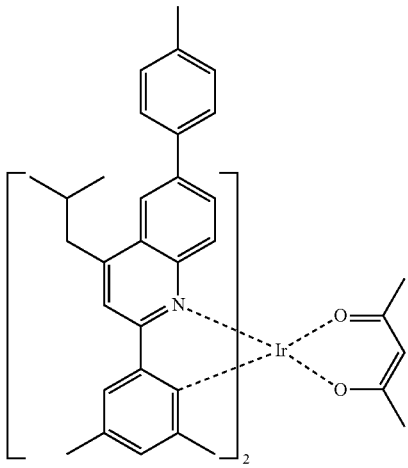
D-140
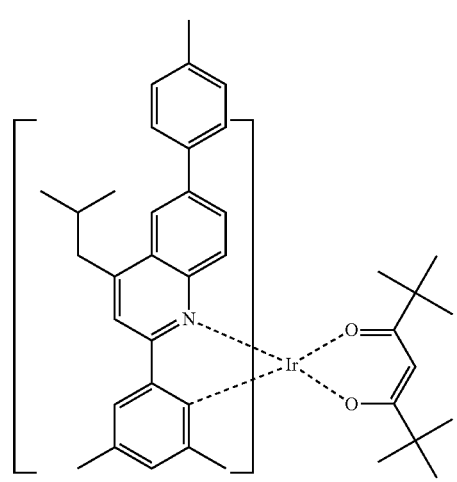
D-141
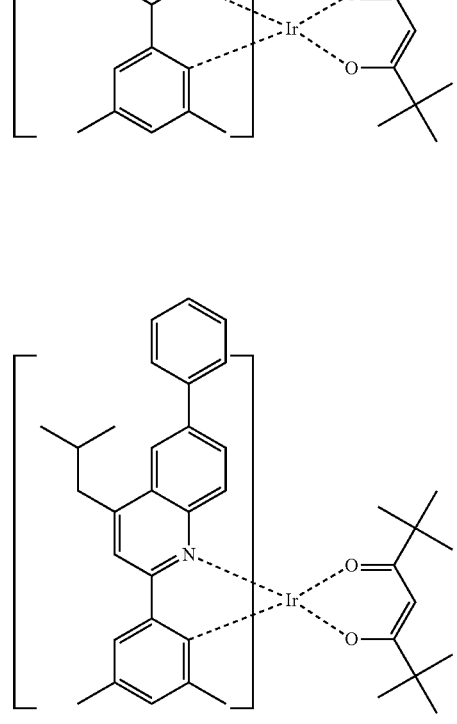

D-142
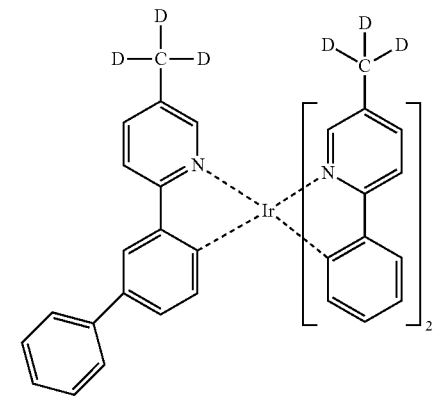
D-143
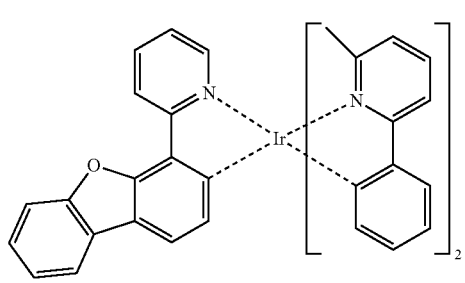
D-144
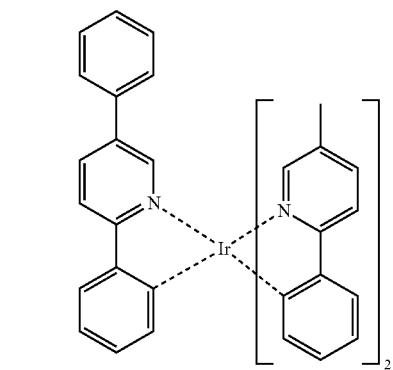
D-145
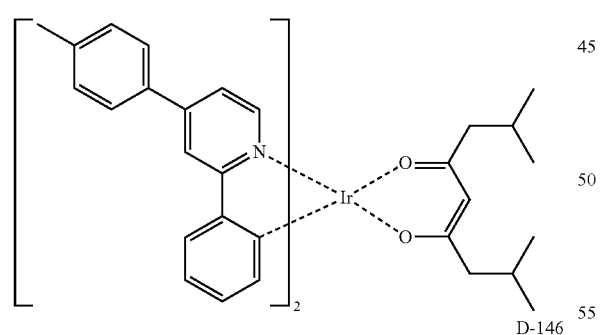
D-146
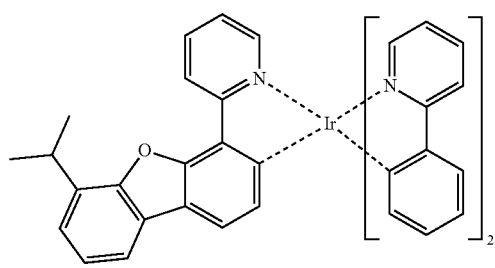
D-147
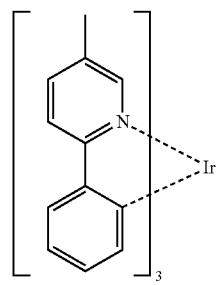
D-148
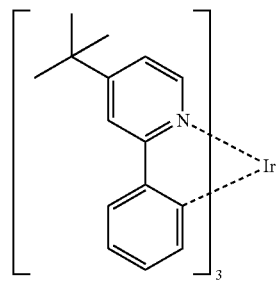
D-149
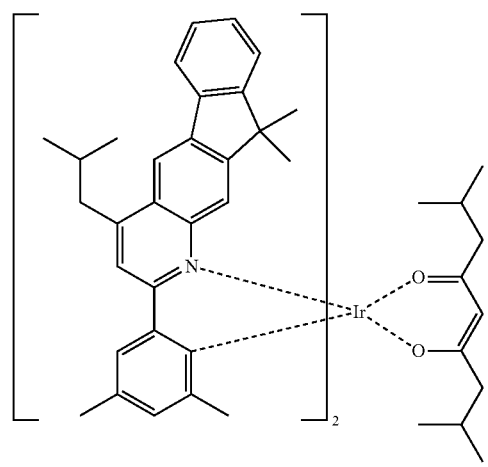
D-150
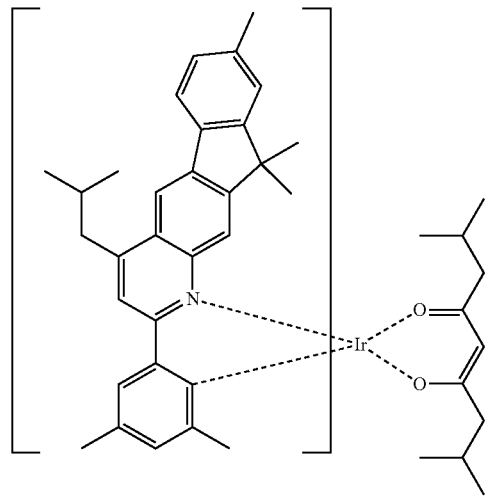

-continued
D-151
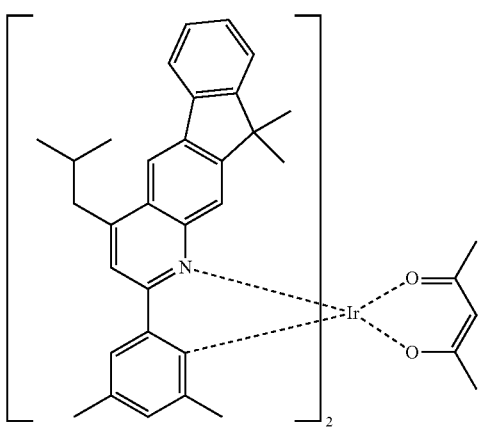
D-154
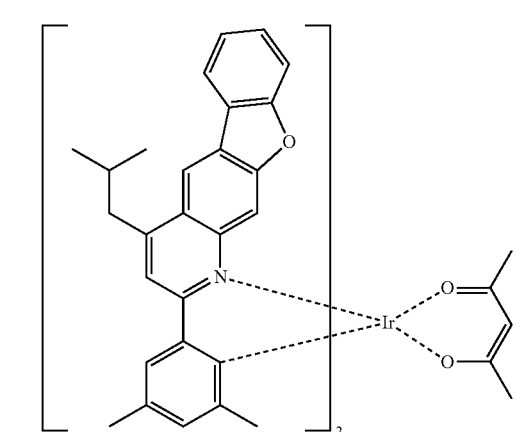
D-152
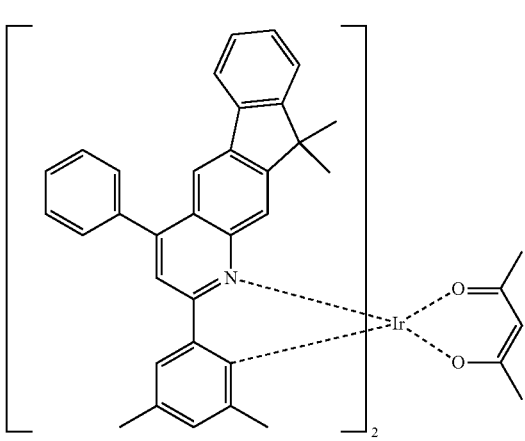
D-155
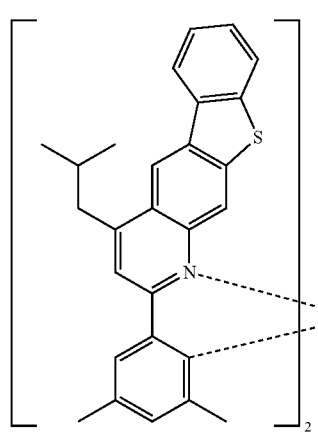
D-153
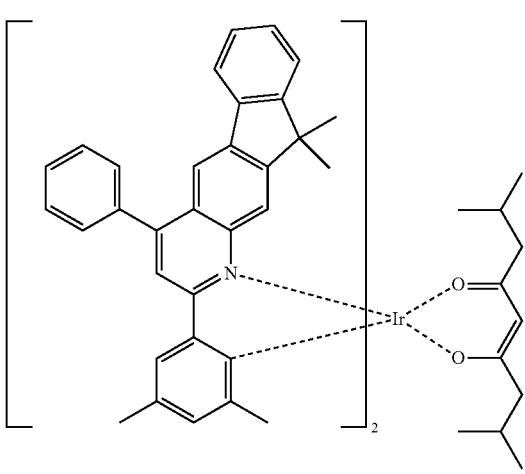
D-156
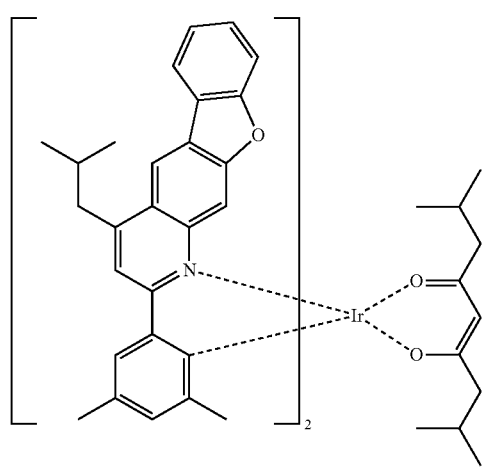

-continued

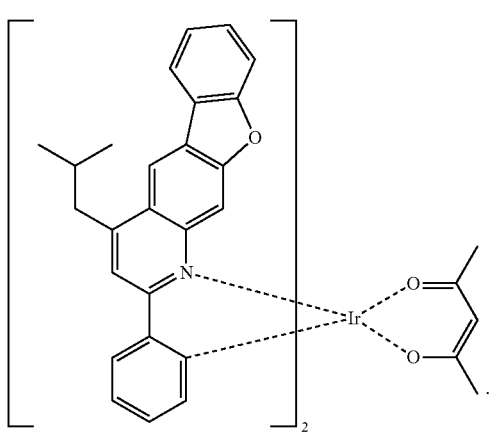

D-157

The formation of each layer of the organic electroluminescence device of the present disclosure can use one of dry film-forming methods such as vacuum evaporation, sputtering, plasma, ion plating methods, etc., and wet film-forming methods such as ink jet printing, nozzle printing, slot coating, spin coating, dip coating, flow coating methods, etc., but is not limited thereto. The dopant and the host compounds of the present disclosure may be co-evaporated or mixture-evaporated, but is not limited thereto.

When using a wet film-forming method, a thin film may be formed by dissolving or diffusing materials forming each layer into any suitable solvent such as ethanol, chloroform, tetrahydrofuran, dioxane, etc. The solvent may be any solvent where the materials forming each layer can be dissolved or diffused, and where there are no problems in film-formation capability.

The co-deposition is a mixed deposition method in which two or more isomer materials are put into respective individual crucible sources and a current is applied to both cells simultaneously to evaporate the materials and to perform mixed deposition; and the mixed deposition is a mixed deposition method in which two or more isomer materials are mixed in one crucible source before deposition, and then a current is applied to one cell to evaporate the materials.

Also, the organic electroluminescent device of the present disclosure can be used for the manufacture of display devices such as smartphones, tablets, notebooks, PCs, TVs, or display devices for vehicles, or lighting devices such as outdoor or indoor lighting.

Hereinafter, the preparation method of an organic electroluminescent compound according to the present disclosure, and the properties thereof will be explained in detail with reference to the representative compounds of the present disclosure in order to understand the present disclosure in detail. However, the present disclosure is not limited by the following examples.

EXAMPLE 1

Preparation of Compound C-8

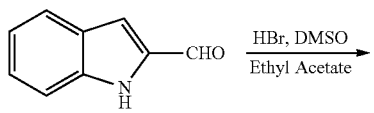

-continued

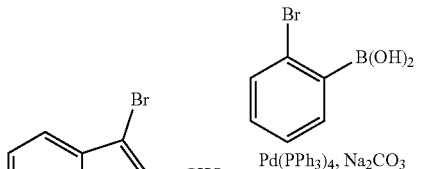

1-1

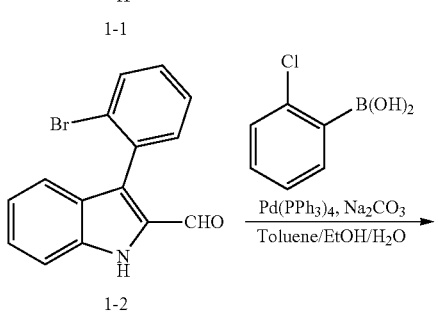

1-2

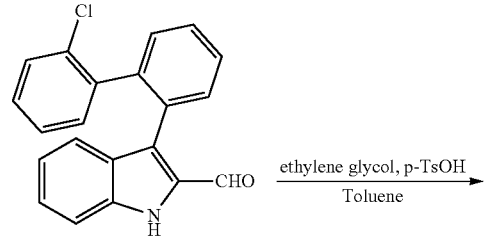

1-3

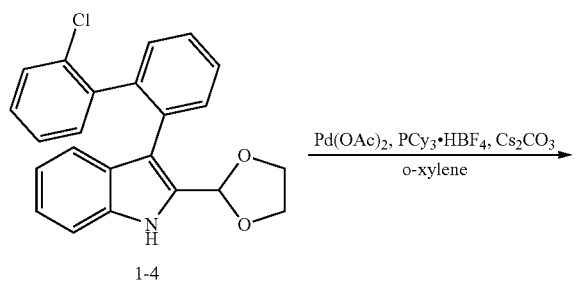

1-4

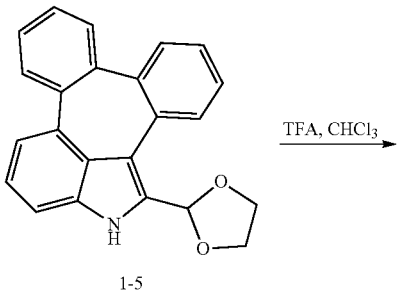

1-5

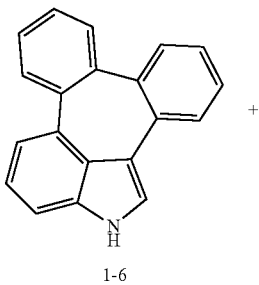

1-6

-continued

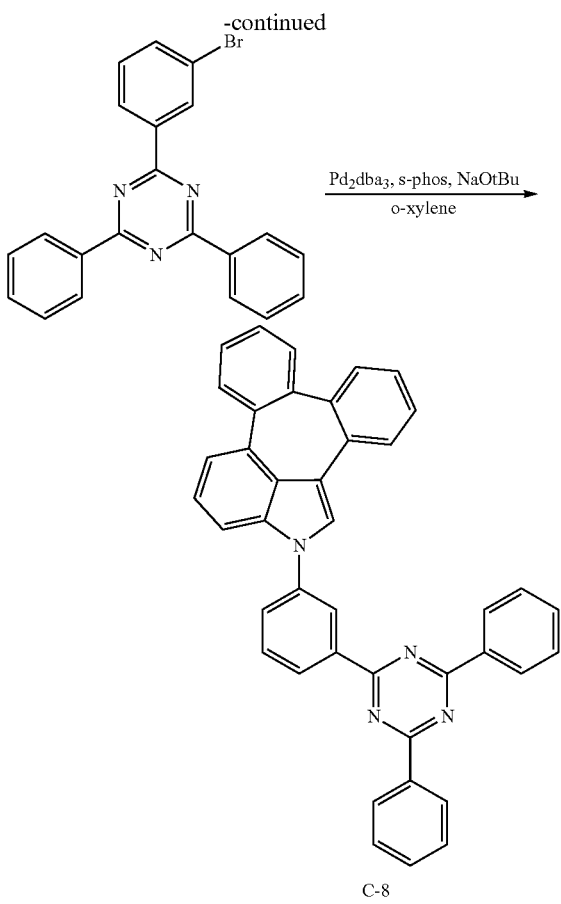

C-8

Preparation of Compound 1-1

1H-indole-2-carboxaldehyde (50 g, 344 mmol), dimethyl sulfoxide (29.3 mL, 413 mmol), hydrogen bromide (22.4 mL, 413 mmol), and 1,300 mL of ethyl acetate were added into a flask and dissolved, and then the mixture was stirred for 2 hours at 60° C. After completion of the reaction, the organic layer was extracted with ethyl acetate. The residual moisture was removed with magnesium sulfate and dried, and the resulting product was purified by column chromatography to obtain compound 1-1 (42.2 g, yield: 55%).

Preparation of Compound 1-2

Compound 1-1 (42.2 g, 188 mmol), 2-bromophenyl boronic acid (45.4 g, 226 mmol), tetrakis(triphenylphosphine)palladium(0) (10.9 g, 9.4 mmol), sodium carbonate (50 g, 471 mmol), 940 mL of toluene, and 235 mL of water were added into a flask and dissolved and then the mixture was refluxed for 4 hours. After completion of the reaction, the organic layer was extracted with ethyl acetate. The residual moisture was removed with magnesium sulfate and dried, and the resulting product was purified by column chromatography to obtain compound 1-2 (42 g, yield: 74%).

Preparation of Compound 1-3

Compound 1-2 (42 g, 299 mmol), 2-chlorophenyl boronic acid (26.2 g, 168 mmol), tetrakis(triphenylphosphine)palladium(0) (8.1 g, 7 mmol), sodium carbonate (37 g, 350 mmol), 700 mL of toluene, 170 mL of ethanol, and 170 mL of water were added into a flask and dissolved, and then the mixture was refluxed for 20 hours. After completion of the reaction, the organic layer was extracted with ethyl acetate. The residual moisture was removed with magnesium sulfate and dried, and the resulting product was purified by column chromatography to obtain compound 1-3 (36.5 g, yield: 78%).

Preparation of Compound 1-4

Compound 1-3 (10 g, 30 mmol), ethylene glycol (16.8 mL, 300 mmol), p-toluene sulfonic acid hydrate (57 mg, 0.3 mmol), and 170 mL of toluene were added into a flask and dissolved, and the mixture was refluxed for 20 hours. After completion of the reaction, the organic layer was extracted with ethyl acetate. The residual moisture was removed with magnesium sulfate and dried, and the resulting product was purified by column chromatography to obtain compound 1-4 (20 g, yield: 88%).

Preparation of Compound 1-5

Compound 1-4 (10 g, 26 mmol), palladium(II) acetate (0.29 g, 1.3 mmol), tricyclohexylphosphine tetrafluoroborate (979 mg, 2.6 mmol), cesium carbonate (17.3 g, 53 mmol), and 130 mL of 1,2-dimethylbenzene(o-xylene) were added into a flask and dissolved, and then the mixture was refluxed for 1 hour. After completion of the reaction, the organic layer was extracted with ethyl acetate. The residual moisture was removed with magnesium sulfate and dried, and the resulting product was purified by column chromatography to obtain compound 1-5 (7.7 g, yield: 85%).

Preparation of Compound 1-6

Compound 1-5 (17.2 g, 50.7 mmol), 75 mL of triflic acid, and 200 mL of chloroform were added into a flask and dissolved, and then the mixture was stirred for 24 hours at room temperature. After completion of the reaction, the organic layer was extracted with ethyl acetate after neutralizing with sodium bicarbonate. The residual moisture was removed with magnesium sulfate and dried, and the resulting product was purified by column chromatography to obtain compound 1-6 (10 g, yield: 74%).

Preparation of compound C-8

Compound 1-6 (4 g, 15 mmol), 2-(3-bromophenyl)-4,6-diphenyl-1,3,5-triazine (5.8 g, mmol), tris(dibenzylideneacetone)dipalladium(0) (0.54 g, 0.6 mmol), 2-dicyclohexylphosphino-2',6'-dimethoxybiphenyl (0.6 g, 1.5 mmol), sodium-tert-butoxide (3.6 g, 37 mmol), and 100 mL of 1,2-dimethylbenzene(o-xylene) were added into a flask and dissolved, and then the mixture was refluxed for 24 hours. After completion of the reaction, the organic layer was extracted with ethyl acetate after vacuum distillation. The residual moisture was removed with magnesium sulfate and dried, and the resulting product was purified by column chromatography to obtain compound C-8 (6.0 g, yield: 70%).

| Compound | MW | M.P. | Tg |
|---|---|---|---|
| C-8 | 574.67 | 315° C. | 134° C. |

Hereinafter, the preparation method of an organic electroluminescent device comprising the host compound of the present disclosure, and the luminescent characteristics thereof will be described in order to understand the present disclosure in detail.

DEVICE EXAMPLE 1

Producing an Organic Electroluminescent Device by Deposition of the Compound According to the Present Disclosure as a Host An OLED device not according to the present disclosure was produced. A transparent electrode indium tin oxide (ITO) thin film (10 Ω/sq) on a glass substrate for an OLED (GEOMATEC CO., LTD., Japan) was subjected to an ultrasonic washing with acetone, ethanol, and distilled water, sequentially, and then was stored in isopropanol. Next, the ITO substrate was mounted on a substrate holder of a vacuum vapor deposition apparatus. Compound HI-1 was introduced into a cell of the vacuum vapor deposition apparatus, and the pressure in the chamber of the apparatus was then controlled to $10^{-6}$ torr. Thereafter, an electric current was applied to the cell to evaporate the introduced material, thereby forming a first hole injection layer having a thickness of 80 nm on the ITO substrate. Compound HI-2 was then introduced into another cell of the vacuum vapor deposition apparatus, and an electric current was applied to the cell to evaporate the introduced material, thereby forming a second hole injection layer having a thickness of 5 nm on the first hole injection layer. Next, compound HT-1 was introduced into another cell of the vacuum vapor deposition apparatus. Thereafter, an electric current was applied to the cell to evaporate the introduced material, thereby forming a first hole transport layer having a thickness of 10 nm on the second hole injection layer. Compound HT-2 was then introduced into another cell of the vacuum vapor deposition apparatus, and an electric current was applied to the cell to evaporate the introduced material, thereby forming a second hole transport layer having a thickness of 60 nm on the first hole transport layer. After forming the hole injection layers and the hole transport layers, a light-emitting layer was then deposited as follows. Compound C-8 as a host was introduced into one cell of the vacuum vapor deposition apparatus and compound D-71 as a dopant was introduced into another cell of the apparatus. The two materials were evaporated at a different rate and the dopant was deposited in a doping amount of 3 wt %, based on the total weight of the host and dopant, to form a light-emitting layer having a thickness of 40 nm on the second hole transport layer. Next, as an electron transport material, compound ETL-1 was introduced into one cell, and as an electron injection material, compounds ETL-1 and EIL-1 were introduced into another cell, were evaporated at a rate of 1:1, and deposited to form an eletron transport layer having a thickness of 30 nm on the light-emitting layer. Next, compound EIL-1 as an electron injection layer having a thickness of 2 nm was deposited on the electron transport layer, and an Al cathode having a thickness of 80 nm was deposited by another vacuum vapor deposition apparatus on the electron injection layer.

As a result, the efficiency of 23.8 cd/A at a voltage of 3.0 V was confirmed; also, the red-emission of 1,000 cd/m$^2$ was confirmed. Also, the minimum time taken for the light-emission to be reduced from 100% to 90% at a luminance of 5,000 nit was 9 hour.

COMPARATIVE EXAMPLE 1

Producing an Organic Electroluminescent Device Comprising the Conventional Compound as a Host An OLED device was produced in the same manner as in Device Example 1, except compound X as a host of the light-emitting layer.

As a result, the efficiency of 9.2 cd/A at a voltage of 9.2 V was confirmed; also, the red-emission of 1,000 cd/m$^2$ was confirmed. Further, the minimum time taken for the light-emission to be reduced from 100% to 90% at a luminance of 5,000 nit was 0.9 hour.

The compounds used in Device Example 1 and Comparative Example 1 are shown in Table 1 below.

TABLE 1

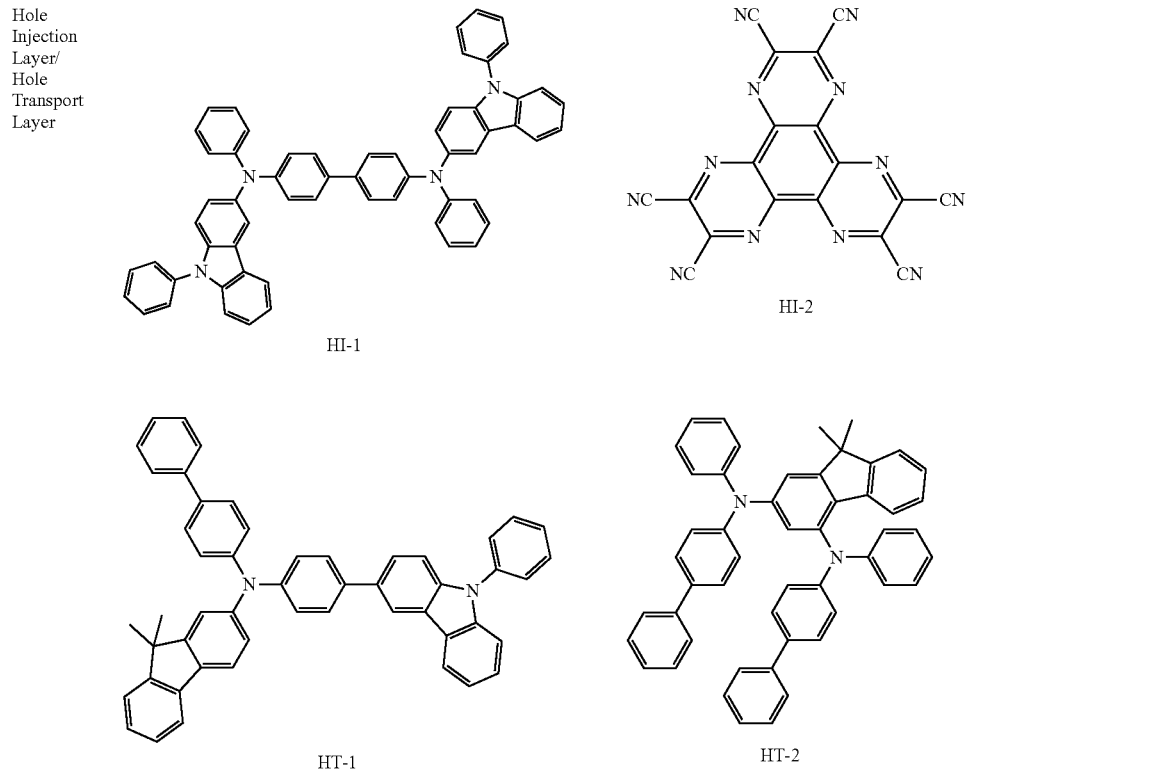

TABLE 1-continued

Light-Emitting Layer

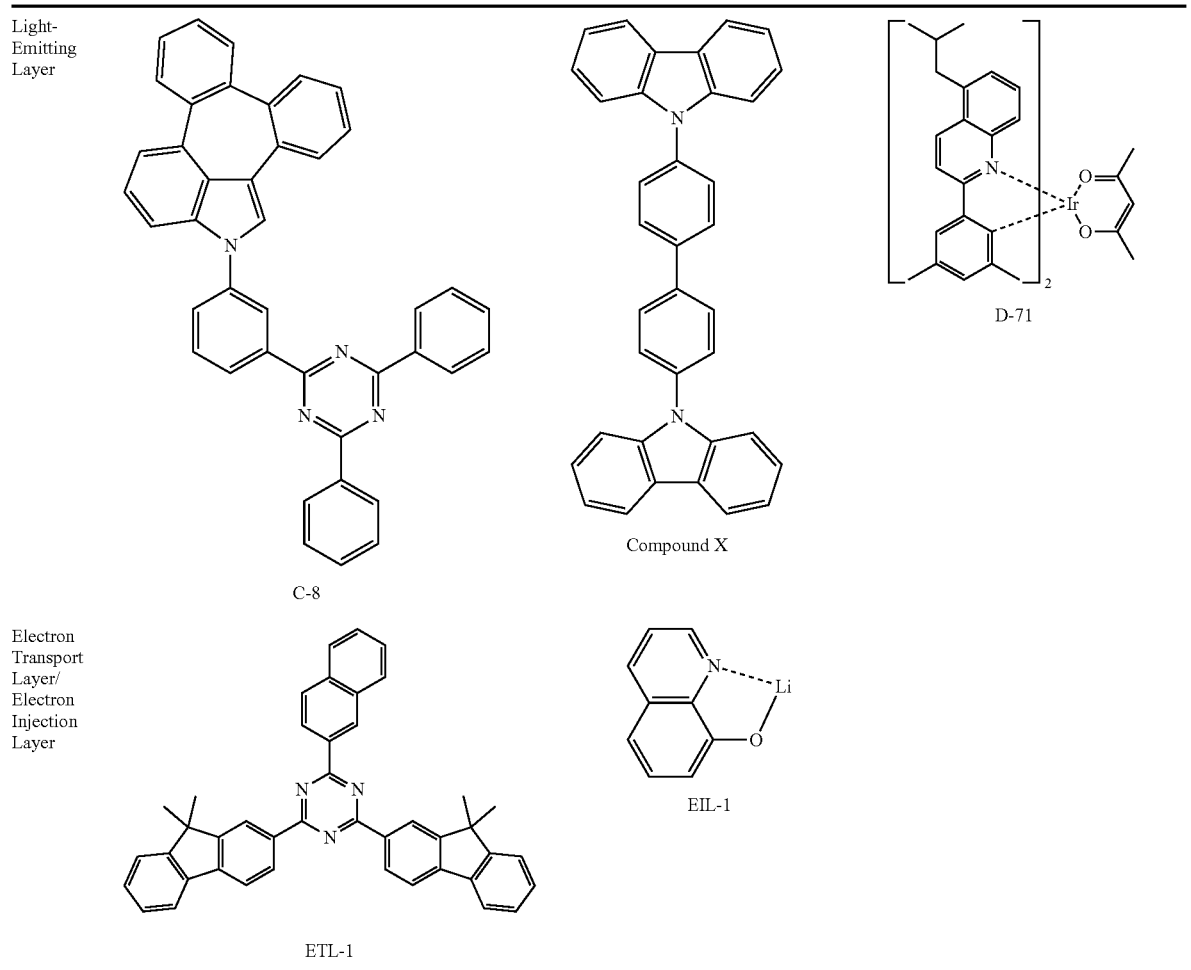

C-8

Compound X

D-71

Electron Transport Layer/ Electron Injection Layer

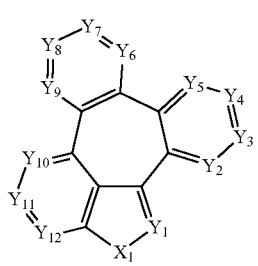

ETL-1

EIL-1

From Device Example 1 and Comparative Example 1 above, it was confirmed that the OLED device using the organic electroluminescent compound according to the present disclosure as the light-emitting material has far better driving lifespan than the OLED device using the conventional light-emitting material.

That is, when the organic electroluminescent compound according to the present disclosure is used, the organic electroluminescent compound can be advantageous in lowering power consumption since the voltage used to emit light of the same brightness is low. Furthermore, it has the advantage of increasing battery usage time in a portable display device, where the OLED panel is mainly used.

The invention claimed is:

1. An organic electroluminescent compound represented by the following formula 1:

(1)

wherein, $X_1$ represents N-L-(Ar)$_a$;

L represents a single bond, a substituted or unsubstituted (C6-C30)arylene, or a substituted or unsubstituted (3- to 30-membered)heteroarylene;

Ar represents hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted mono- or di- (C1-C30)alkylamino, a substituted or unsubstituted mono-or di- (C6-C30)arylamino, or a substituted or unsubstituted (C1-C30)alkyl(C6-C30)arylamino;

$Y_1$ to $Y_{12}$ each independently represent N or $CR_1$;

$R_1$ each independently represents hydrogen, deuterium, halogen, cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di- (C1-C30)alkylamino, a substituted or unsubstituted mono-or di- (C6-C30)arylamino, or a substituted or unsubstituted (C1-C30)alkyl (C6-C30)arylamino; or may be linked to an adjacent substituent to form a substituted or unsubstituted ring; and a represents an integer of 1 to 4, wherein when a is 2 to 4, each of Ar may be the same or different.

2. The organic electroluminescent compound according to claim 1, wherein the substituents of the substituted (C1-C30)alkyl, the substituted (C6-C30)aryl(ene), the substituted 3- to 30-membered)heteroaryl(ene), the substituted (C3-C30)cycloalkyl, the substituted (C1-C30)alkoxy, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di- (C1-C30)alkylamino, the substituted mono- or di- (C6-C30)arylamino, the substituted (C1-C30)alkyl(C6-C30)arylamino, and the substituted ring, in L, Ar, and $R_1$, are each independently at least one selected from the group consisting of deuterium, halogen, cyano, carboxyl, nitro, hydroxyl, (C1-C30)alkyl, halo(C1-C30)alkyl, (C2-C30)alkenyl, (C2-C30)alkynyl, (C1-C30)alkoxy, (C1-C30)alkylthio, (C3-C30)cycloalkyl, (C3-C30)cycloalkenyl, (3- to 7-membered)heterocycloalkyl, (C6-C30)aryloxy, (C6-C30)arylthio, (C6-C30)aryl-substituted or unsubstituted (5- to 30-membered)heteroaryl, (5- to 30-membered)heteroaryl-substituted or unsubstituted (C6-C30)aryl, di(C6-C30)arylamino-substituted (C6-C30)aryl, tri(C1-C30)alkylsilyl, tri(C6-C30)arylsilyl, di(C1-C30)alkyl(C6-C30)arylsilyl, (C1-C30)alkyldi(C6-C30)arylsilyl, amino, a mono- or di- (C1-C30)alkylamino, (C1-C30)alkyl-substituted or unsubstituted mono- or di- (C6-C30)arylamino, (C1-C30)alkyl(C6-C30)arylamino, (C1-C30)alkylcarbonyl, (C1-C30)alkoxycarbonyl, (C6-C30)arylcarbonyl, di(C6-C30)arylboronyl, di(C1-C30)alkylboronyl, (C1-C30)alkyl(C6-C30)arylboronyl, (C6-C30)ar(C1-C30)alkyl, and (C1-C30)alkyl(C6-C30)aryl.

3. The organic electroluminescent compound according to claim 1, wherein
L represents a single bond, a substituted or unsubstituted (C6-C30)arylene, or a substituted or unsubstituted (3- to 30-membered)heteroarylene;
Ar represents hydrogen, deuterium, a substituted or unsubstituted (C6-C30)aryl, a substituted or unsubstituted (3- to 30-membered)heteroaryl, or a substituted or unsubstituted di(C6-C30)arylamino;
$R_1$ each independently represents hydrogen, a substituted or unsubstituted (C1-C30)alkyl, a substituted or unsubstituted (C6-C30)aryl, a substituted or unsubstituted (3- to 30-membered)heteroaryl, or a substituted or unsubstituted di(C6-C30)arylamino; or may be linked to an adjacent substituent to form a ring of a substituted or unsubstituted, (C3-C30) mono- or polycyclic, aromatic ring, whose at least one carbon atom may be replaced with nitrogen;
wherein the substituents of the substituted (C6-C30)aryl (ene), the substituted 3- to 30-membered)heteroaryl (ene), the substituted di(C6-C30)arylamino in L, Ar, and are each independently at least one selected from the group consisting of deuterium, (5- to 30-membered) heteroaryl-substituted or unsubstituted (C6-C30)aryl, (C6-C30)aryl-substituted or unsubstituted (5- to 30-membered)heteroaryl, amino, a mono- or di- (C1-C30)alkylamino, (C1-C30)alkyl-substituted or unsubstituted mono-or di- (C6-C30)arylamino, (C1-C30)alkyl(C6-C30)arylamino.

4. The organic electroluminescent compound according to claim 1, wherein
L represents a single bond, a substituted or unsubstituted phenylene, a substituted or unsubstituted m-biphenylene, a substituted or unsubstituted p-biphenylene, a substituted or unsubstituted pyridinylene, a substituted or unsubstituted pyrimidylene, a substituted or unsubstituted triazinylene, a substituted or unsubstituted naphthylene, a substituted or unsubstituted quinazolinylene, or a substituted or unsubstituted quinoxalinylene; Ar represents hydrogen, a substituted or unsubstituted phenyl, a substituted or unsubstituted naphthyl, a substituted or unsubstituted m-biphenyl, a substituted or unsubstituted p-biphenyl, a substituted or unsubstituted triazinyl, a substituted or unsubstituted pyridyl, a substituted or unsubstituted pyrimidinyl, a substituted or unsubstituted quinazolinyl, a substituted or unsubstituted quinoxalinyl, a substituted or unsubstituted carbazolyl, a substituted or unsubstituted diphenylamino, or a substituted or unsubstituted fluorenylphenylamino.

5. The organic electroluminescent compound according to claim 1, wherein, two adjacents among $Y_1$ to $Y_{12}$ represent $CR_1$, two adjacent $R_1$ are fused with each other to form a ring represented by any one of the following formulae 2 to 5, and the compound of formula 1 contains at least one of the following rings:

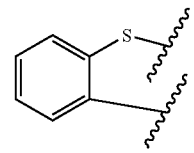

(2)

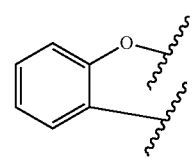

(3)

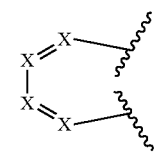

(4)

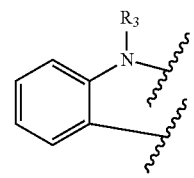

(5)

wherein,
X represents N or $CR_2$,
$R_2$ represents hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30) arylsilyl, a substituted or unsubstituted tri(C6-C30) arylsilyl, a substituted or unsubstituted mono- or di-(C1-C30)alkylamino, a substituted or unsubstituted mono-or di- (C6-C30)arylamino, or a substituted or unsubstituted (C1-C30)alkyl(C6-C30)arylamino, R₃ represents hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30) arylsilyl, a substituted or unsubstituted tri(C6-C30) arylsilyl, a substituted or unsubstituted mono- or di-(C1-C30)alkylamino, a substituted or unsubstituted mono-or di- (C6-C30)arylamino, or a substituted or unsubstituted (C1-C30)alkyl(C6-C30)arylamino, resents a linking site with C of CR₁.

6. The organic electroluminescent compound according to claim 1, wherein the compound represented by formula 1 is selected from the group consisting of:

C-1
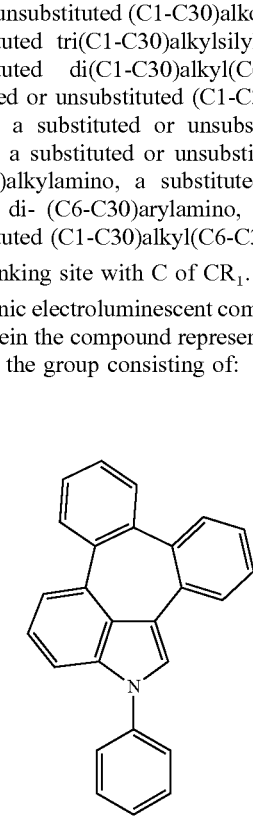

C-2
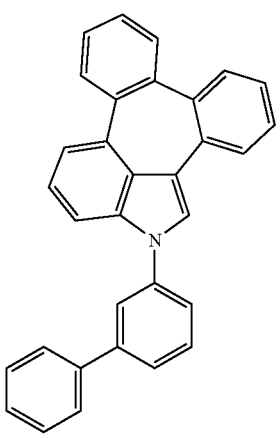

C-3
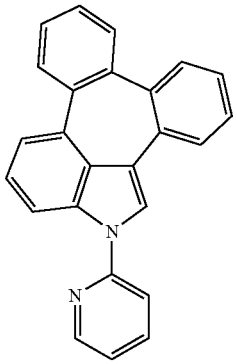

C-4
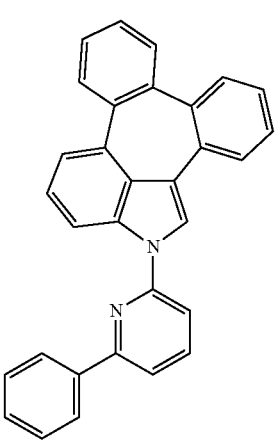

C-5
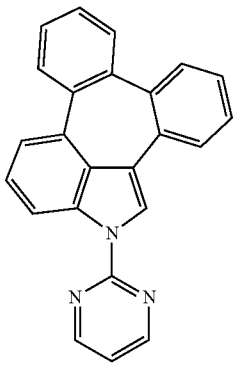

C-6
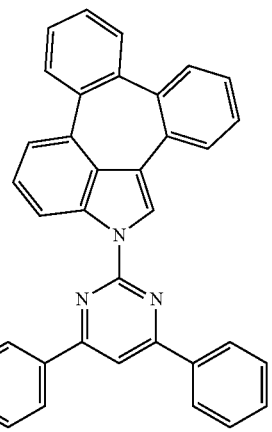

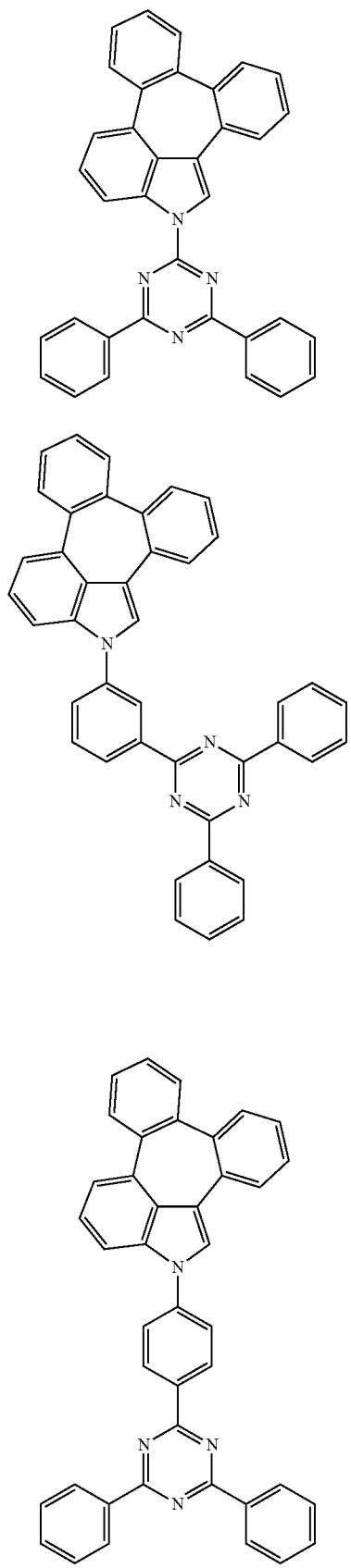
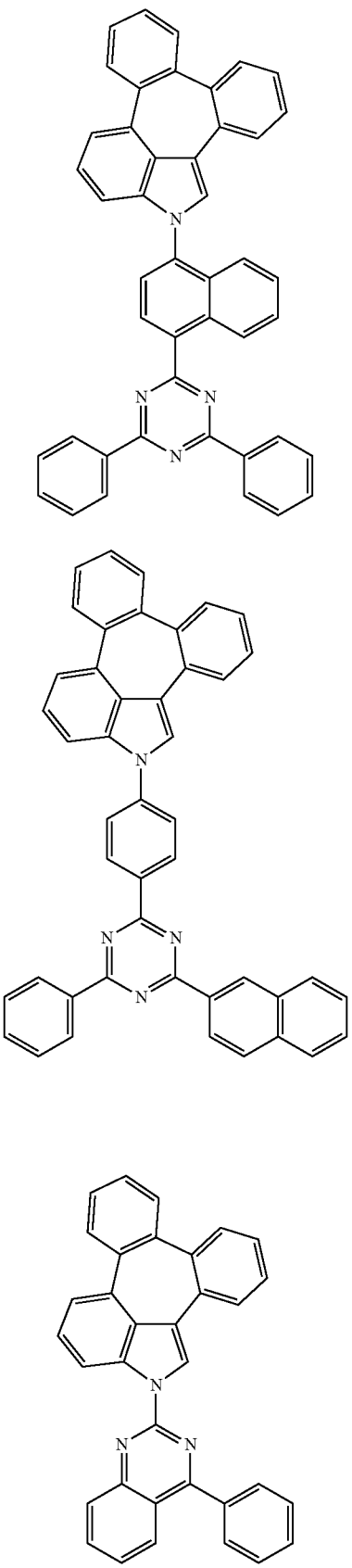

C-13
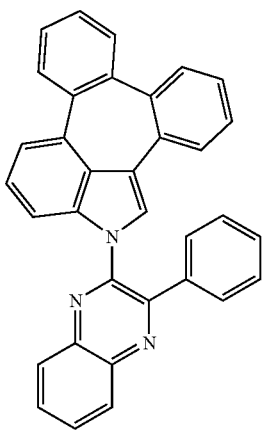
C-14
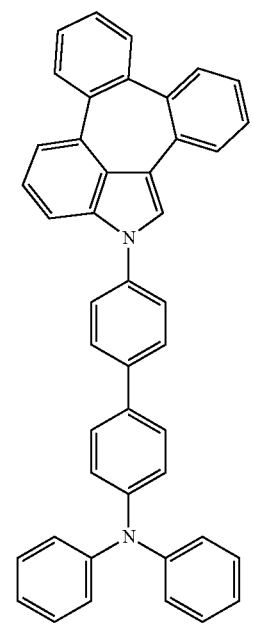
C-15
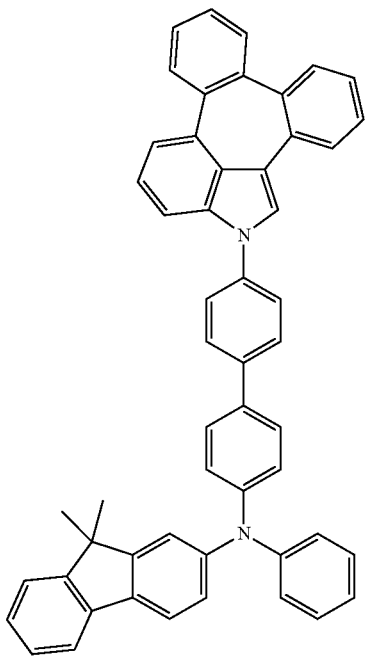
C-16
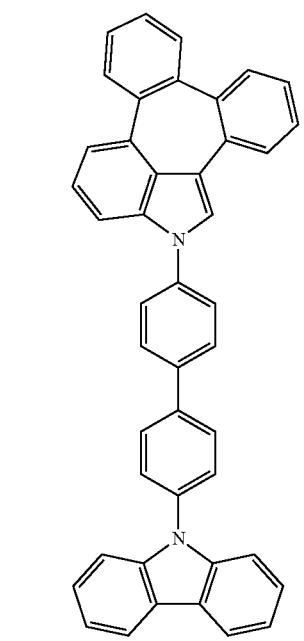
C-17
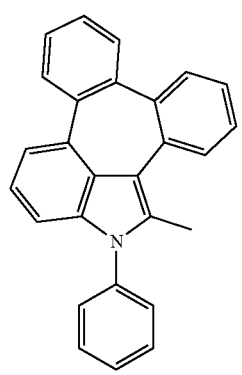

-continued
C-18
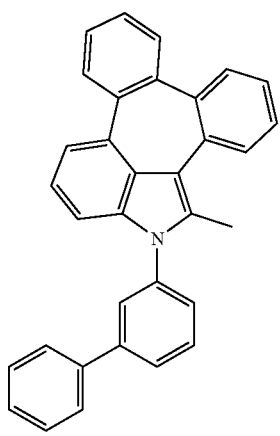
C-19
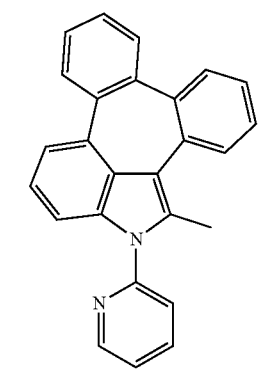
C-20
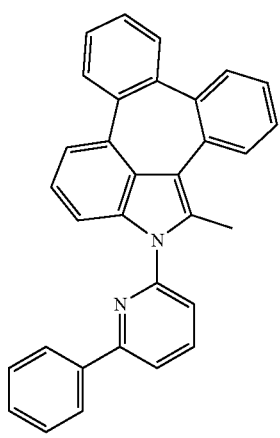
C-21
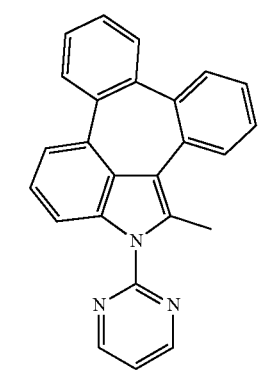
-continued
C-22
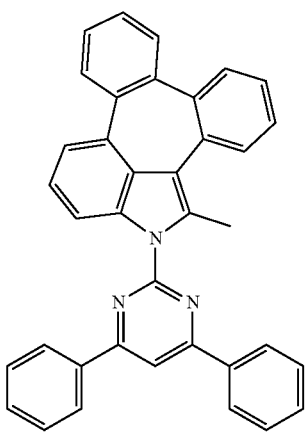
C-23
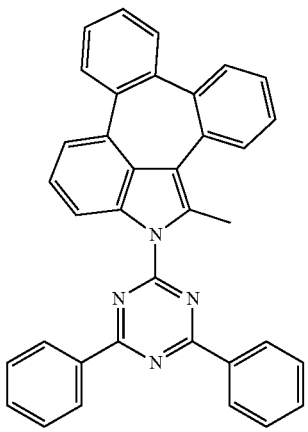
C-24
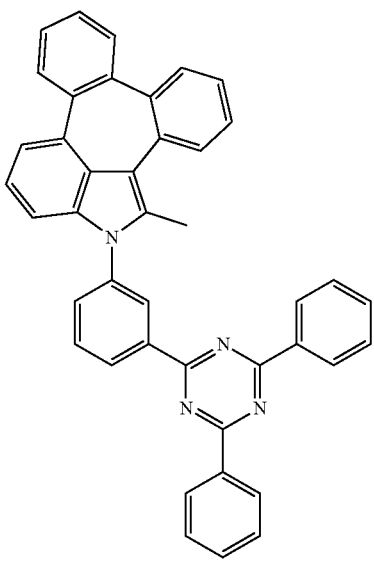

-continued
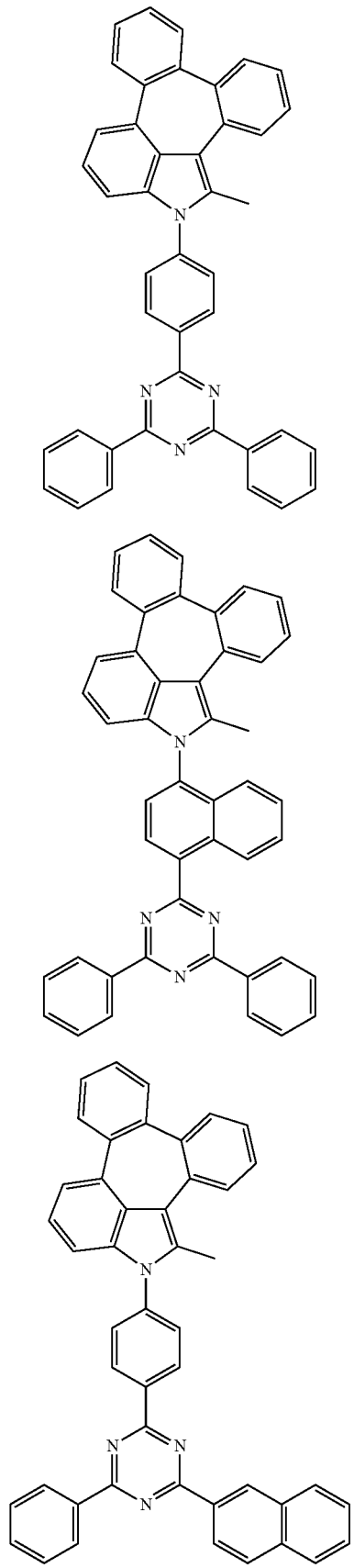
C-25
C-26
C-27
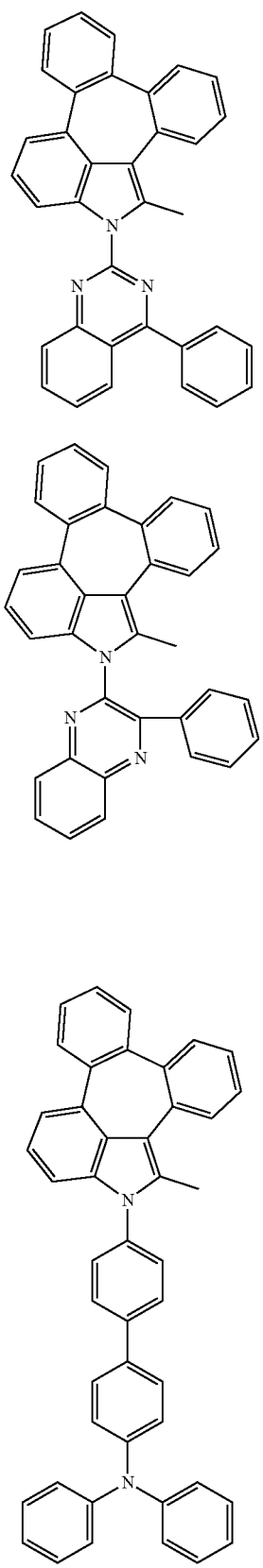
C-28
C-29
C-30

C-31
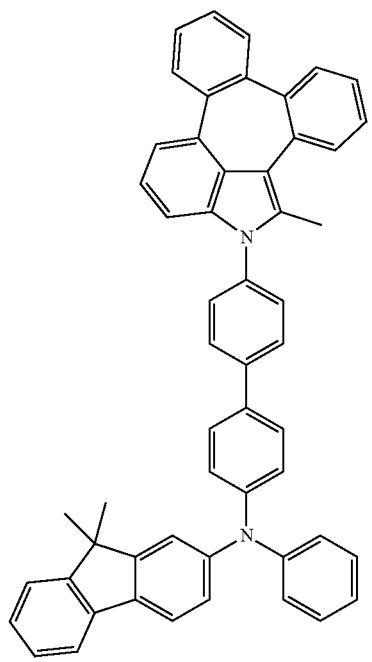
C-32
C-33
C-34
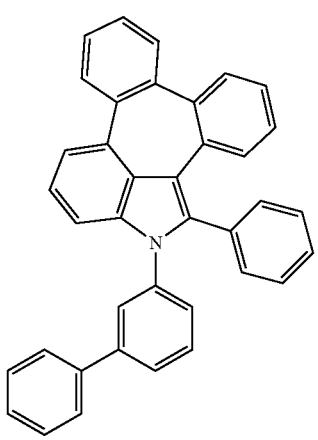
C-35
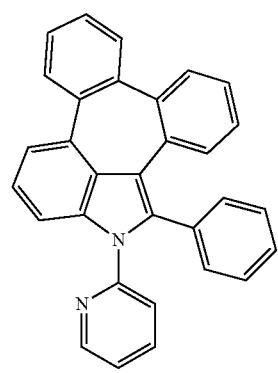
C-36
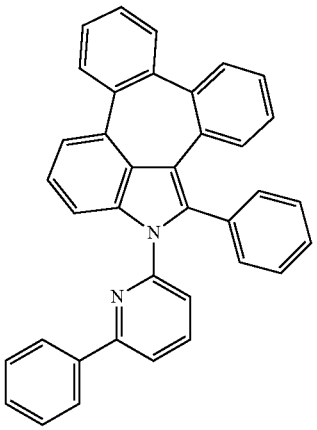
C-37
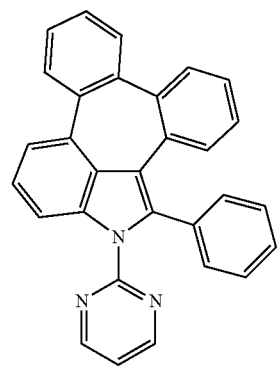

C-38
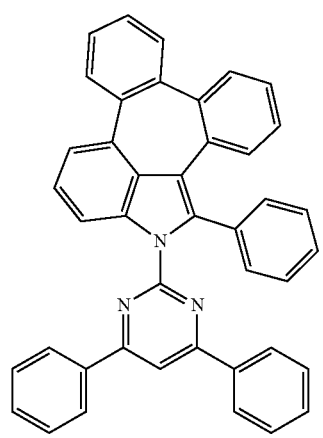
C-39
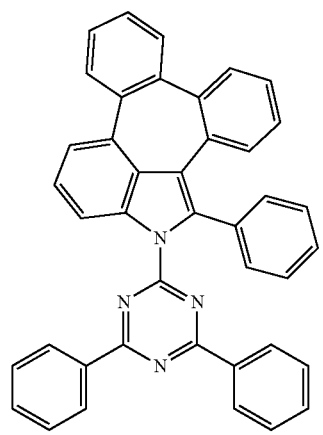
C-40
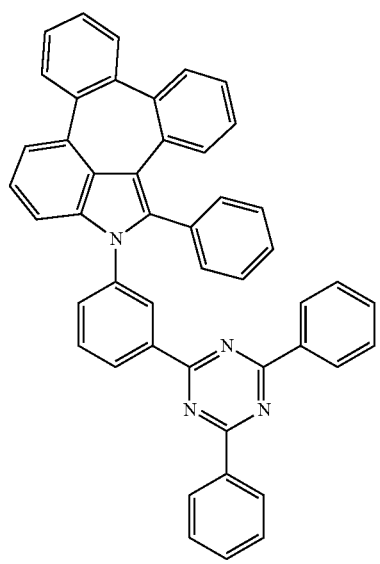
C-41
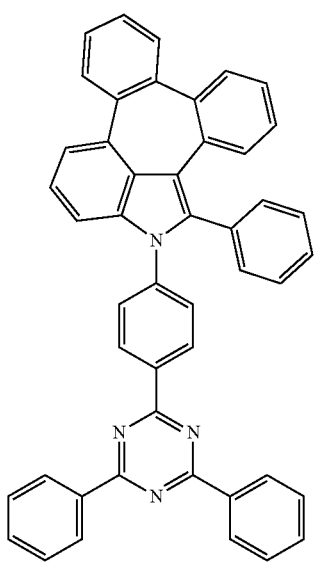
C-42
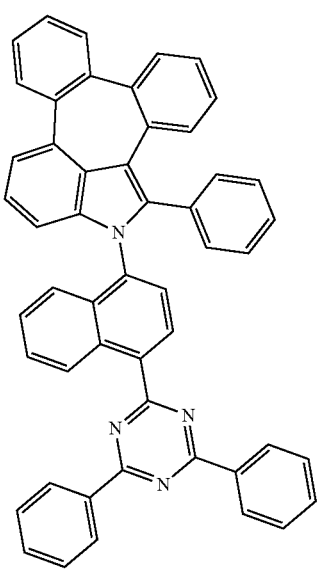

C-43
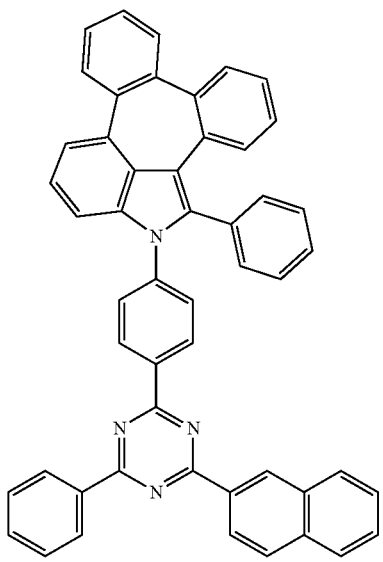
C-44
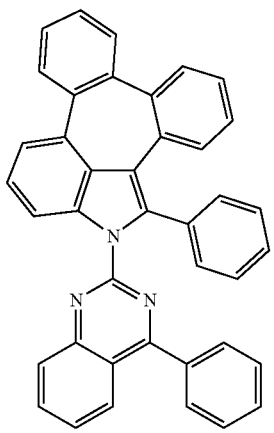
C-45
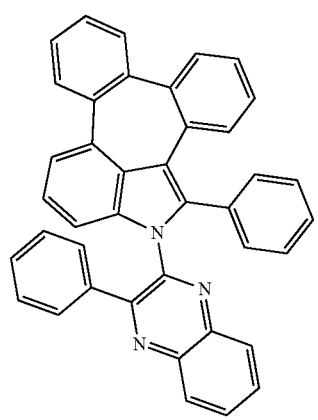
C-46
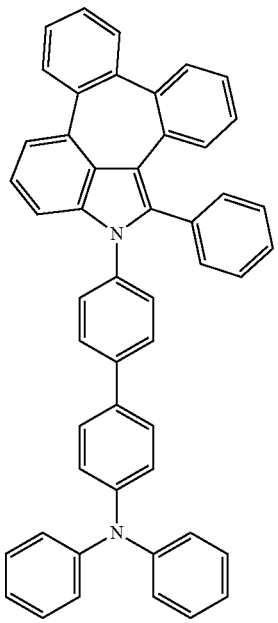
C-47
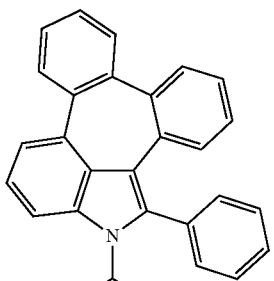
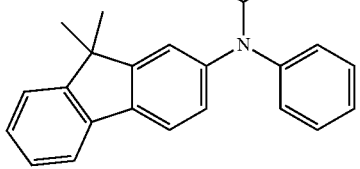

C-48
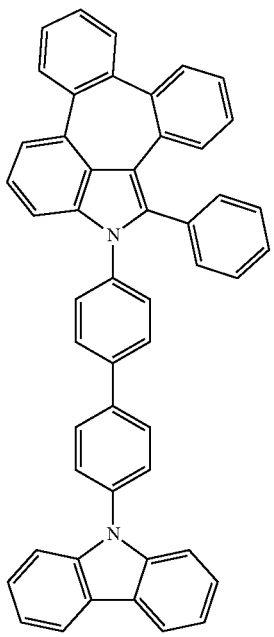
C-49
C-50
C-51
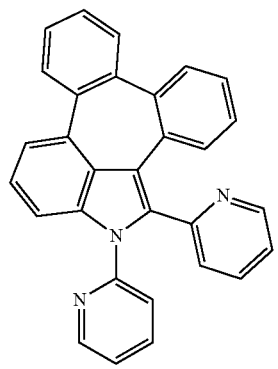
C-52
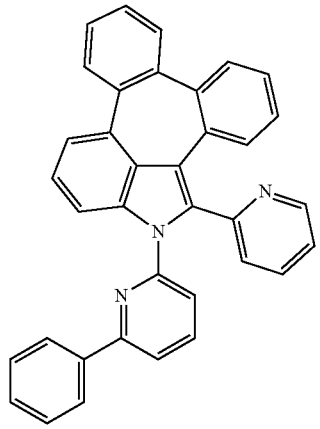
C-53
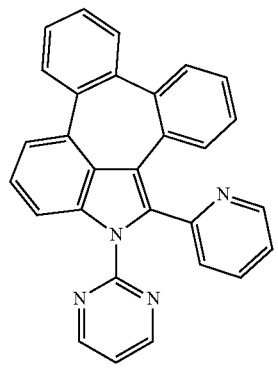
C-54
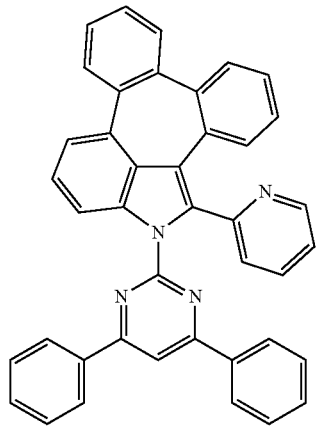

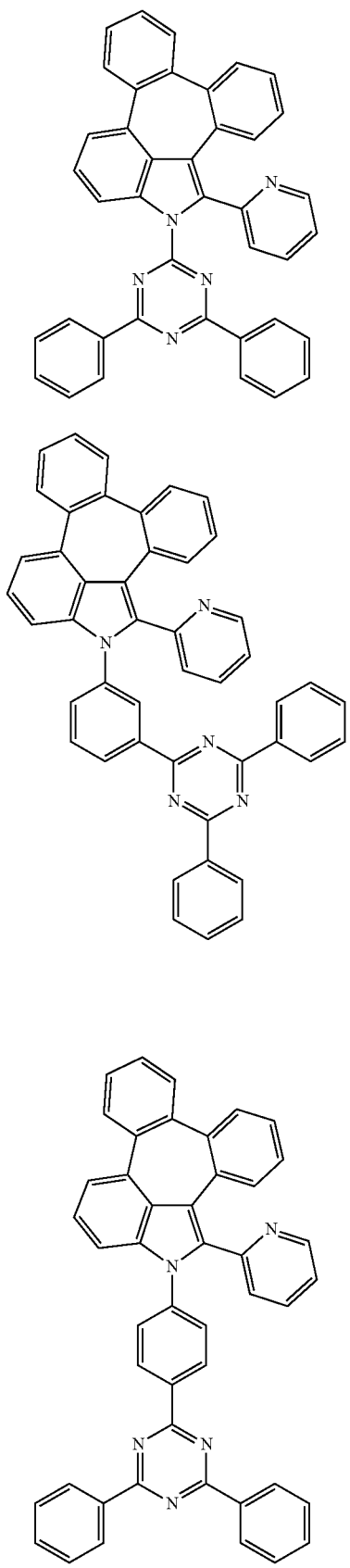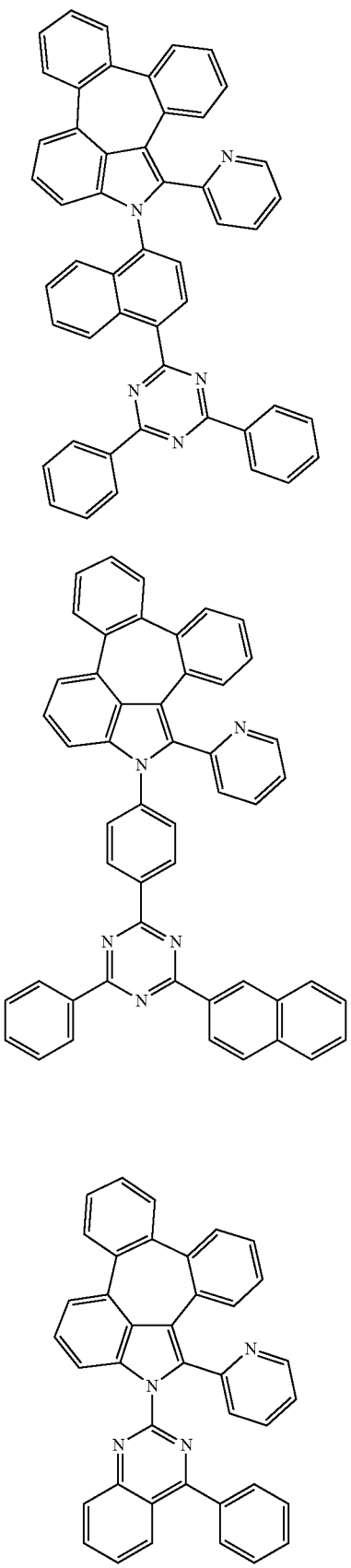

-continued
C-61
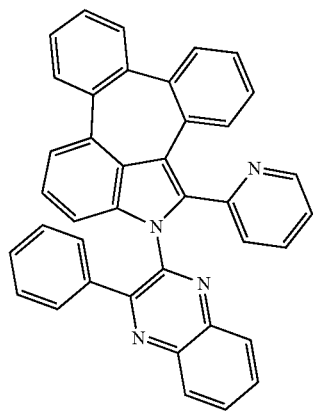
C-62
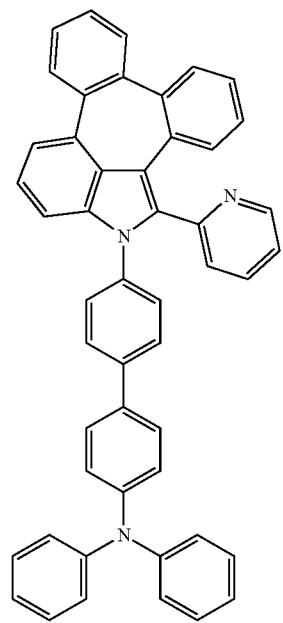
C-63
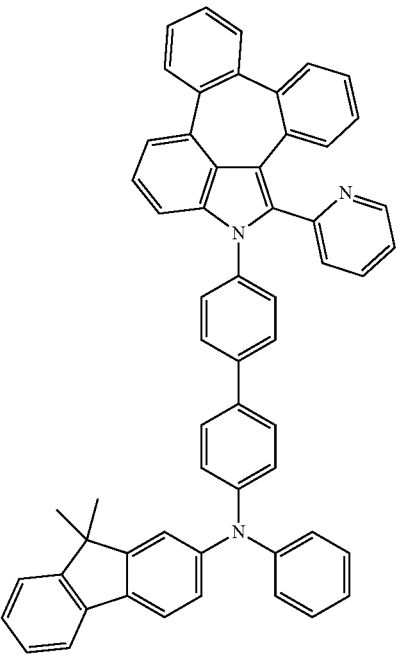
C-64
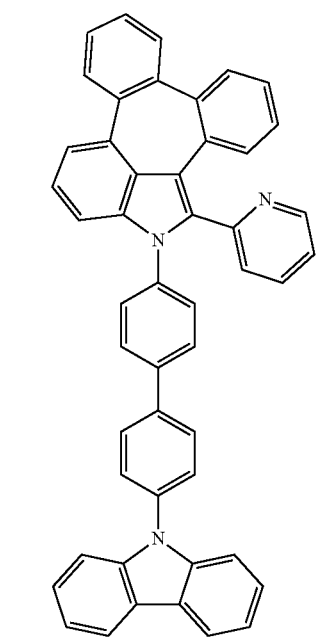
C-65
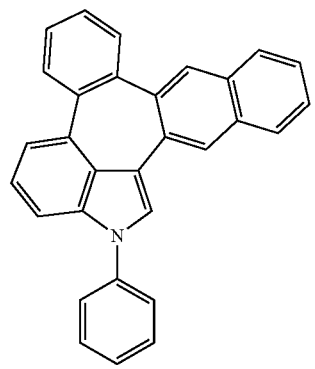

-continued
C-66
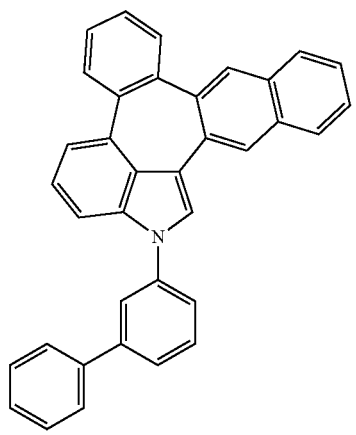
C-67
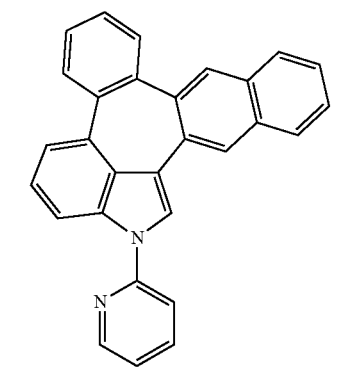
C-68
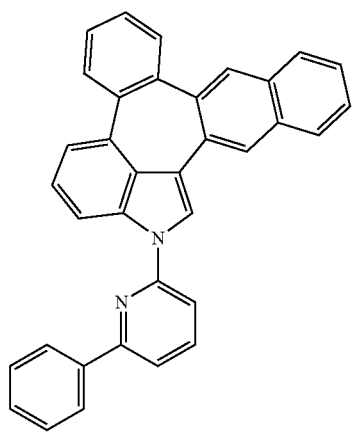
C-69
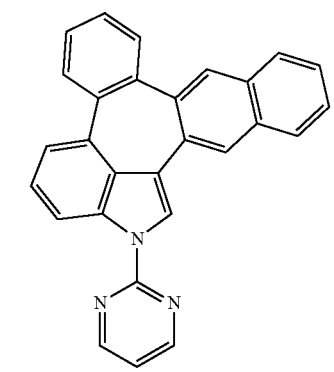
C-70
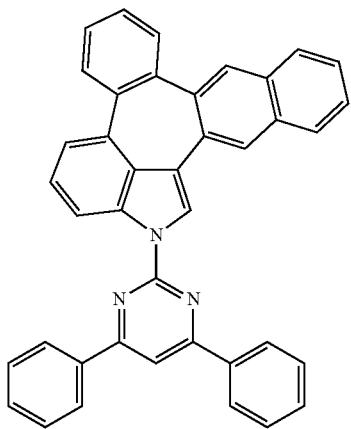
C-71
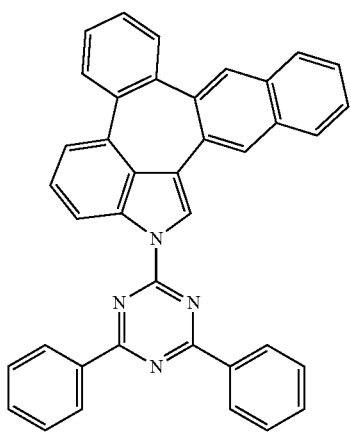
C-72
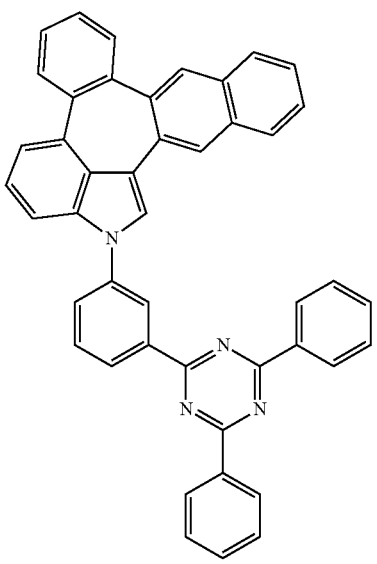

C-73
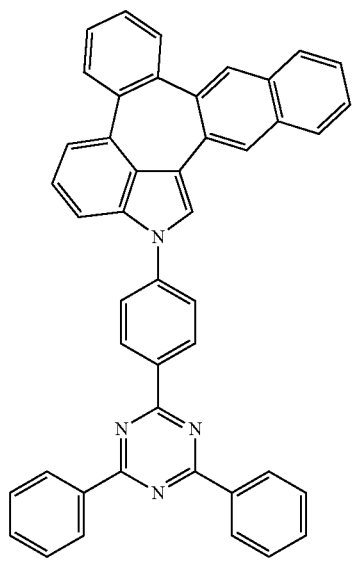
C-74
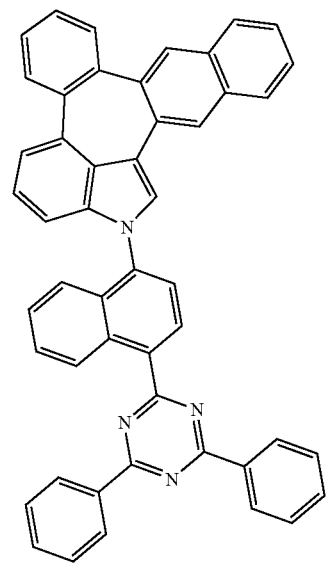
C-75
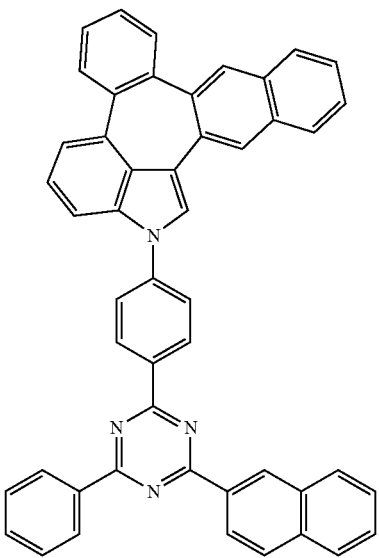
C-76
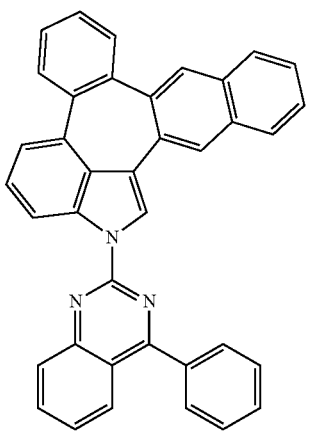
C-77
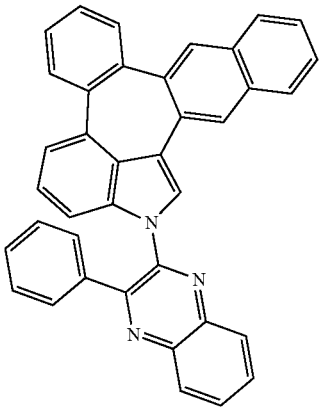

C-78
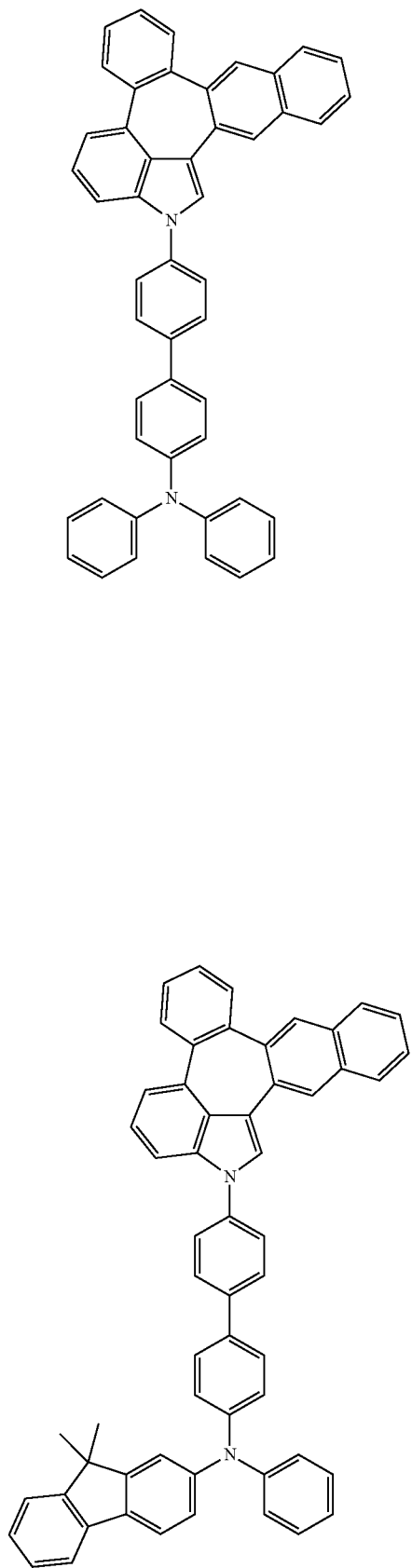
C-79
C-80
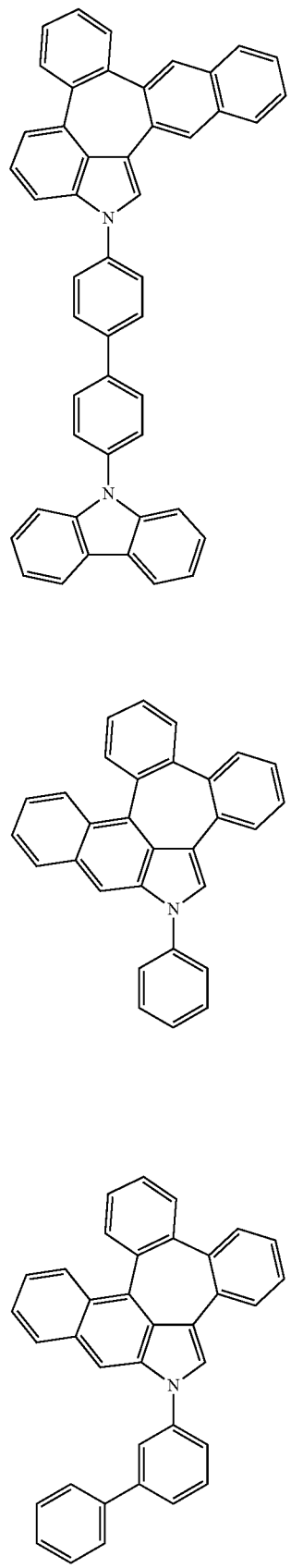
C-81
C-82

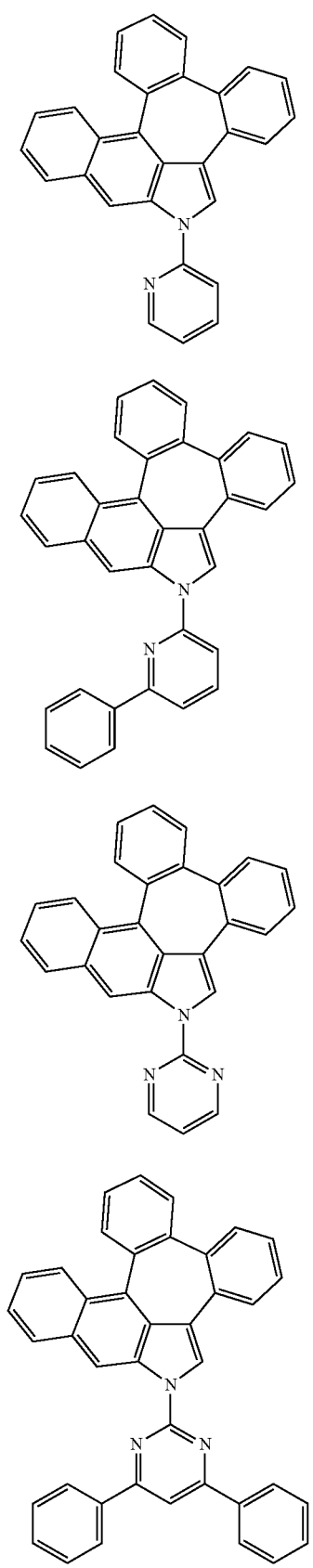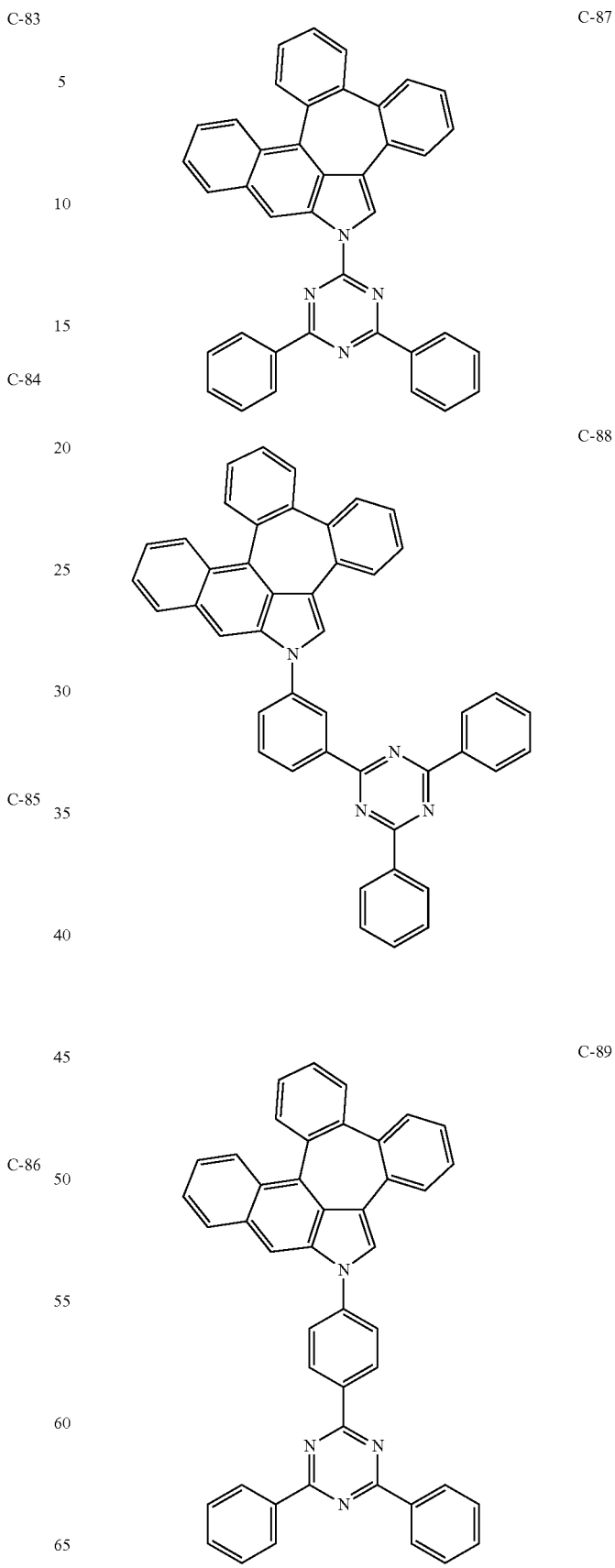

C-90
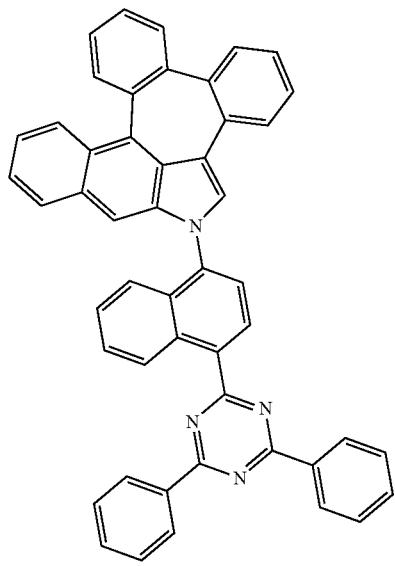
C-91
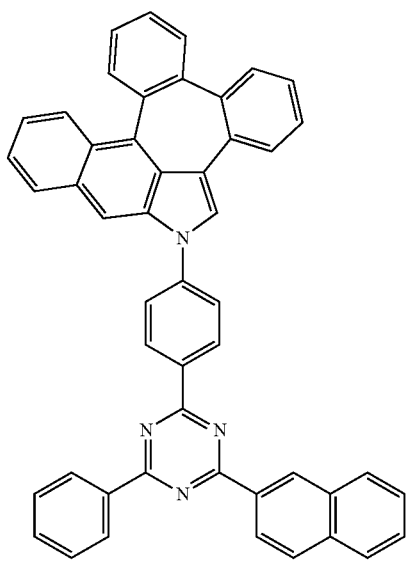
C-92
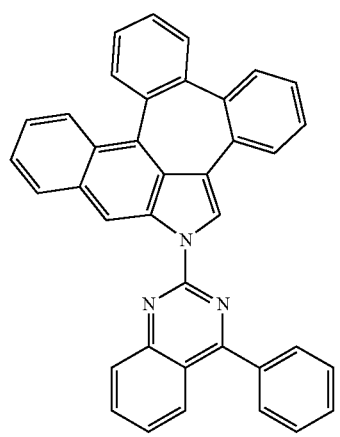
C-93
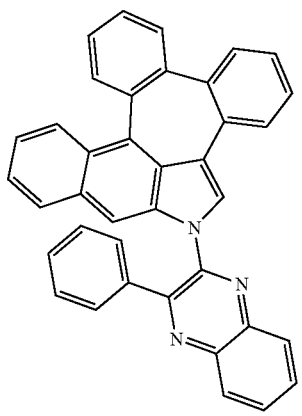
C-94
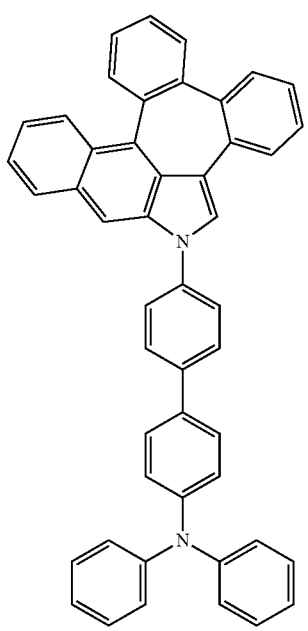

-continued
C-95
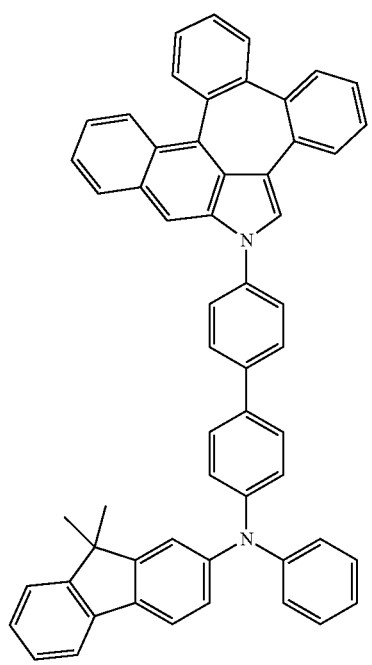
C-96
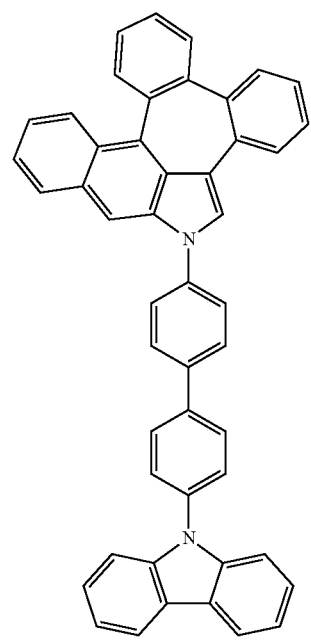
-continued
C-97
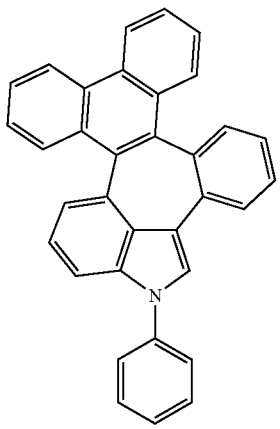
C-98
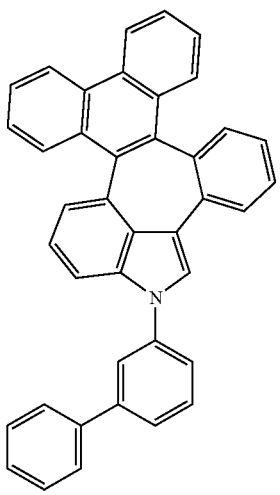
C-99
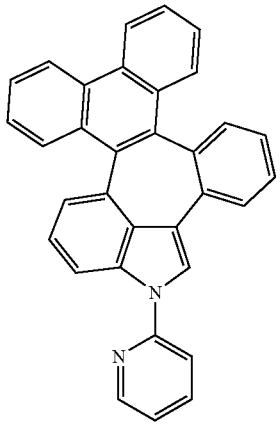

C-100
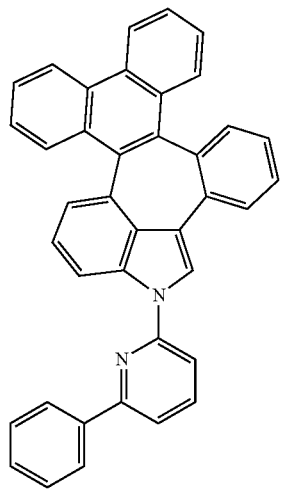
C-101
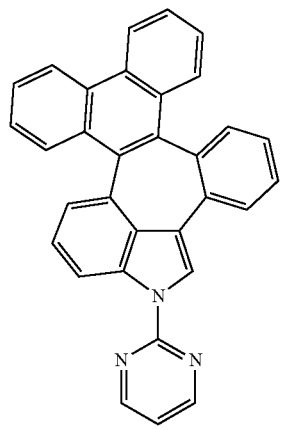
C-102
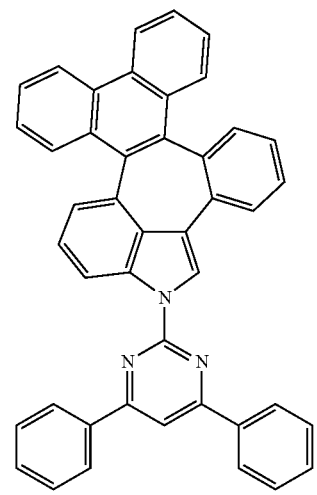
C-103
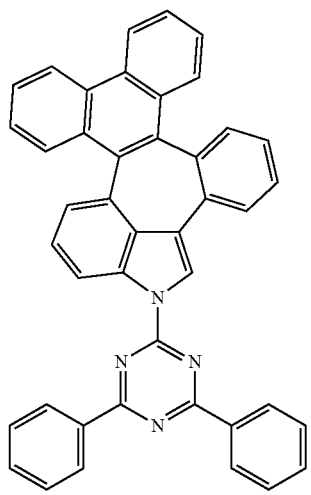
C-104
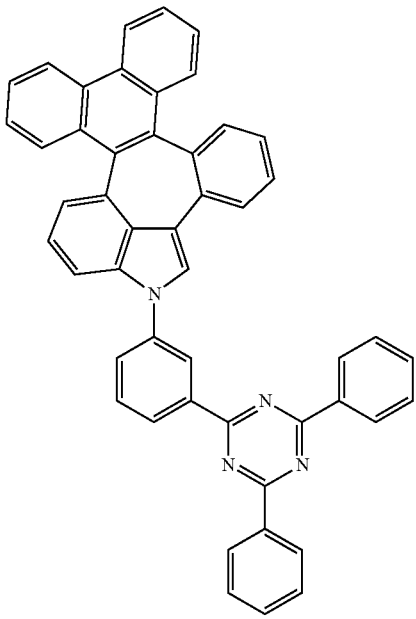

-continued
C-105
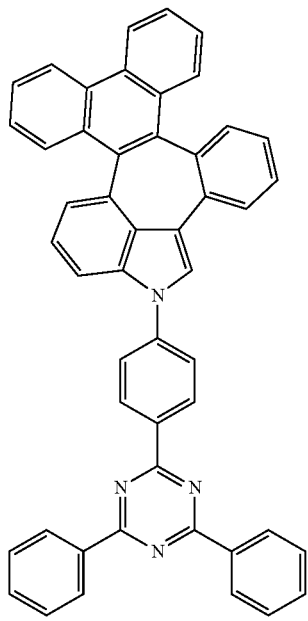
C-106
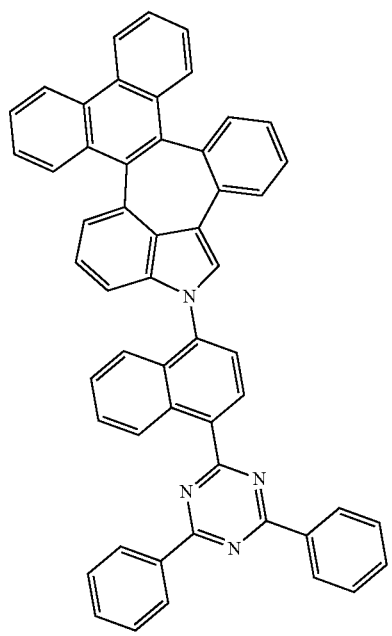
-continued
C-107
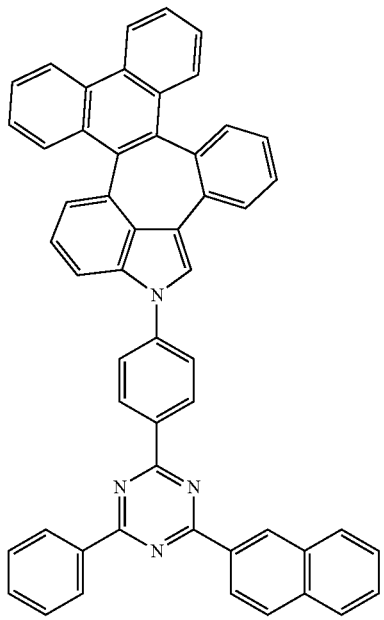
C-108
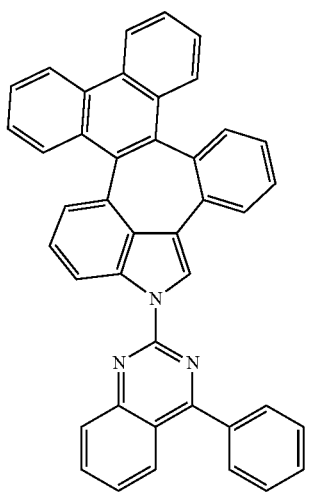
C-109

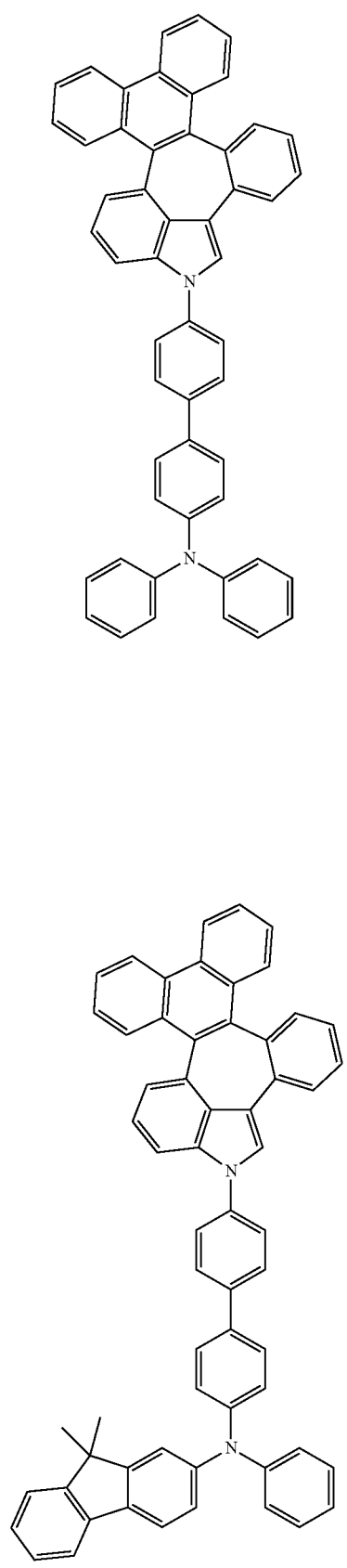

C-205
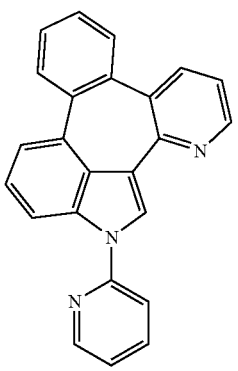
C-206
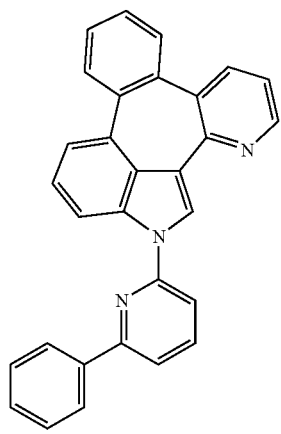
C-207
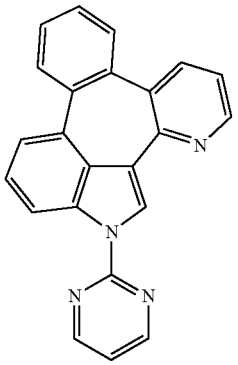
C-208
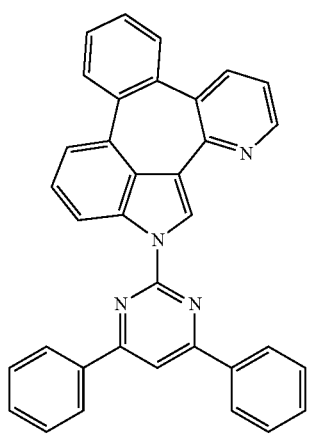
C-209
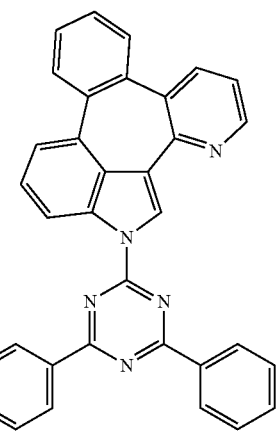
C-210
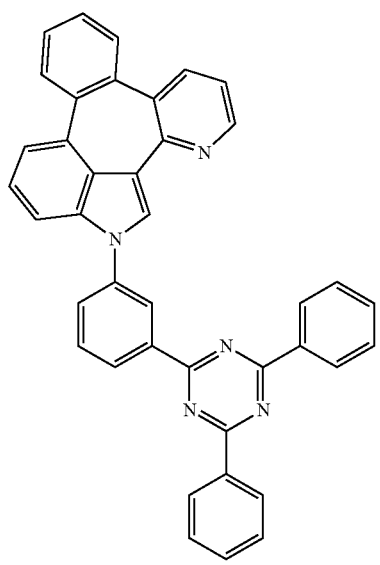
C-211
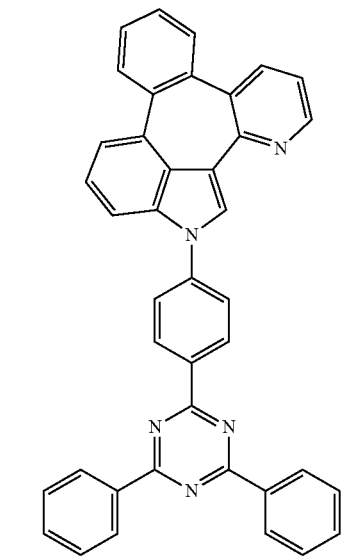

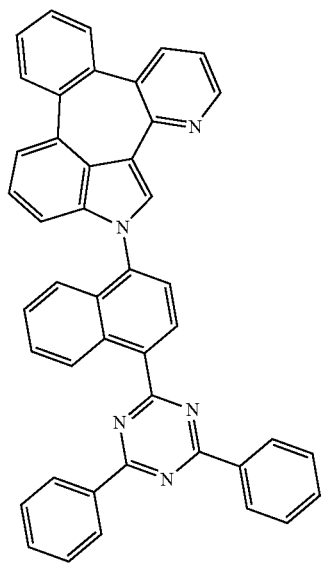
C-212
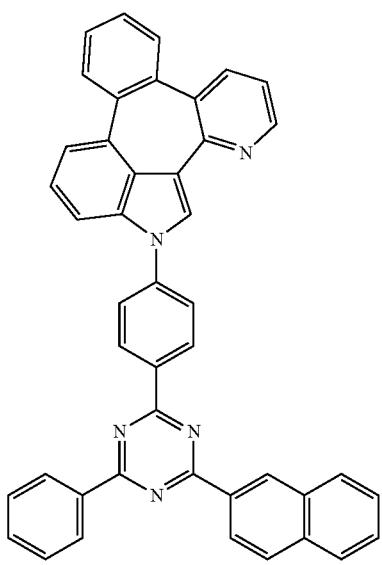
C-213
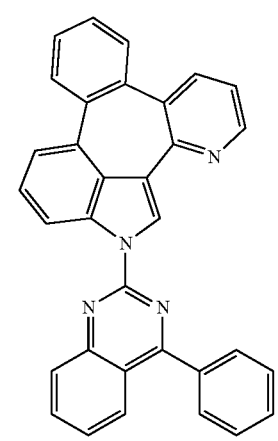
C-214
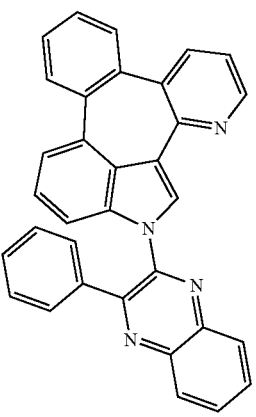
C-215
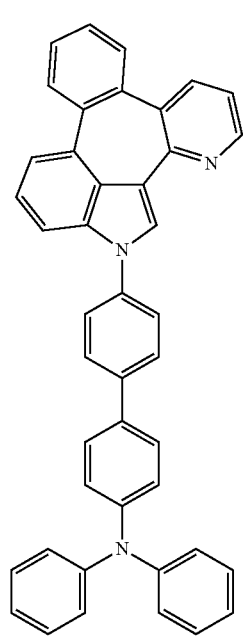
C-216

C-217
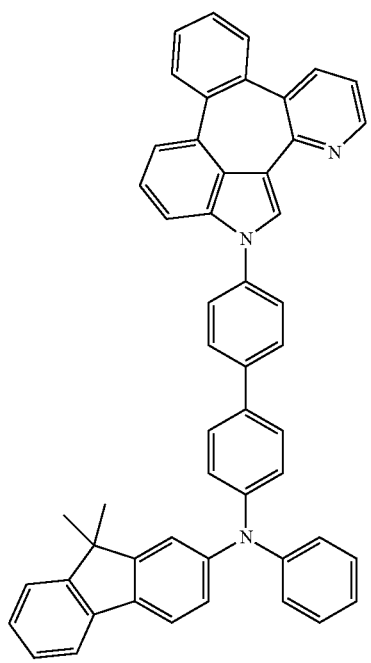
219
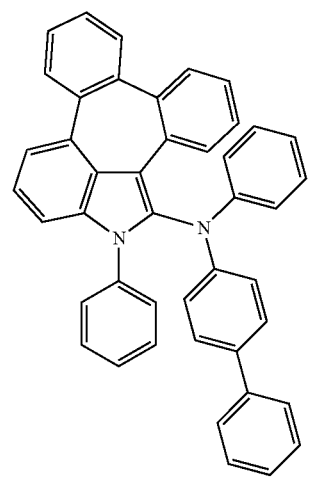
220
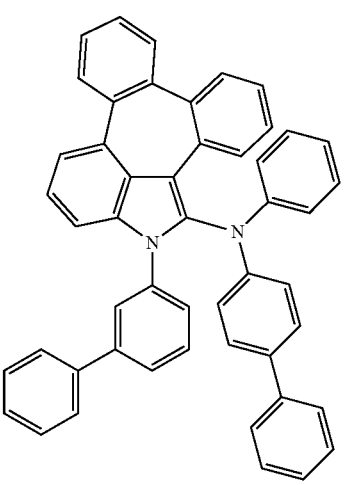
C-218
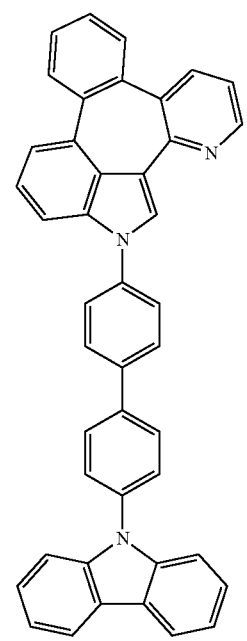
221
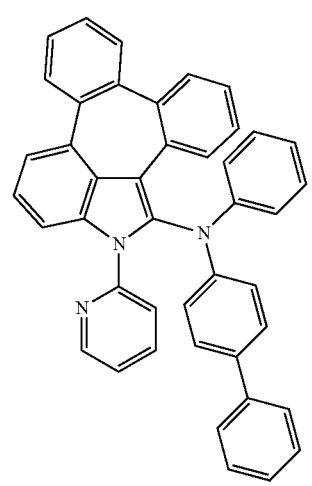

189
-continued
222
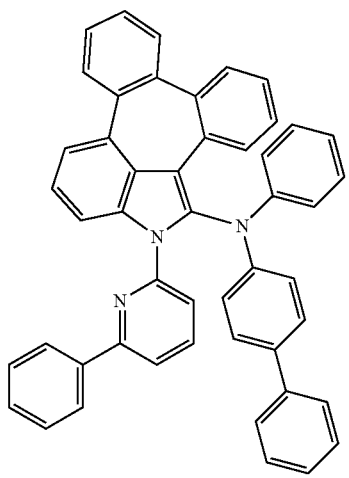
223
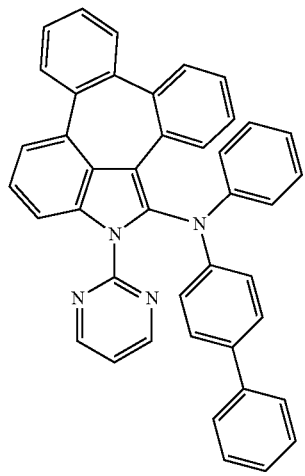
224
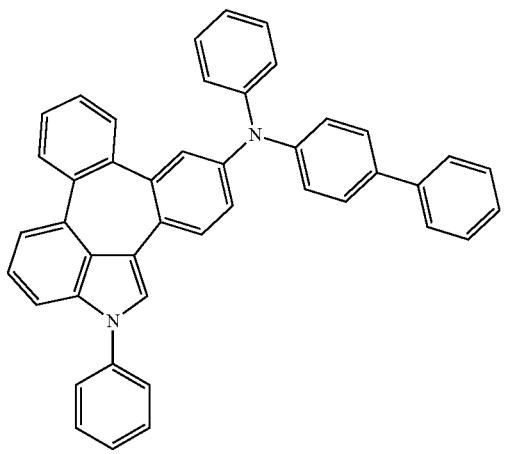
190
-continued
225
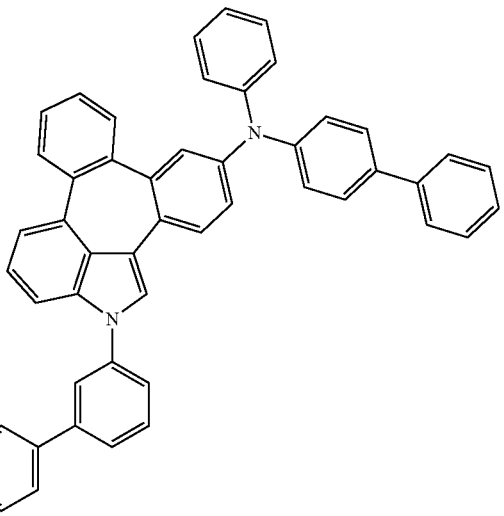
226
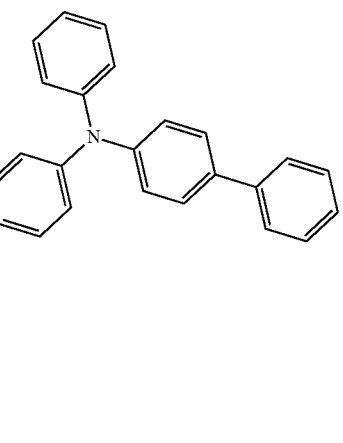
227
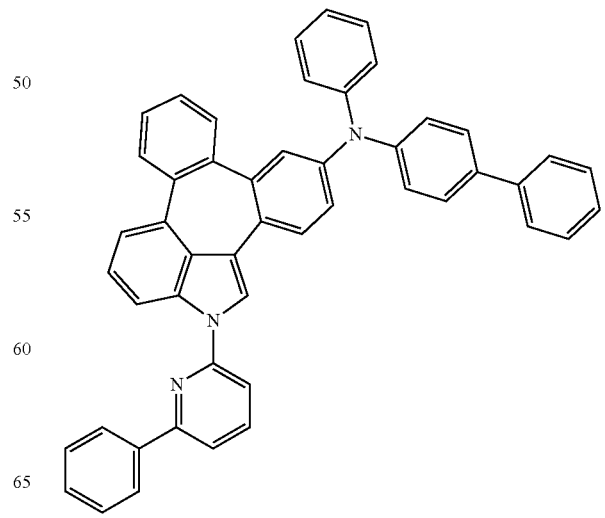

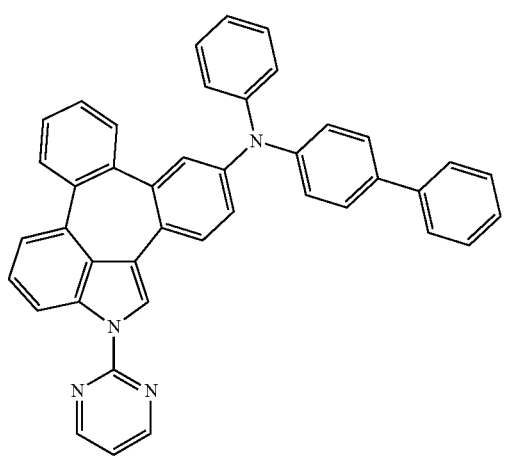
228
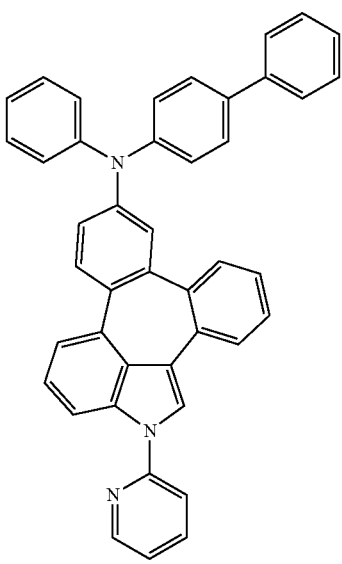
231
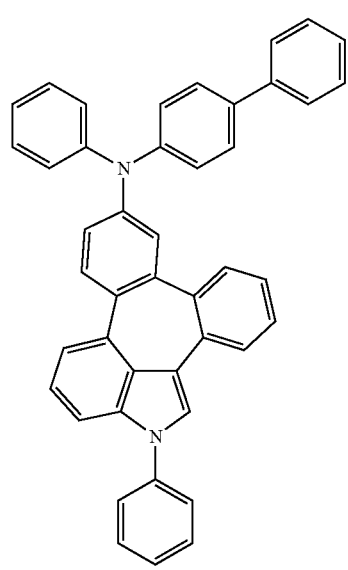
229
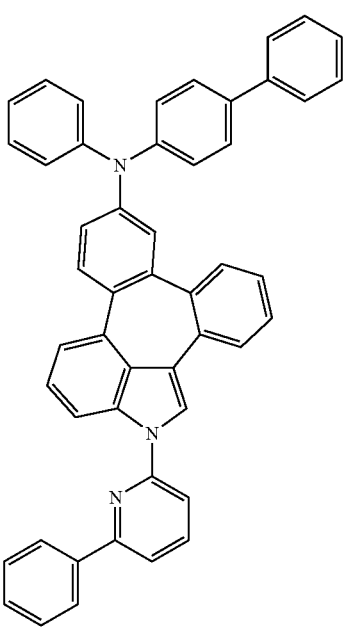
232
230

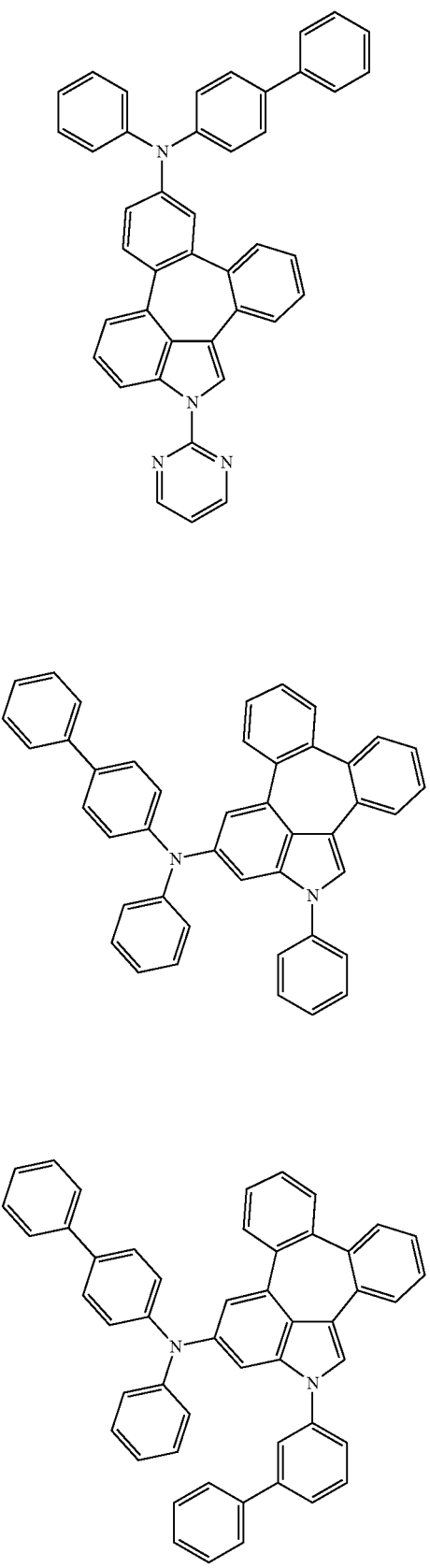
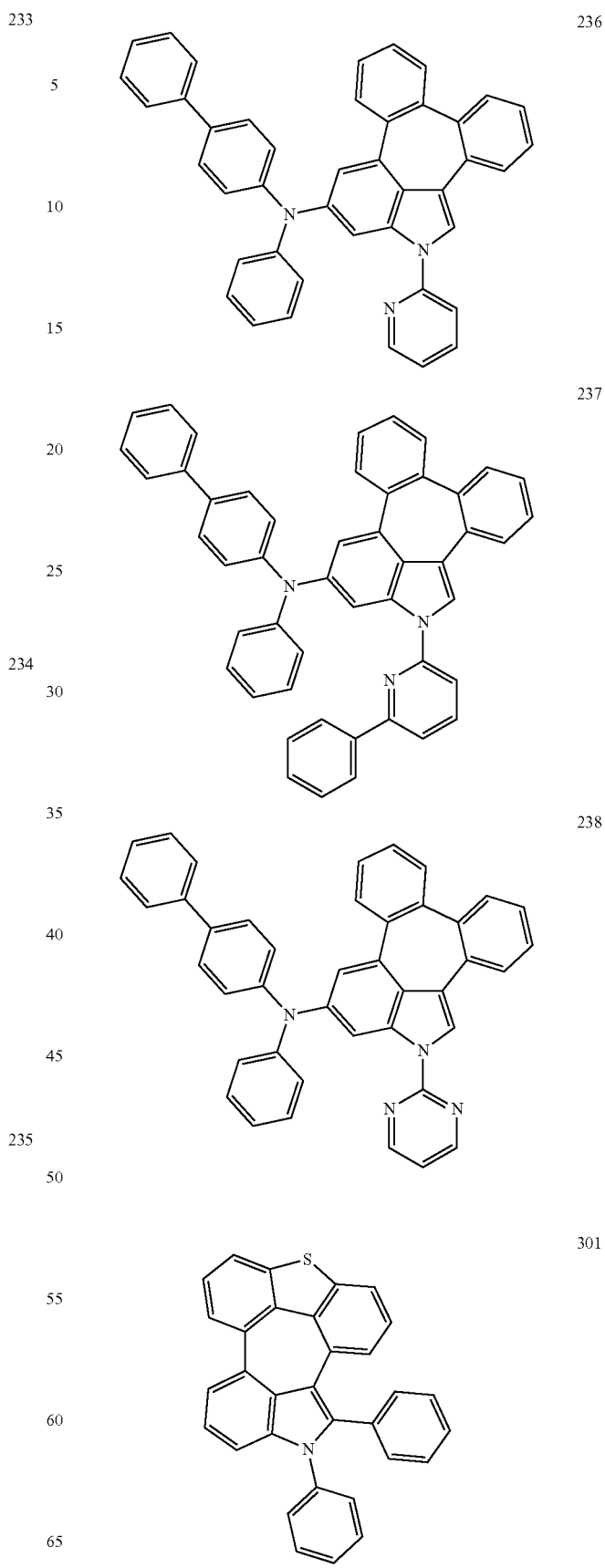

302
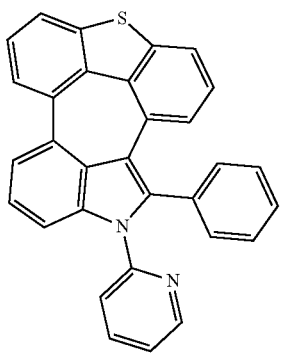
303
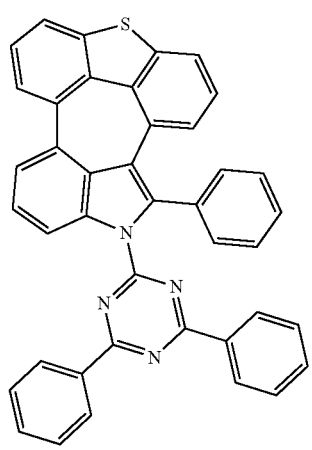
304
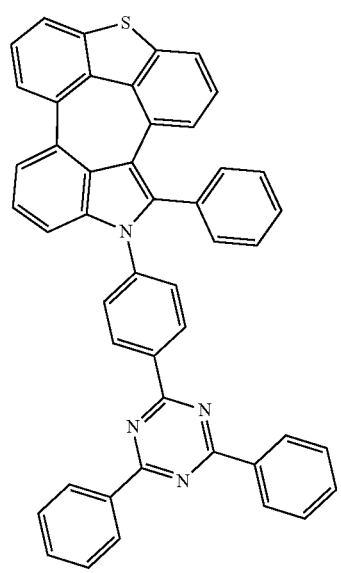
305
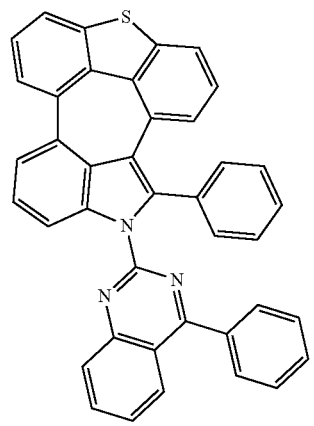
306
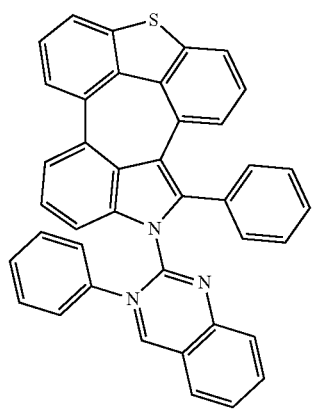
307
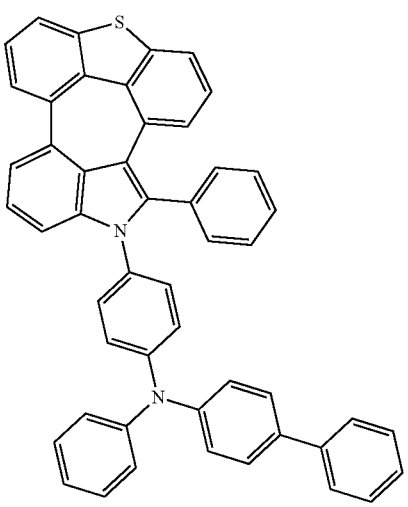

197
-continued
308
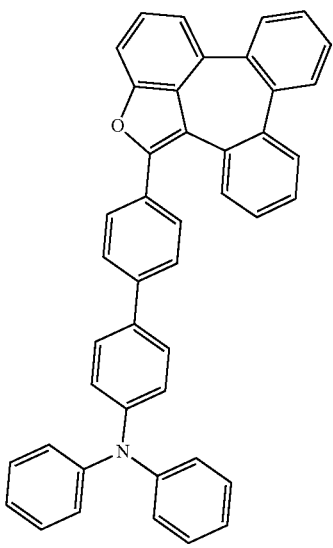
309
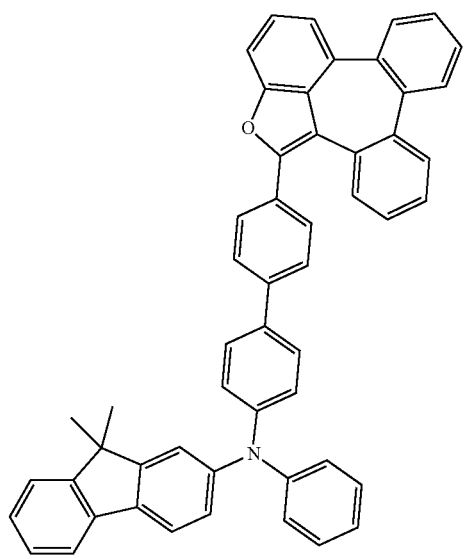
310
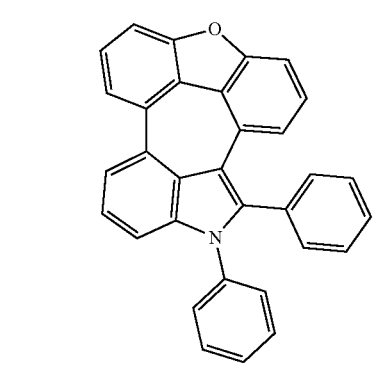
198
-continued
311
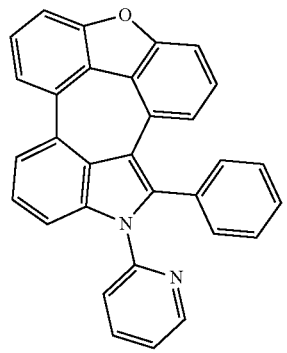
312
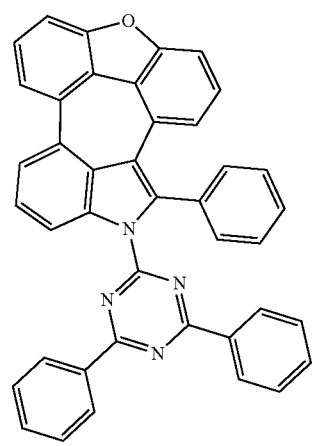
313
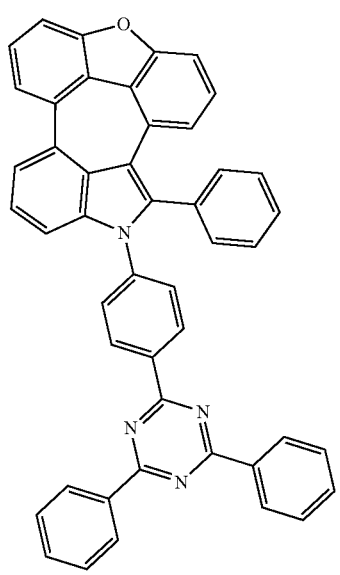

314
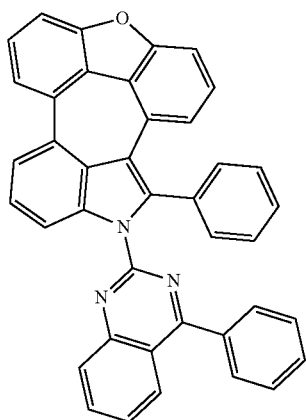
315
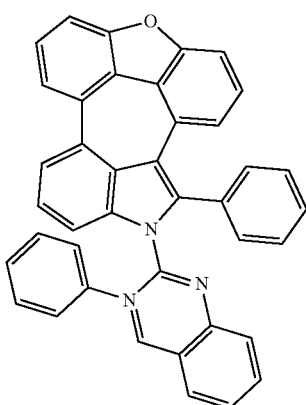
316
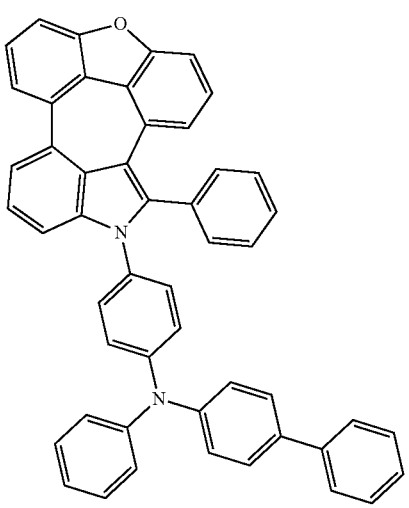
317
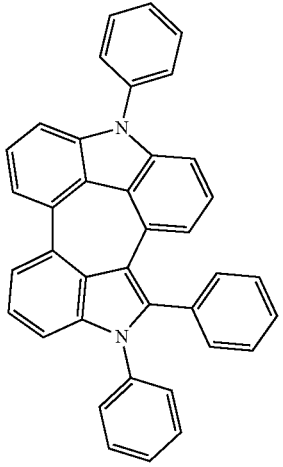
318
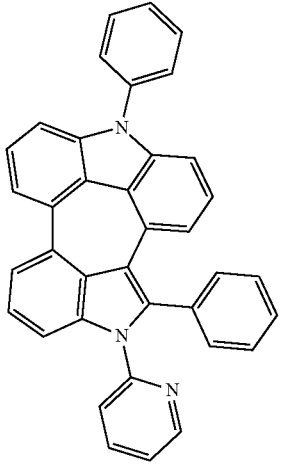
319
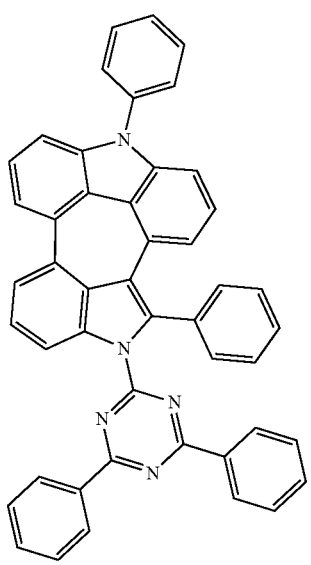

-continued
320
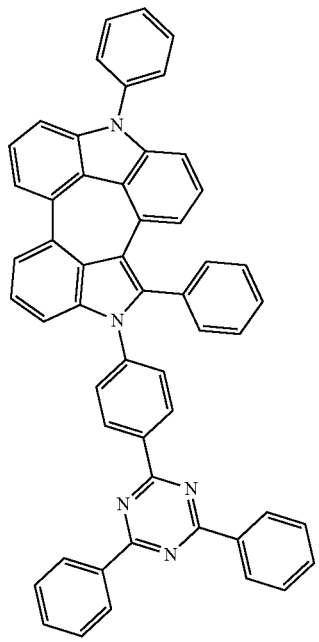
321
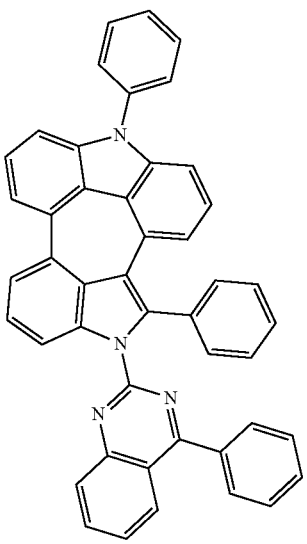
-continued
322
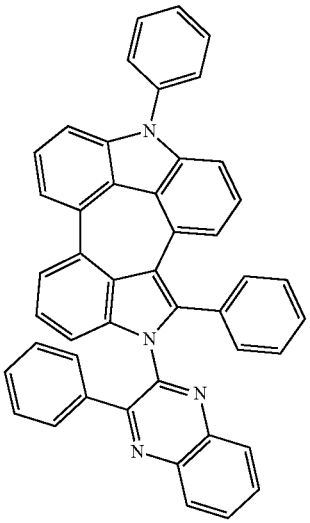
and
323
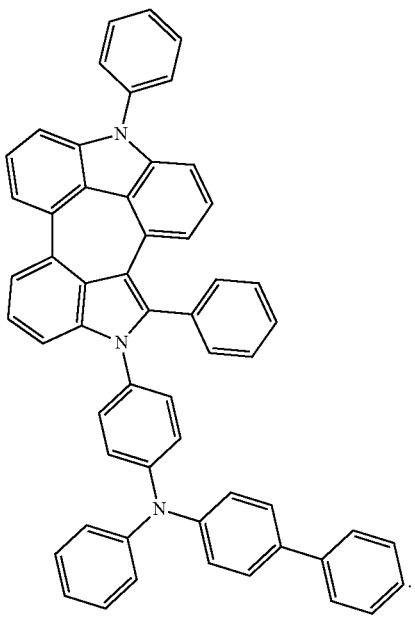
* * * * *